(12) United States Patent
Sharma et al.

(10) Patent No.: US 11,207,206 B2
(45) Date of Patent: Dec. 28, 2021

(54) FLUID REMOVAL DEVICE

(71) Applicant: CM Technologies, Inc., San Francisco, CA (US)

(72) Inventors: Amit Kumar Sharma, New Delhi (IN); Nishith Chasmawala, Gujarat (IN); John Everett Martin, Gainesville, FL (US)

(73) Assignee: CM Technologies, Inc., San Francisco, CA (US)

( * ) Notice: Subject to any disclaimer, the term of this patent is extended or adjusted under 35 U.S.C. 154(b) by 0 days.

(21) Appl. No.: 17/235,853

(22) Filed: Apr. 20, 2021

(65) Prior Publication Data

US 2021/0353449 A1 Nov. 18, 2021

(30) Foreign Application Priority Data

May 14, 2020 (IN) .............................. 202011020467

(51) Int. Cl.
    *A61F 5/453* (2006.01)
    *A61F 5/44* (2006.01)
    *A61F 5/455* (2006.01)

(52) U.S. Cl.
    CPC ............ *A61F 5/453* (2013.01); *A61F 5/4401* (2013.01); *A61F 5/4404* (2013.01); *A61F 5/4408* (2013.01); *A61F 5/455* (2013.01)

(58) Field of Classification Search
    CPC combination set(s) only.
    See application file for complete search history.

(56) References Cited

U.S. PATENT DOCUMENTS

| 3,349,768 | A |   | 10/1967 | Xavier |   |
|---|---|---|---|---|---|
| 3,511,241 | A | * | 5/1970 | Lee | A61F 5/453 604/352 |
| 3,512,185 | A |   | 5/1970 | Elis |   |
| 3,881,486 | A | * | 5/1975 | Fenton | A61F 5/4405 604/335 |
| 4,020,843 | A | * | 5/1977 | Kanall | A61F 5/453 604/351 |
| 4,022,213 | A | * | 5/1977 | Stein | A61F 5/453 604/350 |

(Continued)

FOREIGN PATENT DOCUMENTS

| EP | 0032138 B1 | 11/1984 |
|---|---|---|
| GB | 1571657 A | 7/1980 |

(Continued)

*Primary Examiner* — Guy K Townsend
(74) *Attorney, Agent, or Firm* — Shay Glenn LLP

(57) ABSTRACT

A urine removal device includes a pouch with a proximal opening that provides access to an internal compartment of the pouch that is suitable to contain urine. A fluid diverter system is disposed inside of the pouch and extends from the proximal portion of the pouch, where it interfaces via an outlet conduit member to the environment outside of the pouch, to the distal end of the pouch where it draws in urine from the pouch. The pouch has at least one air port to allow air flow through the device to support suction that is applied inside of the pouch. The fluid diverter system has at least one conduit member configured to draw urine from the distal portion of the pouch up to the proximal end of the pouch, and into the outlet conduit member where it exits the fluid collection device.

25 Claims, 39 Drawing Sheets

(56) References Cited

U.S. PATENT DOCUMENTS

| | | | | |
|---|---|---|---|---|
| 4,084,589 A | * | 4/1978 | Kulvi | A61B 10/007 604/73 |
| 4,246,901 A | | 1/1981 | Frosch et al. | |
| 4,257,418 A | | 3/1981 | Hessner | |
| 4,281,655 A | * | 8/1981 | Terauchi | A61F 5/451 4/305 |
| 4,387,726 A | | 6/1983 | Denard | |
| 4,457,314 A | | 7/1984 | Knowles | |
| 4,466,888 A | * | 8/1984 | Verkaart | A61M 1/0001 210/232 |
| 4,625,734 A | * | 12/1986 | Sherlock | A61B 5/208 600/575 |
| 4,692,160 A | | 9/1987 | Nussbaumer | |
| 4,747,166 A | | 5/1988 | Kuntz | |
| 4,795,449 A | | 1/1989 | Schneider et al. | |
| 4,799,928 A | | 1/1989 | Crowley | |
| 4,804,377 A | * | 2/1989 | Hanifl | A61F 5/44 4/144.2 |
| 4,886,508 A | | 12/1989 | Washington | |
| 4,889,533 A | | 12/1989 | Beecher | |
| 5,300,052 A | * | 4/1994 | Kubo | A61F 5/453 4/144.1 |
| 5,735,837 A | * | 4/1998 | Ishikawa | A61F 5/453 604/385.09 |
| 5,827,257 A | * | 10/1998 | Fujioka | A61F 13/471 604/385.19 |
| 6,311,339 B1 | | 11/2001 | Kraus | |
| 6,464,674 B1 | * | 10/2002 | Palumbo | A61F 5/443 604/317 |
| 6,530,909 B1 | * | 3/2003 | Nozaki | A61F 13/471 604/349 |
| 6,569,133 B2 | | 5/2003 | Cheng et al. | |
| 6,635,038 B2 | * | 10/2003 | Scovel | A61F 5/453 604/347 |
| 6,732,384 B2 | | 5/2004 | Scott | |
| 6,857,137 B2 | | 2/2005 | Otto | |
| 7,186,245 B1 | * | 3/2007 | Cheng | A61F 5/44 604/349 |
| 7,390,320 B2 | | 6/2008 | Machida et al. | |
| 7,755,497 B2 | | 7/2010 | Wada et al. | |
| 7,927,320 B2 | | 4/2011 | Goldwasser et al. | |
| 8,075,538 B2 | * | 12/2011 | Vernon | A61F 5/4404 604/322 |
| 8,196,230 B2 | * | 6/2012 | Nakamura | A61G 7/02 4/321 |
| 8,287,508 B1 | | 10/2012 | Sanchez | |
| 8,303,554 B2 | | 11/2012 | Tsai et al. | |
| 9,173,799 B2 | * | 11/2015 | Tanimoto | A61F 5/451 4/471 |
| 9,445,934 B2 | * | 9/2016 | Ugarte | A61F 5/453 604/347 |
| 9,788,992 B2 | * | 10/2017 | Harvie | A61M 25/0017 210/232 |
| 10,064,774 B2 | * | 9/2018 | Onoda | A61F 5/451 |
| 10,226,376 B2 | | 3/2019 | Sanchez et al. | |
| 10,376,406 B2 | | 8/2019 | Newton | |
| 10,376,407 B2 | | 8/2019 | Newton | |
| 10,390,989 B2 | | 8/2019 | Sanchez et al. | |
| 10,426,654 B2 | * | 10/2019 | Ugarte | A61F 5/453 604/347 |
| 10,857,025 B2 | | 12/2020 | Davis et al. | |
| 10,952,889 B2 | | 3/2021 | Newton et al. | |
| 10,973,678 B2 | * | 4/2021 | Newton | A61M 1/0023 |
| 11,026,829 B2 | * | 6/2021 | Harvie | A61F 5/455 |
| 2002/0087131 A1 | | 7/2002 | Wolff et al. | |
| 2003/0163120 A1 | | 8/2003 | Harvie | |
| 2004/0006321 A1 | * | 1/2004 | Cheng | A61F 5/44 604/349 |
| 2006/0253091 A1 | * | 11/2006 | Vernon | A61F 5/4405 604/353 |
| 2008/0281284 A1 | * | 11/2008 | Garfield | A61F 5/4404 604/327 |
| 2009/0193571 A1 | * | 8/2009 | Nakamura | A61G 7/02 4/300 |
| 2010/0298789 A1 | * | 11/2010 | Santimaw | A61F 5/451 604/319 |
| 2011/0060300 A1 | * | 3/2011 | Weig | A61M 1/743 604/319 |
| 2012/0103347 A1 | | 5/2012 | Wheaton et al. | |
| 2012/0116336 A1 | * | 5/2012 | Sharma | A61M 25/04 604/328 |
| 2014/0157499 A1 | * | 6/2014 | Suzuki | A47K 11/00 4/144.3 |
| 2014/0182051 A1 | * | 7/2014 | Tanimoto | A61G 9/006 4/144.3 |
| 2014/0276494 A1 | * | 9/2014 | Cisko | A61M 1/602 604/319 |
| 2015/0135423 A1 | * | 5/2015 | Sharpe | A61F 5/453 4/471 |
| 2016/0051395 A1 | * | 2/2016 | Ugarte M.D. | A61F 5/4408 604/544 |
| 2016/0367226 A1 | | 12/2016 | Newton et al. | |
| 2017/0000642 A1 | * | 1/2017 | Cisko | A61F 5/44 604/347 |
| 2017/0007438 A1 | * | 1/2017 | Harvie | A61M 25/0017 210/232 |
| 2017/0042724 A1 | * | 2/2017 | Ugarte | A61F 5/4556 604/347 |
| 2017/0252202 A9 | | 9/2017 | Sanchez et al. | |
| 2017/0312405 A1 | | 11/2017 | Newton | |
| 2019/0038451 A1 | * | 2/2019 | Harvie | A61F 5/453 604/347 |
| 2019/0247222 A1 | * | 8/2019 | Ecklund | A61F 5/443 604/347 |
| 2019/0358075 A1 | * | 11/2019 | Scharich, III | A61G 7/0503 4/300 |
| 2019/0365561 A1 | | 12/2019 | Newton et al. | |
| 2020/0085610 A1 | | 3/2020 | Cohn et al. | |
| 2020/0315838 A1 | | 10/2020 | Eckert | |
| 2020/0390591 A1 | | 12/2020 | Glithero et al. | |
| 2021/0113130 A1 | * | 4/2021 | Tran | A61F 5/453 604/347 |

FOREIGN PATENT DOCUMENTS

| | | |
|---|---|---|
| GB | 2260907 B | 5/1995 |
| WO | WO2004/026194 A1 | 4/2004 |
| WO | WO2016/103242 A1 | 6/2016 |
| WO | WO2019/212949 A1 | 11/2019 |
| WO | WO2019/212950 A1 | 11/2019 |
| WO | WO2019/212951 A1 | 11/2019 |
| WO | WO2019/212955 A1 | 11/2019 |
| WO | WO2019/212956 A1 | 11/2019 |

* cited by examiner

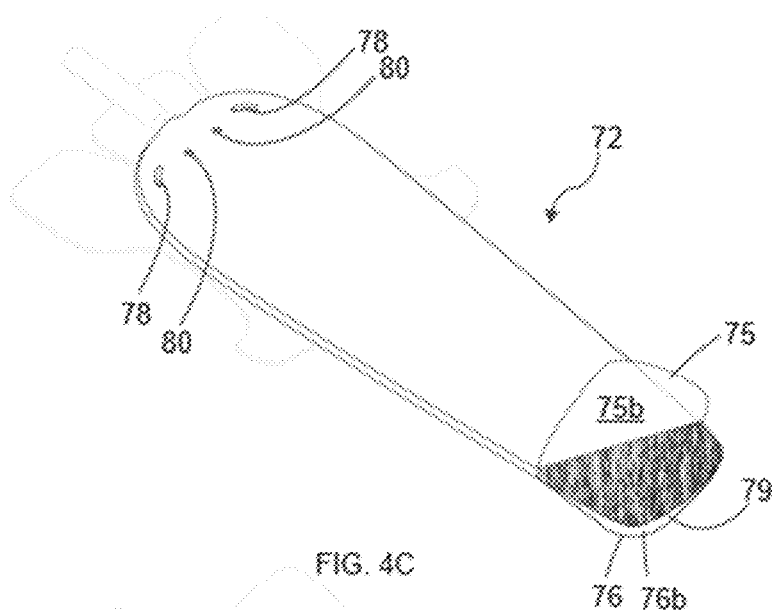
FIG. 4C
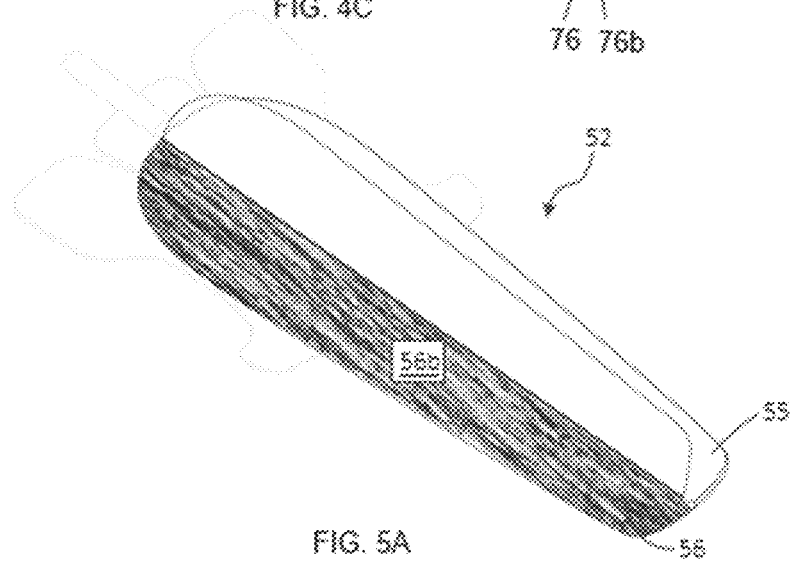
FIG. 5A
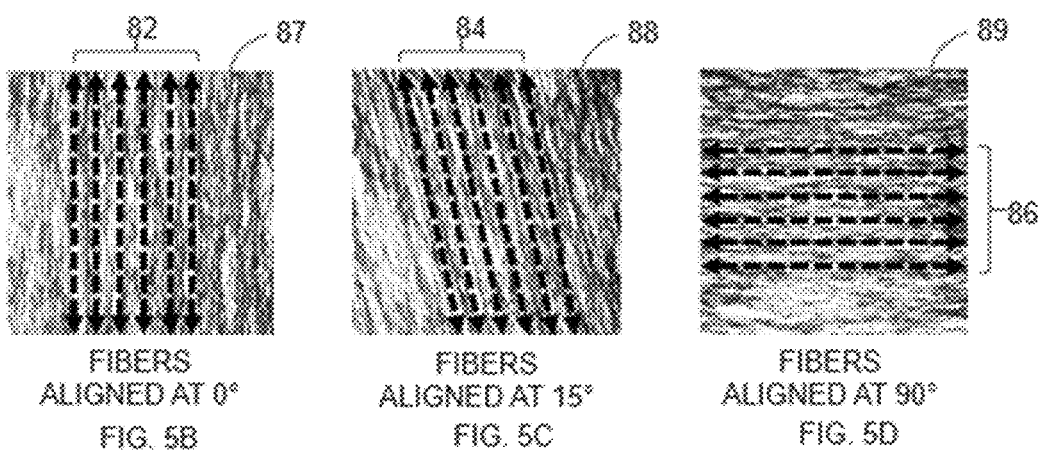
FIBERS ALIGNED AT 0°
FIG. 5B
FIBERS ALIGNED AT 15°
FIG. 5C
FIBERS ALIGNED AT 90°
FIG. 5D

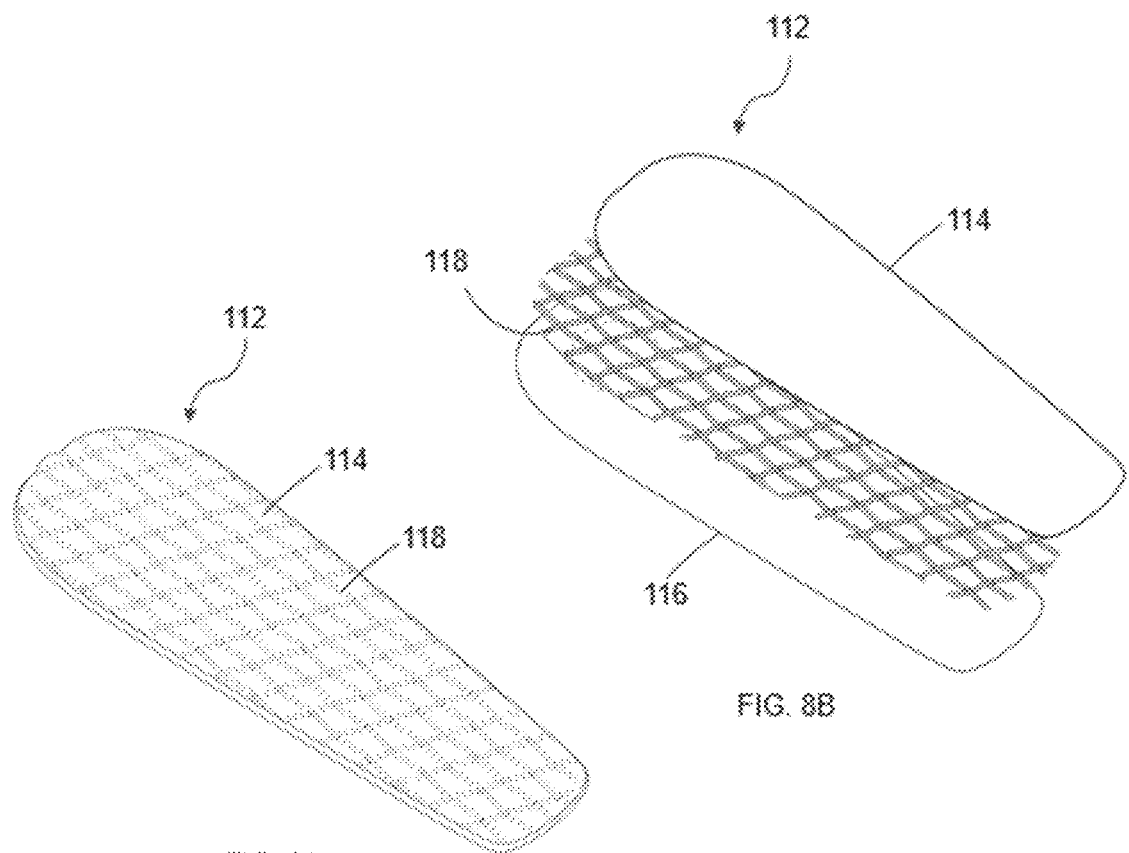
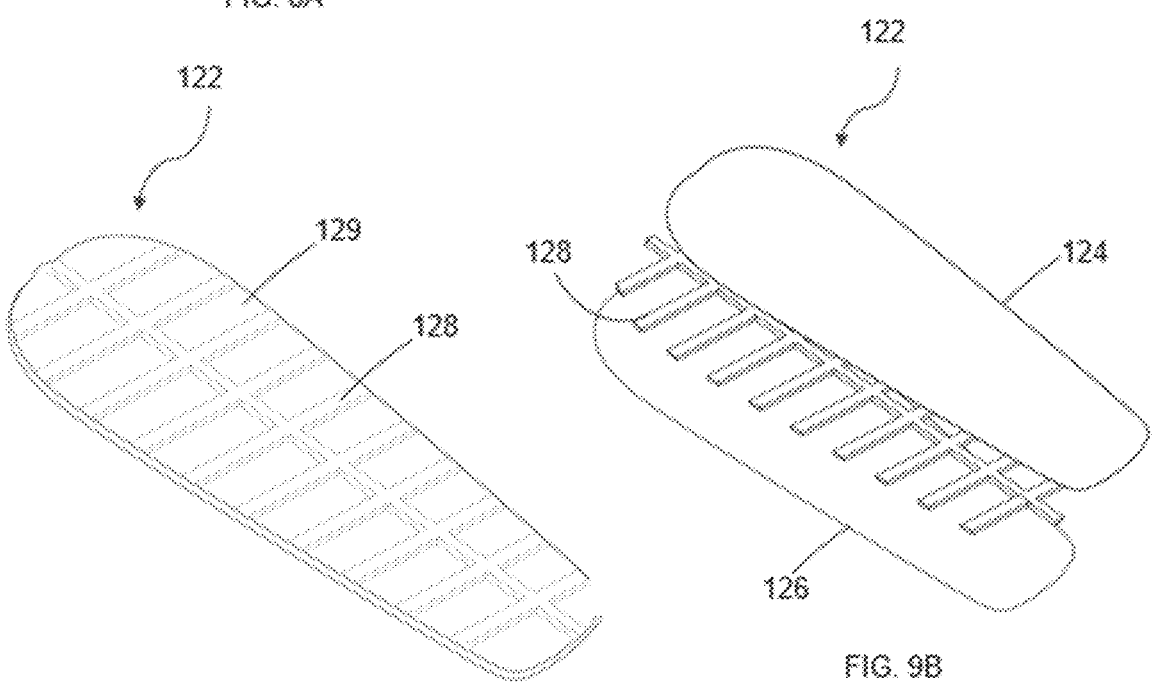

SECTION B-B

FLUID REMOVAL DEVICE

CROSS REFERENCE TO RELATED APPLICATIONS

This application claims the benefit of Indian Patent Application Ser. No. 202011020467, filed May 14, 2020 (DAS Access Code: 9E9E), which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Urine management systems are some of the most commonly used products in a variety of healthcare settings. Though typically associated with urinary incontinence in bedridden patients, the need extends further. For example, patients may require accurate monitoring of urine output for clinicians to evaluate their fluid-levels. Urine management systems may be used to reduce the burden of frequent urination in those who are semi-ambulatory, or they may be used to reduce the risk of wound development by keeping the perineal and sacral skin dry. As the range of clinical needs is broad, all care settings, from an ICU to the home, may incorporate an assortment of urine management products.

One of the most common devices used for urine management in such patients is the indwelling urinary catheter, which may be designed for intermittent or extended use. These devices are low profile latex or silicon tubes inserted through the urethra, all the way into the bladder, where they are anchored using a balloon, to continually drain urine into a collection bag or container. Since the invention of the Foley catheter nearly 100 years ago, the extended use of indwelling catheters has continuously risen, until recently.

Placement of any product into the human body involves risks, especially when the target anatomy is sensitive or sterile. In the case of urinary catheters, the risk of patient harm during insertion and use is significant enough to require trained care providers such as nurses or physicians to perform the insertion, removal, and management of the devices. Even when caution is taken, indwelling catheters can cause significant impairment to urethral tissues during placement. Furthermore, maintaining catheter sterility is difficult. Patients often experience pain and bleeding during insertion and are faced with the possibility of bacteria being introduced into the bladder and renal system. Ultimately, there is a risk of patients developing injuries or urinary tract infections leading to subsequently bladder, kidney, or bloodstream infections.

To reduce these risks and improve clinical outcomes, care providers are transitioning away from indwelling catheters and increasingly using external management systems. These external management systems, especially in men, typically include a collection member to receive urine and an anchoring mechanism, sometimes in the form of an adhesive for securing the collection member in-place. Some of these systems are designed using soft and flexible materials for the collection member and include a drainage tube to remove accumulated fluid. Some external urine management devices used in male patients anchor either on the tip of the penile shaft or along the length of the shaft. In addition to a lack of accommodating anatomical size variations, itchiness, foreign body sensation, or feeling of wetness are some of these systems' shortcomings.

Using soft and flexible materials for the collection member, as well as other components of such a system, such as a drainage tube that may be used in a genital or perineal region, is important for multiple reasons. One reason is that skin and tissues in the genital and perineal regions are more sensitive than other areas of the body, meaning they are often at increased risk of injury. In clinical settings, it is not uncommon for patients to experience skin maceration, dermatitis, and pressure injuries. These complications may be due to tissue swelling exacerbating skin weakness, from improper movement along with extended exposure to moisture, or the use of devices/products in the area that become lodged between the skin and another surface. Furthermore, soft and flexible materials allow patients to move with less discomfort, and more flexible parts allow movement of a part of the product without the adhesive (used to secure the collection member) becoming pulled on or stressed.

Drainage tubes used for these types of devices often have shortcomings such as kinking, which will either significantly decrease or completely block the flow of fluids through the lumen. As these tubes are significantly stiffer than the collection member, such as urine collection bags, the interface between the drainage tubes and the collection member can be another key point of weakness. For example, movement of the drainage tube causes kinking, bending, or twisting of the flexible tube at the connection point, resulting in reduced or blocked fluid flow.

Urine collection systems often irritate the skin and cause discomfort. When a portion of a management device is in contact with the human body, for example, in instances where the adhesive section is coupled to a genital area, the skin exposed to the internal aspect of the enclosed space of the collection section will become moist. Urine received by the collection section will either contact the skin directly or wet at least part of the internal surface of the flexible wall. Though the urine will be drained from the collection section periodically or continually, small amounts of moisture will continue to cling to the surfaces that were exposed to urine. Furthermore, skin (e.g., on the penis) constantly exudes small amounts of moisture via sweat, which over time, will accumulate inside an enclosed area. Either of these mechanisms of moisture introduction can leave liquid droplets in direct contact with the skin and increase the humidity within the enclosed space while potentially weakening the adhesive seal to the skin. This liquid/humidity creates a moist environment known to cause skin maceration, which reduces the structural integrity of the skin and increases the risk for skin damage such as dermatitis and pressure or friction injuries.

Initial stages of maceration are typically identified via a whitened appearance, wrinkling, and minor swelling. It is also known that changes in stratum corneum hydration, dermis hydration, transepidermal water loss (TEWL), skin pH, and skin hardness can be used to evaluate skin integrity. Healthy skin and macerated skin have measurable differences in these physiological markers, as well as more nuanced markers such as erythema index (EI) and white index (WI). Removal of moisture from the collection section and consequently from the skin reduces the risk that these markers deviate from healthy levels.

Currently available collection/protection devices that are external to the body rely on an absorbent material, which is a relic of diapers and pads. The use of the absorbent materials may lead to wetness of the skin, bulkiness, and dislodgement or peeling-off of the device. Retaining absorbed urine may also lead to inefficient suction and reduced air flow. Furthermore, the multitude of components and complex material layups can increase manufacturing complexity and cost.

As such, there is a need for a low-cost urine removal device that enables urine to be conveniently and hygienically removed from the region surrounding a male patient's external genitalia while simultaneously resisting kinking and folding, and that provides a dry internal compartment with little or no pooled or residual urine.

SUMMARY OF THE DISCLOSURE

In some embodiments, a urine removal device comprises a flexible pouch defining an internal compartment, the flexible pouch may have a proximal end and a distal end and an aperture disposed on an external surface, wherein the aperture is capable of receiving at least a part of a penis; at least one suction conduit member may be affixed to the flexible pouch and the suction conduit member may have a conduit shaft including a fluid inlet, a fluid outlet, and a lumen connecting the fluid inlet to the fluid outlet. The fluid inlet may be positioned within the internal compartment of the pouch between the aperture and the distal end. In embodiments, a first part of the conduit shaft is positioned between the aperture and the distal end and at least a second part of the conduit shaft is positioned between the aperture and the proximal end of the pouch.

The urine removal device may be configured such that the conduit shaft terminates within the internal compartment at a position between the aperture and the distal end of the flexible pouch.

In another embodiment, the second part of the conduit shaft extends outside of the internal compartment. Each conduit shaft may be a rigid or partially rigid shaft and may comprise one or more lumens. The urine removal device may have one or more conduit shafts having a first fluid inlet within the internal compartment and a second fluid inlet within the internal compartment, wherein the first fluid inlet and second fluid inlet are positioned on opposite sides of the pouch. The first fluid inlet and the second fluid inlet may be positioned on opposite sides of a longitudinal axis connecting the proximal and distal ends of the pouch. The urine removal device may also comprise a fold resistant feature such as an accordion or bellows pleats on at least one suction conduit member, wherein the fold resistant feature is configured to resist collapse of a lumen defined by the suction conduit member. The fold resistant feature may be located on the section conduit member at a location outside of the internal compartment and it may be located between the distal end of the pouch and the fluid outlet of the suction conduit member.

In embodiments, the urine removal device may have one or more air inlets positioned between the aperture and the proximal end of the pouch and the distance between the first fluid inlet and the second fluid inlet may be greater than the width of the aperture. The conduit shafts may be rigid or partially rigid and configured to form a frame that separates the two opposing inner walls along the longitudinal axis connecting the proximal and distal ends of the pouch.

In some embodiments, the device for collecting and transporting urine comprises a flexible pouch having an aperture configured to receive at least a part of a penis, the flexible pouch having an interior surface defined by at least a first inner surface and an opposing second inner surface at least one suction conduit member affixed to the flexible pouch. The conduit member may include a fluid inlet inside of the pouch near the distal end of the pouch and a fluid outlet outside of the pouch. Furthermore, the pouch may comprise a plurality of flow directors disposed on at least a portion of the first or second inner surface of the pouch such that when the first inner surface and second inner surfaces are drawn together by vacuum suction, channels are created therebetween.

The flow directors may comprise grooves or ridges and the channels may have a depth of less than 1 mm in some embodiments. The grooves may be recessed into the first or second inner surface of the pouch and the flow directors may be substantially oriented parallel to an axis connecting the proximal end and the distal end of the pouch. At interior of the pouch may be non-absorbent and with enhanced hydrophobic properties. In some embodiments, the aperture is located on a first wall and the opposing wall includes at least one pleat oriented substantially parallel to a longitudinal axis connecting the proximal end to the distal end of the pouch.

In some embodiments, the device for transporting urine comprises a flexible pouch having a first wall and an opposing second wall and an aperture through the first wall. The aperture may be configured to receive at least a part of a penis. The device may include a frame having a distal end inside of the pouch distal to the aperture and a proximal end outside of the pouch proximal to the proximal end of the pouch. The frame may comprise a lumen capable of transporting fluid from the inside of the pouch to the outside of the pouch when a vacuum is applied to the lumen.

In some embodiments, the frame provides a structural support such that the bending stiffness of the overall device is substantially the same as the bending stiffness of the structural support alone. The frame may comprise two distal elongate members having a pair of openings at the distal end of the pouch, wherein the distal elongate members converge to one proximal member at its proximal end. The distal elongate members may be disposed at opposing sides of the pouch and they may be attached to the pouch. The structural support may include a flexible joint proximal to the pouch to at least partially isolate the pouch from motion of the proximal end of the structural support to reduce tugging on the pouch and kinking near the interface between the pouch and the structural support. The joint is a bellows section in some embodiments. An adhesive patch may be attached to the flexible pouch and configured for fastening the flexible pouch to the patient's suprapubic region. The adhesive patch may comprise a substrate having adhesive applied to at least one surface. In some embodiments, the substrate is segmented into a plurality of interconnected tabs by one or more notches formed on the substrate and the interconnected tabs are not attached to the pouch.

For example, described herein are urine removal devices comprising: a flexible pouch having a front formed of first sheet and a back formed of second sheet, wherein the first sheet and the second sheet are joined together at the periphery of the pouch; an aperture through the back of the pouch, the aperture opening into an internal compartment within the pouch, wherein the aperture is configured to receive at least a part of a penis; a suction conduit member extending from a proximal end region of the pouch, the suction conduit member comprising a first conduit shaft extending along a right side of the periphery of the internal compartment of the pouch and ending in a first fluid inlet at a distal end region of the right side of the pouch, and a second conduit shaft extending along a left side of the periphery of the internal compartment of the pouch and ending in a second fluid inlet at a distal end region of the left side of the pouch, wherein the suction conduit member has a stiffness that prevents the first sheet and the second sheet from wrinkling or folding in an axis transverse to a distal-to-proximal axis; and a flow directing spacer extending from the proximal end region to the distal end region within the internal compartment of the pouch, wherein the flow directing spacer provides channels from the proximal end region to the distal end region within the internal compartment when suction is applied within the internal compartment from the suction conduit member.

The flow directing spacer may include a layer of polymeric fibers forming a plurality of channels. A majority (e.g., >50%, >55%, >60%, >65%, >70%, >75%, >80%, etc.) of the plurality of channels may be oriented in a substantially proximal to distal direction.

The flow directing spacer may include a hydrophobic non-wicking material. The flow directing spacer may comprises an array of fibers attached to the first sheet, the second sheet, or both the first and second sheet.

The suction conduit member may extend outside of the proximal end of the internal compartment and ends beyond the proximal end region of the pouch.

In any of these devices, each conduit shaft may be a rigid or partially rigid shaft. The conduit shaft may act as a support frame. For example, in any of these devices, the first and second conduit shafts may form a frame that separates two opposing inner walls of the pouch.

The first sheet and the second sheet may be formed of a polymeric material having a thickness 1 mm or less, and wherein the first conduit shaft and the second conduit shaft have an internal diameter of 0.5 mm or greater.

Any of these devices may include one or more longitudinal folds in the first sheet extending from the proximal end region to the distal end region.

The conduit member may include a flexible joint proximal to the pouch to at least partially isolate the pouch from motion of a suction source tube.

The distance between the first fluid inlet and the second fluid inlet may be greater than a width of the aperture.

The flow directing spacer may includes grooves, ridges or grooves and ridges having a channel depth of 1 mm or less.

Any of these devices may include a second flow directing spacer within the internal compartment.

Any of these device may include an adhesive patch attached to the flexible pouch, the adhesive patch configured for fastening the flexible pouch to a patient's suprapubic region.

For example, described herein are urine removal device comprising: a flexible pouch having a front formed of first sheet and a back formed of second sheet, wherein the first sheet and the second sheet are sealed together; an aperture through the back of the pouch, the aperture opening into an internal compartment within the pouch, wherein the aperture is configured to receive at least a part of a penis; a suction conduit member extending from a proximal end region of the pouch, the suction conduit member comprising at least one conduit shaft extending along the internal compartment of the pouch and ending in a fluid inlet at a distal end region of the receptacle, wherein the suction conduit member has a stiffness that prevents the first sheet and the second sheet from wrinkling or folding; a flow directing spacer extending within the internal compartment of the pouch, wherein the flow directing spacer provides channels from the proximal end region to the distal end region within the internal compartment when suction is applied within the internal compartment from the suction conduit member; and an adhesive patch attached to the flexible receptacle, the adhesive patch configured for fastening said flexible receptacle to the patient's suprapubic region.

As mentioned, the flow directing spacer may comprise a layer of polymeric fibers forming a plurality of channels. The majority (e.g., >50%, >55%, >60%, >65%, >70%, >75%, etc.) of the plurality of channels may be oriented in a substantially proximal to distal direction. The flow directing spacer may comprise a hydrophobic non-wicking material. The flow directing spacer may comprise an array of fibers attached to the first sheet, the second sheet, or both the first and second sheet.

The suction conduit member may extend outside of the internal compartment and ends beyond the proximal end region of the pouch. The conduit member may include a flexible joint proximal to the pouch to at least partially isolate the pouch from motion of a suction source tube. The first and second conduit shafts may form a frame that separates two opposing inner walls of the pouch.

Any of these devices may also include one or more longitudinal folds in the first sheet extending from the proximal end region to the distal end region.

The distance between the first fluid inlet and the second fluid inlet may be greater than a width of the aperture.

The flow directing spacer may include grooves, ridges or grooves and ridges having a channel depth of 1 mm or less.

For example, a urine removal device may include: a flexible pouch having a front formed of a first sheet of liquid-impermeable material and a back formed of second sheet of liquid-impermeable material, wherein the first sheet and the second sheet are sealed together at a periphery of the pouch; an aperture through the back of the pouch, the aperture opening into an internal compartment within the pouch, wherein the aperture is configured to receive at least a part of a penis; a suction conduit member extending from a proximal end region of the pouch, the suction conduit member forming a frame comprising a first conduit shaft extending along a right side of the periphery of the internal compartment of the pouch and ending in a fluid inlet at a distal end region of the right side of the pouch, and a second conduit shaft extending along a left side of the periphery of the internal compartment of the pouch and ending in a second fluid inlet at a distal end region of the left side of the pouch, wherein the frame prevents the first sheet and the second sheet from wrinkling or folding in an axis transverse to a distal-to-proximal axis of the device; and a flow directing spacer layer extending within the internal compartment of the pouch, wherein the flow directing spacer layer provides channels from the proximal end region to the distal end region within the internal compartment when suction is applied within the internal compartment from the suction conduit member.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 4C illustrates a perspective view of a urine removal device having flow directors on the middle wall according to an example embodiment.

FIG. 5A illustrates a perspective view of a pouch having oriented flow directors on an inner surface according to an example embodiment.

FIGS. 5B, 5C, and 5D illustrate fibers oriented on a surface at angles of 0 deg., 15 deg., and 90 deg, respectively.

FIGS. 8A and 8B illustrate a perspective view and an exploded view, respectively of a pouch having flow directors according to an example embodiment.

FIGS. 9A and 9B illustrate a perspective view and an exploded view, respectively of a pouch having flow directors according to an example embodiment.

DETAILED DESCRIPTION

Figure 1A:
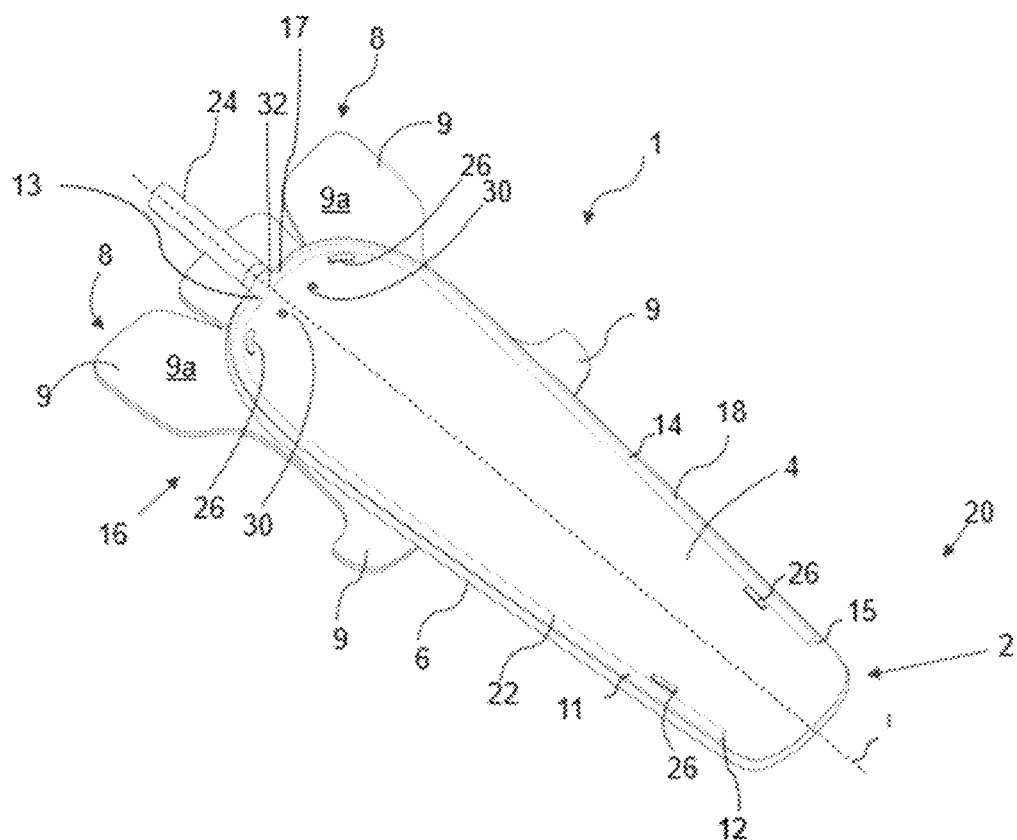
FIGS. 1A and 1B, illustrate a perspective view and an exploded view of an example embodiment of a urine removal device.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

The embodiments disclosed herein provide urine removal devices that are suction-assisted, and enable urine to be conveniently and hygienically removed from the region surrounding a male patient's external genitalia area.

For the purposes of this disclosure, the term "proximal" and "distal" are used with reference to the length of the urine removal device or the length of a pouch that forms part of the urine removal device; that is, "proximal" denotes the first end of the device or pouch toward the suprapubic region beyond where it engages with (or is positioned in the vicinity of) the base of the penis and "distal" denotes the opposed second end of the device or pouch toward the end where it resides between the legs of the patient. For the purposes of this disclosure, the terms "top" and "bottom" are used with reference to upper and lower surfaces of the urine removal device or components thereof. That is, "top" denotes a surface or direction that is coincident with or in the direction of the upper surface of the penis. In contrast, "bottom" denotes a surface or direction that is coincident with or in the direction of the underside of the penis.

This disclosure describes urine removal devices that enable urine discharged from a male patient's penis to be contained within a flexible pouch and drawn out of the pouch and away from the genital region of the patient by application of suction or negative pressure. The various embodiments comprise a pouch having an aperture sized to permit a male patient's penis. The pouch may be formed of one or more fluid-tight (liquid-impermeable) materials (for example, polyvinyl chloride, polypropylene, polyethylene, low-density polyethylene, high-density polyethylene, ethylene-vinyl acetate, polyvinylidene dichloride, biaxially oriented polypropylene, ethylene vinyl alcohol, natural rubber latex, silicon rubber, polyurethane, coated synthetic or natural fabric, etc.) wherein the fluid-tight materials define an internal compartment. The fluid-tight materials form one or more external surfaces and internal surfaces for the pouch. The aperture may be fixedly or adaptably sized to enable a male patient's penis to be inserted therethrough and to be positioned within the internal compartment. Additionally, the pouch and aperture are configured such that upon insertion of the patient's penis, at least a part of the penis (for example, at least the tip of the penis or the meatus) and optionally, substantially the whole of the penis, is housed within the pouch in the region between the aperture and the distal end of the pouch.

The urine removal device may include one or more fasteners or anchors that enable the penis to remain housed within the pouch unless intentionally removed (or removed by application of force).

In addition, the urine removal device also includes one or more suction conduit members. Each of the one or more suction conduit members comprise a conduit shaft having one or more fluid inlets, one or more fluid outlets, and a lumen connecting each of the inlet(s) and outlet(s). The one or more fluid inlets of the suction conduit member(s) are positioned within or in fluid communication with the internal compartment of the pouch. The one or more fluid outlets of the suction conduit are configured for direct or indirect coupling with a suction source (for example, a vacuum supply). The one or more fluid inlets, one or more fluid outlets and lumen(s) connecting the two, together define one or more fluid passageways between the internal compartment and the one or more fluid outlet(s) (or a receptacle to which the one or more fluid outlet(s) are connected).

In some embodiments, the one or more such conduit members are configured such that (i) the one or more fluid inlet (s) are positioned within or in fluid communication with the internal compartment of the pouch, between the aperture and the distal end of the pouch, and (ii) at least a first part of the conduit shaft is positioned between the aperture and the distal end of the pouch, and at least a second part of the conduit shaft is positioned between the aperture and the proximal end of the pouch. In an embodiment, a first end of the conduit shaft may terminate within the internal compartment of the pouch, at a position between the aperture and the distal end of the pouch. In an embodiment, a second part of the conduit shaft may extend out of the pouch and may terminate at a position either between the aperture and the proximal end of the pouch or may terminate at a position beyond the proximal end of the pouch in a direction that is opposed to the distal end of the pouch.

In an embodiment, the conduit shaft of the one or more conduit members may comprise a rigid, partially rigid, or partially flexible conduit shaft and may be positioned within or affixed to the pouch in a manner that provides a rigid or semi-rigid frame that reinforces the pouch.

In an embodiment, the one or more conduit members may be configured to provide at least a first and a second fluid inlet within the pouch (or within the internal compartment of the pouch), wherein the first and second inlets are positioned on opposite sides of pouch (or of the internal compartment of the pouch). In an embodiment, the first and second inlets are respectively positioned on opposite sides of a longitudinal axis connecting the proximal end and the distal end of the pouch (or of the internal compartment of the pouch).

In one or more embodiments, one or more of the conduit members are provided with an occlusion resistant feature or an anti-kinking feature, comprising one or more accordion pleats or bellows folds at one or more regions of the conduit members. The accordion pleats or bellows folds enable the conduit members to resist being kinked, twisted, folded, or collapsed, which maintains the patency of the lumen defined between the fluid inlet(s) and fluid outlet(s) of the conduit member(s) and prevents blockage of the fluid passageway between the fluid inlet(s) and fluid outlet(s). In an embodiment, the occlusion resistant feature or anti-kinking feature may be on the one or more on the conduit shaft(s) of the conduit members at a location outside of the internal compartment of the pouch and may be located between the distal end of the pouch and a fluid outlet of the conduit member.

The pouch is additionally provided with one or more air inlets (other than the aperture) that enable air to be drawn into the pouch. In an embodiment, the one or more air inlets are positioned relatively closer to the proximal end of the pouch and relatively further from the distal end of the pouch. In a specific embodiment, the one or more air inlets are positioned between the aperture and the proximal end of the pouch.

When the urine removal device is disposed on a subject's penis (i.e., when at least some of the penis is housed within the internal compartment of the pouch), urine released from the meatus flows into the pouch and is drawn (by the application of suction) into the fluid inlet(s) and through the lumen(s) connecting the fluid inlet(s) and the one or more fluid outlet(s) of the conduit member(s), and out of the one or more fluid outlet(s) (for example into a receptacle to which the one or more fluid outlet(s) are connected). As a result of the application of suction through the conduit member(s), urine released or pooled into the pouch is readily and hygienically removed from the pouch and the vicinity of the patient's penis. Additionally, as a result of the application of suction through the conduit member(s), negative pressure is created within the pouch, and air is drawn into the pouch through the one or more air inlets for as long as suction is applied. The air flow thus generated additionally serves to draw urine away from the tip of the penis and in the direction of the fluid inlet(s). Maintaining the suction and consequent air flow results in urine within the pouch being quickly drawn out and resultant dehumidification/drying of the pouch.

Additionally, in the configuration where the one or more conduit members are configured to provide at least a first and a second fluid inlet within the pouch, and the first and second inlets are respectively positioned on opposite sides of a longitudinal axis connecting the proximal end and the distal end of the pouch, it has been found that the urine removal device proves to work while tilted. When a patient is lying on a side, the pouch tends to be aligned such that one side is higher than an opposite side, and as a result, urine released from the penis will pool on or at the lower internal side wall. Having multiple fluid inlets distributed on opposite sides of the longitudinal axis ensures that, regardless of which side of the pouch is positioned lower, there is at least one fluid inlet that is in the vicinity of the pooling urine and through which the urine can be drawn out of the pouch.

In an embodiment, the distance between the first and second fluid inlets positioned on opposite sides of the longitudinal axis is greater than the diameter or width of the aperture provided on the pouch. In another embodiment, the distance between the first and second fluid inlets positioned on opposite sides of the longitudinal axis is greater than (i) a maximum width of the aperture in a direction perpendicular to a longitudinal axis connecting the proximal end and distal end of the pouch, or (ii) the maximum width of the aperture (as measured on an axis that is perpendicular to the longitudinal axis and that passes through the aperture).

Specific embodiments of the invention are now described in connection with the accompanying figures in which like reference characters refer to the same parts throughout the different views. The drawings are not necessarily to scale, emphasis instead being placed upon illustrating embodiments of the present invention.

Figure 1B:
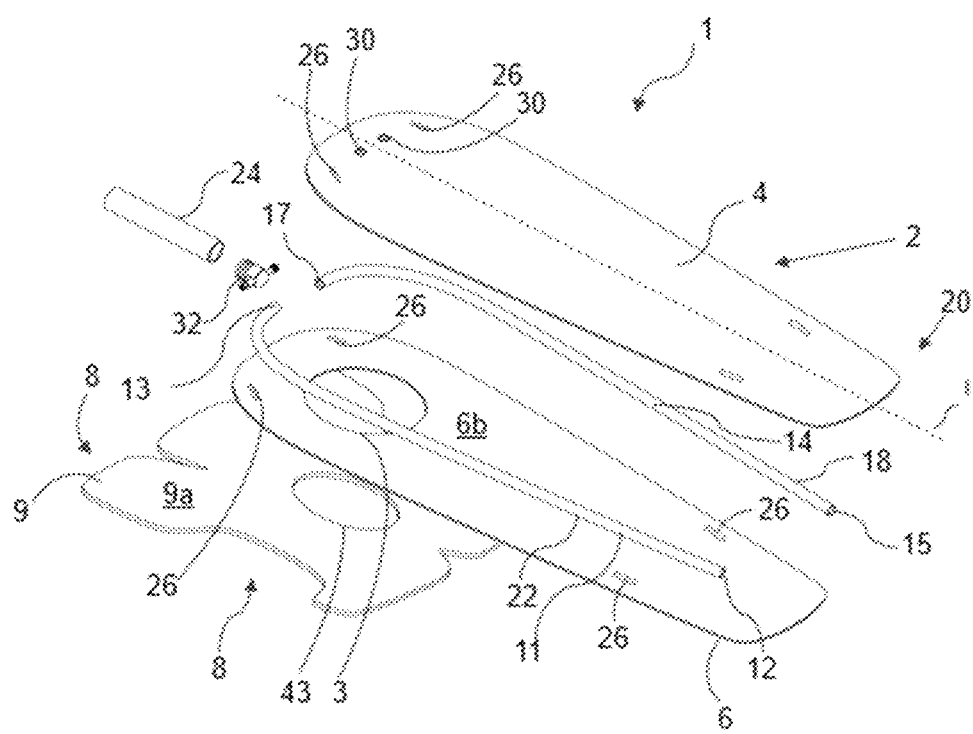
Figure 1C:
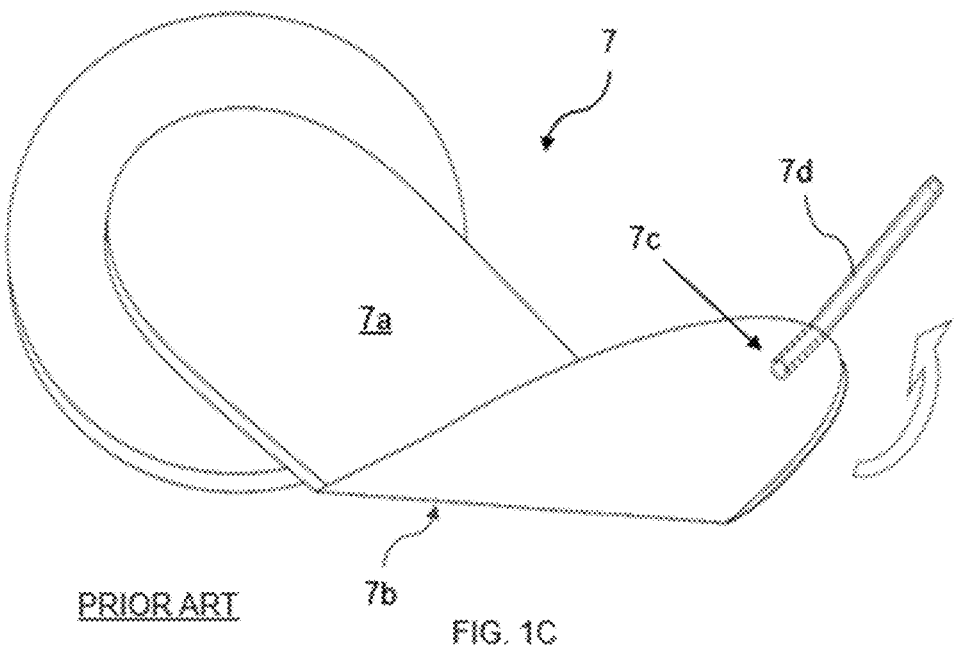
FIGS. 1C and 1D illustrate prior art urine removal devices in various configurations.

Referring to FIG. 1A-1D, a urine removal device 1 is shown according to an example embodiment. FIG. 1A shows a perspective view of the device 1 and FIG. 1B shows another perspective view of the device 1 exploded to show the interaction of the components more clearly, while FIG. 1C provides a perspective view from which a cross-sectional view (FIG. 1D) is taken to illustrate the interaction of the pouch walls with the conduit members.

The device 1, as shown in FIG. 1A, includes a pouch 2 having a first wall 4 and a second wall 6. It would be understood that in other embodiments, the pouch 2 may equally be formed of a single continuous side wall having two opposite surfaces, where one of the two opposite surfaces forms an external sidewall and the other of the two opposite surfaces forms an internal sidewall. The second wall 6 or first wall 4 may have air ports 30 to allow ambient air to be drawn into the pouch 2 to facilitate air flow through the pouch. In the illustrated embodiment, the second wall 6 and first wall 4 are attached to each other at least around most of their periphery such that they form an internal compartment between them for housing the penis and the urine that it discharges. One or more conduit members may be at least partially located within the pouch 2 to facilitate the transfer of urine out of the pouch. For example, FIG. 1A shows a first conduit member 18 and a second conduit member 22 as hidden lines, extending from the proximal end 16 of the pouch 2 to near the distal end 20. While the Figures illustrate conduit members 18 and 22 as two separate members, in certain embodiments, the two could be integrated within a single shaped conduit member (for example, a u-shaped, c-shaped, v-shaped, or wishbone-shaped conduit member having two ends each lying on opposite sides of a longitudinal axis that connects the proximal and distal ends of the pouch 2. As shown in the Figures, each of conduit members 18 and 22 respectively comprise a conduit shaft 14 and 11, respectively, having fluid inlet openings 15 and 12 and fluid outlet openings 17 and 13, wherein each conduit shaft 14 and 11 defines an internal lumen connecting the respective fluid inlet openings 15, 12 and fluid outlet openings 17 and 13 such that fluid can be drawn from fluid inlet openings 15, 12 through the internal lumen of the conduit member 18 and 22 and out of fluid outlet openings 17 and 13.

As illustrated in FIGS. 1A to 1C, the one or more such conduit members may be configured such that (i) the one or more fluid inlets 15 and 12 are positioned within the internal compartment of the pouch 2, between the aperture 3 and the distal end 20 of the pouch, and (ii) at least a first part of the conduit shaft(s) 14 and 11 is positioned between the aperture 3 and the distal end 20 of the pouch 2, and at least a second part of the conduit shaft(s) 14 and 11 is positioned between the aperture 3 and the proximal end 16 of the pouch 2. In an embodiment, a first end of the conduit shaft(s) 14 and 11 may terminate within the internal compartment of the pouch 2, at a position between the aperture 3 and the distal end 20 of the pouch 2. In an embodiment, a second end of the conduit shaft(s) 14 and 11 may extend out of the pouch 2 and may terminate at a position either between the aperture 3 and the proximal end 16 of the pouch 2, or may terminate at a position beyond the proximal end 16 of the pouch 2 in a direction that is opposed to the distal end 20 of the pouch 2. As further described below, where the conduit shaft(s) terminate, they may be in fluid communication with the outside of the pouch 2 through another conduit (e.g., suction source tube 24).

The suction source tube 24 may reside at the proximal end 16 of the pouch 2 for connecting to a vacuum supply. The suction source tube 24 connects to the fluid outlet openings 17 and 13 of the first conduit member 18 and the second conduit member 22 to draw fluid (urine) from the distal portion 20 of the pouch 2 and out of the pouch 2 so that the interior internal compartment may be kept relatively dry and to prevent urine stasis and pooling. A fastener or anchor such as an adhesive patch 8 may be attached to an external surface of the second wall 6 to secure the pouch 2 to the patient's penis, abdomen, scrotum, or suprapubic region. The adhesive patch 8 may be a single layer, or it may be comprised of several layers, as described in more detail below.

The device 1 is shown in an exploded view in FIG. 1B to further illustrate the relationship of the components and features. The first and second conduit members 18 and 22 (or more specifically, the first and second fluid outlets 17 and 13) may connect to an adapter 32, which connects both conduit members 18 and 22 to the suction source tube 24. One skilled in the art would recognize that adapter 32 may be a variety of devices to serve the purpose of connecting multiple tubes to one or more outlets; examples include a Y-connector, T-connector, or a manifold. Alternatively, the first and second conduit members 18 and 22 may be made integral to the suction source tube 24 so that a connector is not required. The conduit members 18 and 22, the adapter 32, and the distal end of the suction source tube 24 are located between the first wall 4 and second wall 6 and may be retained by one or more conduit member retainers 26 (shown as hidden lines in FIG. 1A and further described below).

The one or more conduit members 18 and 22 may comprise conduit shafts 14 and 11 that may be rigid, partially rigid, or partially flexible, and are positioned within, or affixed, to the pouch 2 in a manner that provides a rigid or semi-rigid frame to stiffen the device 1. Furthermore, in embodiments, the frame optionally separates opposing walls 4 and 6 of the pouch 2 from each other. The frame formed by the one or more conduit members 18 and 22 enables the pouch 2 to resist deformation or kinking in a manner that could occlude fluid flow between regions of the pouch 2. The structural frame may also include the suction source tube 24 and the adapter 32 that connects the suction source tube 24 to the conduit members 18 and 22. In this sense, the structural frame extends from within the pouch 2 to outside of the pouch so that the stiffness of the device 1 is increased, which may reduce deformation of the pouch that may lead to a vacuum lock as described below.

Figure 1D:
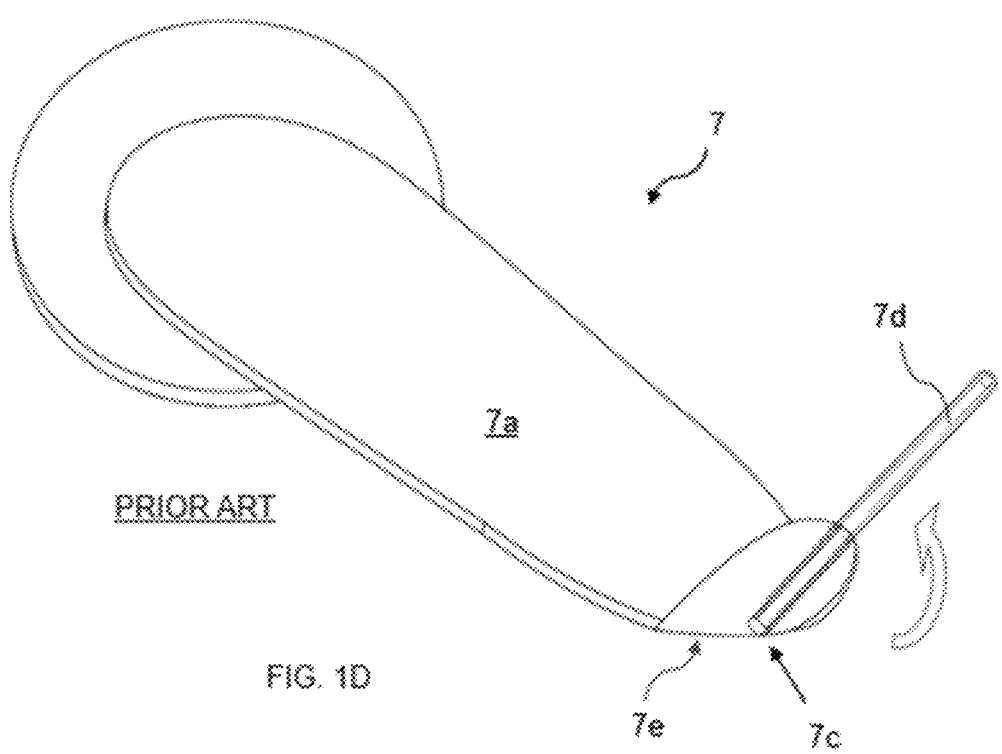

There are instances where the pouch may deform in such a way that prevents suction to be effective throughout the pouch. For example, a pouch 7 in a deformed state is illustrated in FIG. 1C where a bend 7b in the pouch 7a of the device 7 results in a vacuum lock or occlusion of fluid flow because the inlet 7c to the suction conduit 7d is distal to the bend 7b; this arrangement may result in totally or partially isolating the upper portion of the pouch 7a from the applied suction. In another example, FIG. 1D shows the device 7 having a bend 7e near an end of the pouch 7a wherein the inlet 7c of the suction conduit 7d butts up against the pouch 7a and becomes occluded, which results in a decrease in fluid flow to the suction tube. This may happen, for example, when a patient or operator moves the suction conduit 7d or any longer tubing attached to it—the motion may locally fold the bag and block the inlet 7c, thus reducing suction. A wrinkled pouch may lead to a decrease in fluid flow or in creation of isolated compartments within the pouch that may not be exposed to suction. In the absence of any spacing features, the internal walls of the pouch may cling together due to application of negative pressure from the suction conduit within the pouch resulting in a vacuum lock or occlusion of fluid flow or in the creation of isolated compartments within the pouch. Similar to FIG. 1D, the inlet of the suction conduit may become occluded by the pouch when it collapses due to vacuum. These problems may be mitigated by the structural support provided by the conduits or other flow directing features described in embodiments disclosed herein. For example, having a structural support that spans from within the pouch 2 to the outside of the pouch, as shown in FIGS. 1A-1B (among others) prevents kinking where the suction source tube 24 meets the pouch 2, thus preventing the deformation illustrated in FIG. 1D.

Figure 1E:
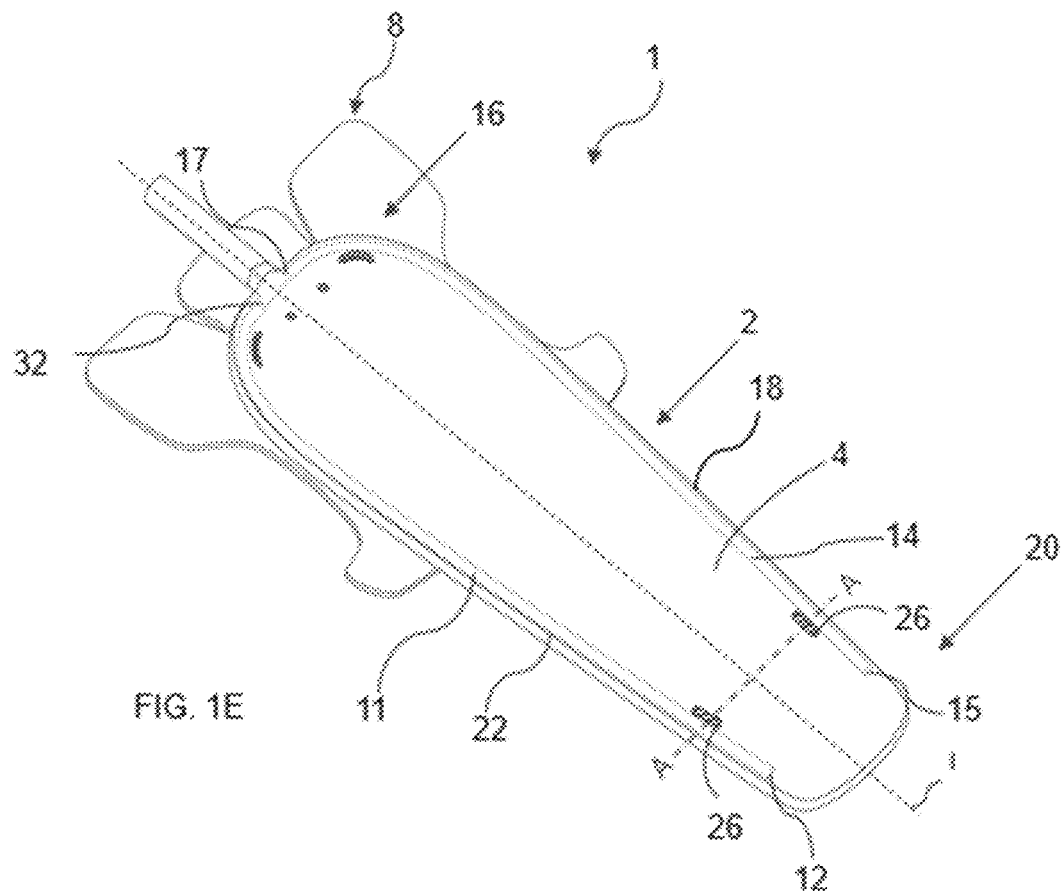
FIGS. 1E and 1F illustrate a perspective view and a sectional view of the device in FIGS. 1A and 1B.
Figure 1F:
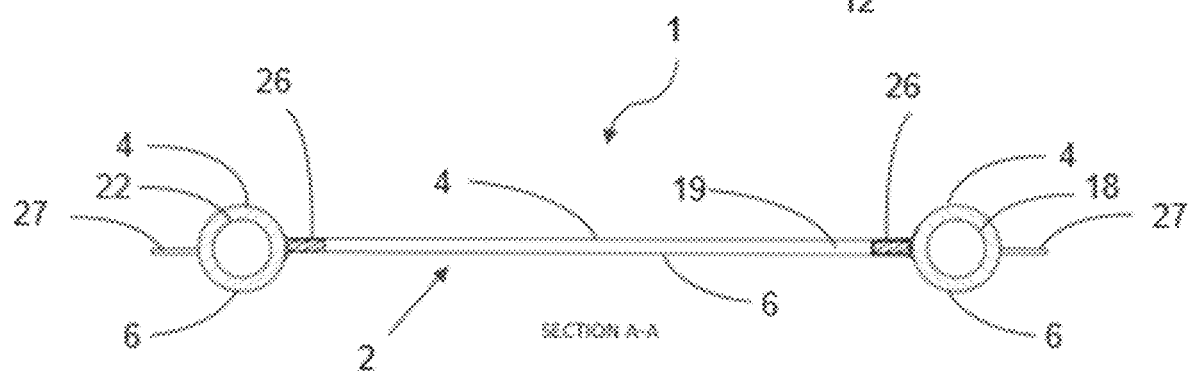

Now with reference to FIGS. 1E and 1F, the pouch 2 may have one or more conduit member retainers 26 to hold the conduit members 18 and 22 in place. The conduit member retainers 26 may be created by joining the first wall 4 to the second wall 6 or by joining the conduit with first wall 4 or the second wall 6 (or both) in discrete or continuous spots or lines next to each conduit member 18 and 22 to create a barrier that constrains the conduit member(s). One skilled in the art will recognize that there are many other alternative methods to create the barrier, such as bonding a small spacer between the walls adjacent to the conduit members, or forming one or both walls in a manner to create a feature protruding into the space between the walls deep enough to retain the conduit members. The second wall 6 and first wall 4 may be joined by any method for connecting polymers such as, for example, bonding with an adhesive, solvent bonding, or heat staking (thermal bonding). In other embodiments, the conduit members may be directly joined to the first wall 4 or the second wall 6, or both, using a suitable joining process. In some embodiments, the conduit members may be located external to the pouch except at the distal tip of each conduit member where they enter the pouch or be in fluid communication with the pouch to provide suction in the distal portion of the pouch. The conduit member retainers 26 hold conduit members in place against the pouch 2 to prevent the undesired movement of the pouch walls causing the pouch 2 to assume a folded or kinked configuration, resulting in occlusion of the fluid inlet openings 15 and 12 of the conduit members 18 and 22 or in blockage of a fluid flow path between a region in which urine has accumulated within pouch 2 and one or more of the fluid inlet openings 15 and 12.

Figure 1G:
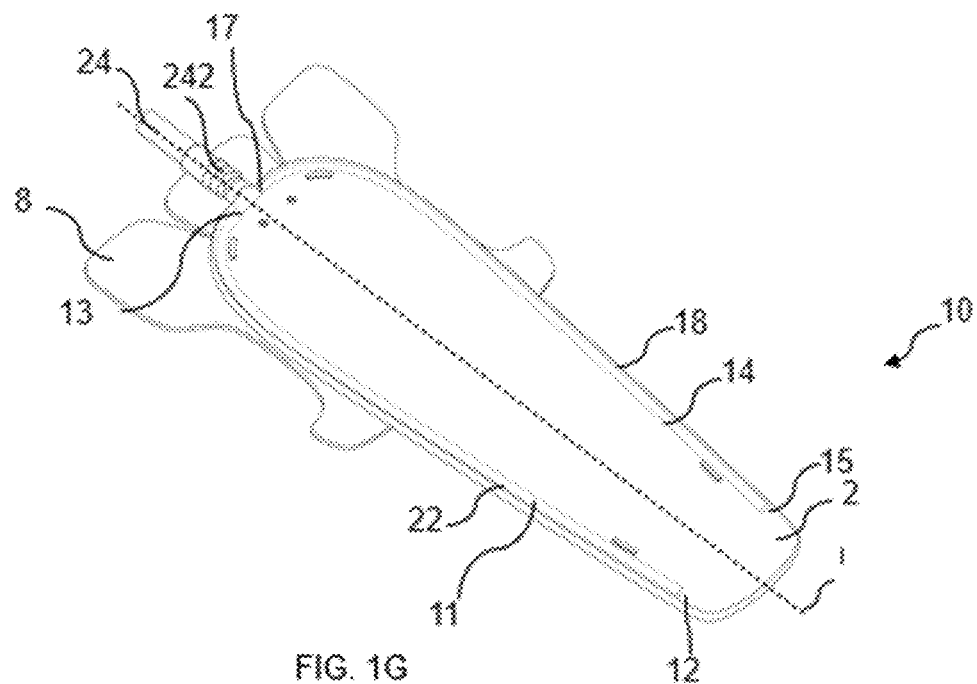
FIGS. 1G and 1H, illustrate a perspective view and an exploded view of an example embodiment of a urine removal device.
Figure 1H:
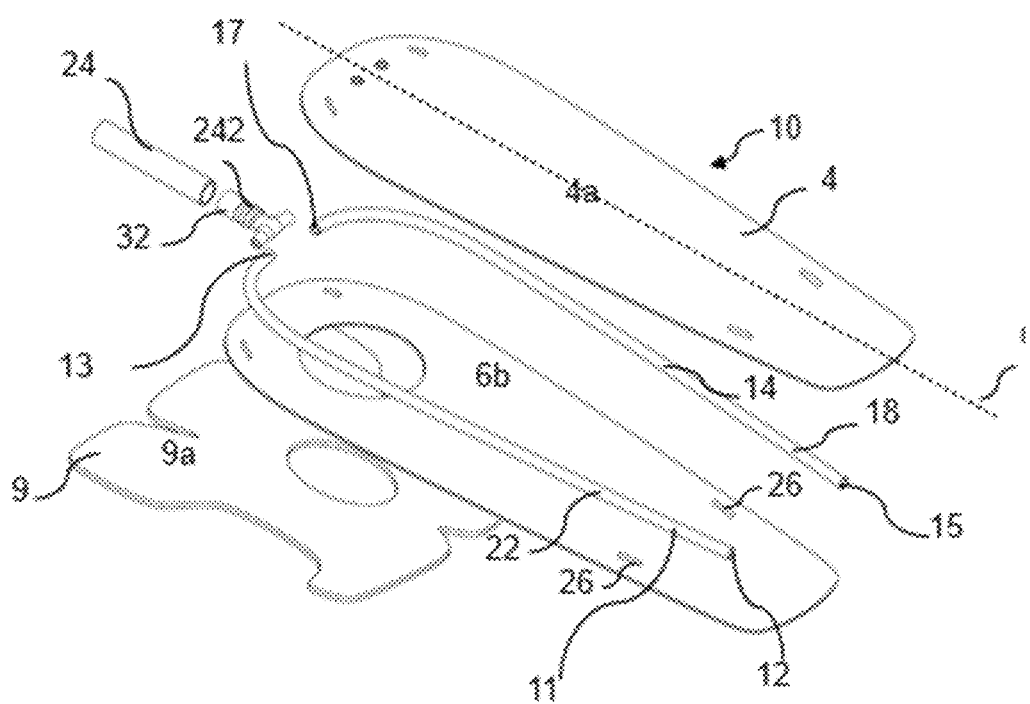

As shown in the device 10 of FIGS. 1G and 1H, an occlusion resistant feature or an anti-kinking feature may be provided on suction source tube 24, or for that matter on any one or more of the conduit members 18 and 22, to enable the suction source tube 24 or any of conduit members 18 and 22 to resist being kinked, twisted, folded or collapsed, thus maintaining the patency of the lumen defined between the fluid inlet(s) and fluid outlet(s) of the conduit member(s) which prevents blockage of the fluid passageway between the fluid inlet(s) and fluid outlet(s). As shown in FIGS. 1G and 1H, the anti-kinking feature may comprise a conduit segment (or a tube segment) 242 comprising one or more accordion pleats or bellows folds. The pleated or folded conduit segment 242 enables the suction source tube 24 or any of conduit members 18 and 22 on which it is provided to resist being kinked, twisted, folded, or collapsed. In an embodiment, the conduit segment 242 is provided either (i) at a junction between suction source tube 24 and conduit members 18 and 22, or (ii) proximal to the junction between suction source tube 24 and conduit members 18 and 22, toward the suction source. In an embodiment, the anti-kinking feature may be provided at a location outside of the pouch 2 and may be located between the distal end of the pouch 2 and a fluid outlet of the suction source tube 24.

One skilled in the art will recognize that there are many implementations of a conduit member that serve to provide access to the inside of the pouch. For example, in some embodiments, the conduit member or channel may be integral to the pouch so that the stiffness of the joint formed by the conduit member and the pouch is matched to prevent a pinch point where a tube, being stiffer, may otherwise crease at the relatively more flexible pouch. In other embodiments, the pouch may be reinforced in the area where the conduit members 18 and 22 or suction source tube 24 attaches, or the suction source tube 24 may protrude far enough into the pouch to reduce the likelihood of a pinch point at the joint.

Further considering FIG. 1B, the adhesive patch 8 may be comprised of single or multiple layers and includes a substrate layer 9 having an outer surface 9a, which is attached to an external surface of second wall 6 of the pouch 2. The inner surface 6b of the second wall 6 may be bare, as shown, or it may have an attached or integrated laminate or a surface treatment or a surface texture to accentuate urine flow towards the distal end 20 of the pouch 2 as described below. Likewise, the inner surface (not shown) of the first wall 4 may have a laminate attached, or it may have a surface treatment or a surface texture to improve fluid flow. The second wall 6 of the pouch 2 has an aperture 3 that approximately aligns with an aperture 43 in the adhesive patch 8. The aperture 3 and the aperture 43 provide access for the penis to enter into the pouch 2. The inner surfaces 6b and 4b (not shown) of respective second wall 6 and first wall 4 may have coatings or features to direct air and liquid flow, as described in more detail below, or may be bare or untreated as shown. In a particular embodiment, fluid inlet openings 15 and 12 are positioned within the same internal compartment within which the penis discharges urine, without any intermediate layer separating said fluid inlet openings 15 and 12 from the internal compartment.

FIG. 1F illustrates the interface between the conduit members and the pouch walls in an embodiment; the cross-section A-A taken from FIG. 1E is made through the conduit member retainers 26 to illustrate how the tubes are captured. With reference to the cross-sectional view A-A, the first conduit member 18 is enveloped on one side by the first wall 4 and on the opposite side by the first wall 4, and the second wall 6 and the first wall 4 are joined on each side of the conduit member 18. The conduit member retainer 26 represents the location where the second wall 6 and first wall 4 are joined adjacent to the conduit member 18, and the pouch seam 27 is where the first wall 4 and second wall 6 are joined outside of the conduit member 18. Thus, the conduit member 18 is captive such that it stays in the location generally adjacent to the pouch seam 27, which adds stability and stiffness to the device 1, as discussed in further detail below. The same arrangement exists on the opposite side with respect to the second conduit member 22. In between the conduit member retainers 26, the first wall 4 and second wall 6 are predominantly not attached so that they form the interior internal compartment 19 of the pouch 2.

As illustrated in FIGS. 1E to 1F, the conduit members 18 and 22 may be configured to provide at least a first fluid inlet 15 and a second fluid inlet 12 within the pouch 2, wherein the first and second inlets 15 and 12 are respectively positioned on opposite sides of pouch 2, and more particularly are respectively positioned on opposite sides of a longitudinal axis 'l' that connects the proximal end 16 and the distal end 20 of the pouch 2. When a patient is lying on a side, the pouch may tip over and tends to be aligned such that one side or one internal sidewall of the pouch that connects the proximal and distal ends is higher than an opposite side or opposite internal side wall, and as a result, urine discharged from the penis will pool on or at the lower internal side. Having multiple fluid inlets (e.g. fluid inlets 12 and 15) distributed on opposite sides of the longitudinal axis 'l' ensures that regardless of which side of the pouch is positioned lower, there is at least one fluid inlet that is in the vicinity of the pooling urine and through which the urine can be drawn out of the pouch.

In an embodiment, the distance between the first and second fluid inlets 15 and 12 positioned on opposite sides of the longitudinal axis 'l' is greater than the diameter or width of the aperture 3 provided on the pouch 2. In another embodiment, the distance between the first and second fluid inlets 15 positioned on opposite sides of the longitudinal axis l is greater than the maximum width of said aperture 3 measured on any axis that is perpendicular to the longitudinal axis 'l,' and that passes through the aperture 3.

In an embodiment of the urine removal device 1, a skin-friendly material disposed on one or more external surfaces of pouch 2, for improved patient feel.

Figure 2A:
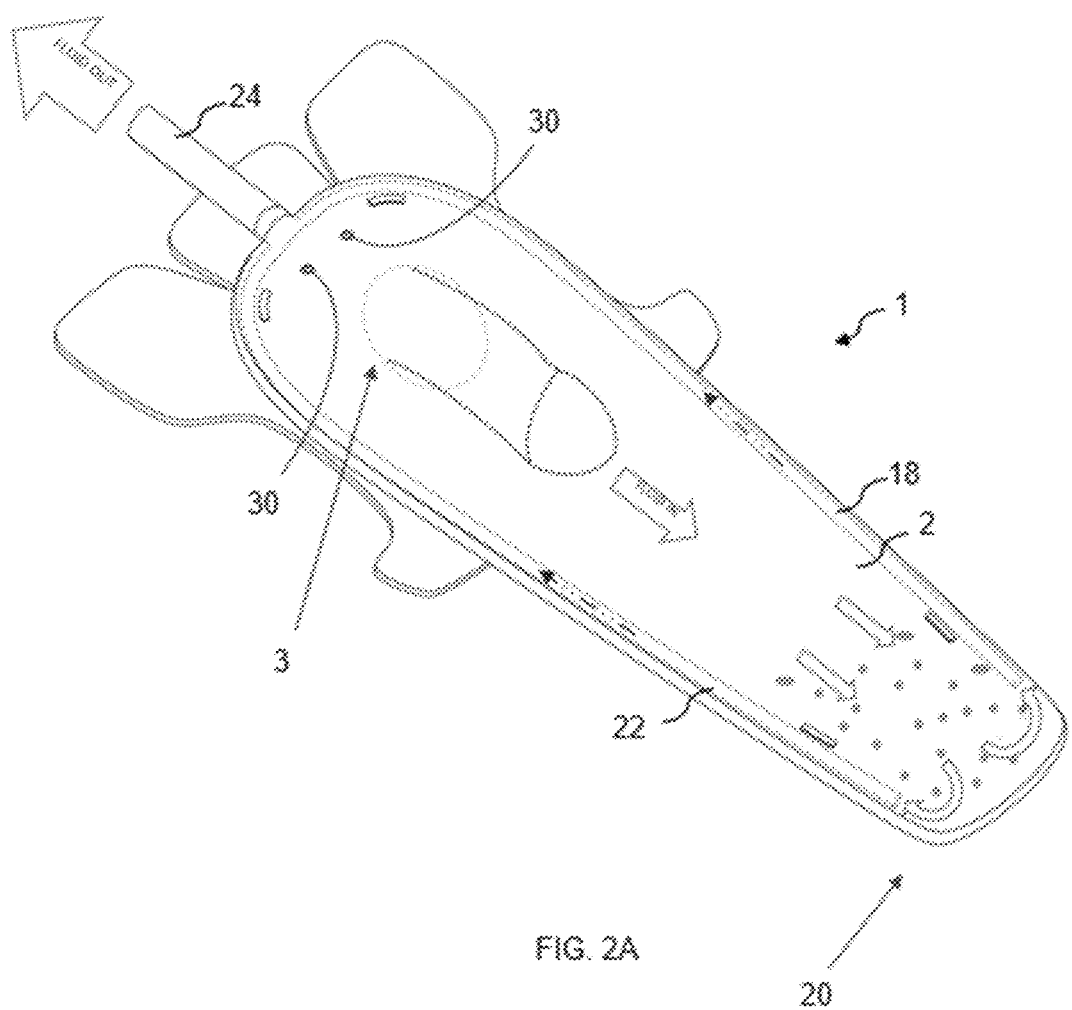
FIG. 2A illustrates the flow pattern through a urine removal device.

The urine removal device is shown in an exemplary patient use scenario in FIGS. 2A-2D. In the above arrangements, the suction source tube 24, which is attached to a vacuum source, provides suction pressure to the conduit members 18 and 22, which extract urine from the distal end 20 of the pouch 2. For example, FIG. 2A illustrates the manner in which urine released into pouch 2 of the urine removal device (by a patient's penis when it is positioned within pouch 2 through the aperture 3) is drawn by negative pressure applied by a vacuum source, from pouch 2 into conduit members 18 and 22 and out of suction source tube 24. To facilitate continued suction and the flow of urine, one or more air ports 30 may be located on the pouch 2 to allow air into the pouch 2 to prevent a vacuum lock condition which may reduce or stop the flow. As used herein, the term "vacuum lock" refers to a condition wherein when vacuum is applied to a cavity with flexible walls, the walls may be sucked into contact, thus restricting or preventing a liquid or gas from flowing through the cavity because the approximated walls reduce or eliminate viable flow paths. One skilled in the art will recognize that additional or alternative air ports may be located at alternative locations to provide an air conduit into the interior of the pouch.

Figure 2B:
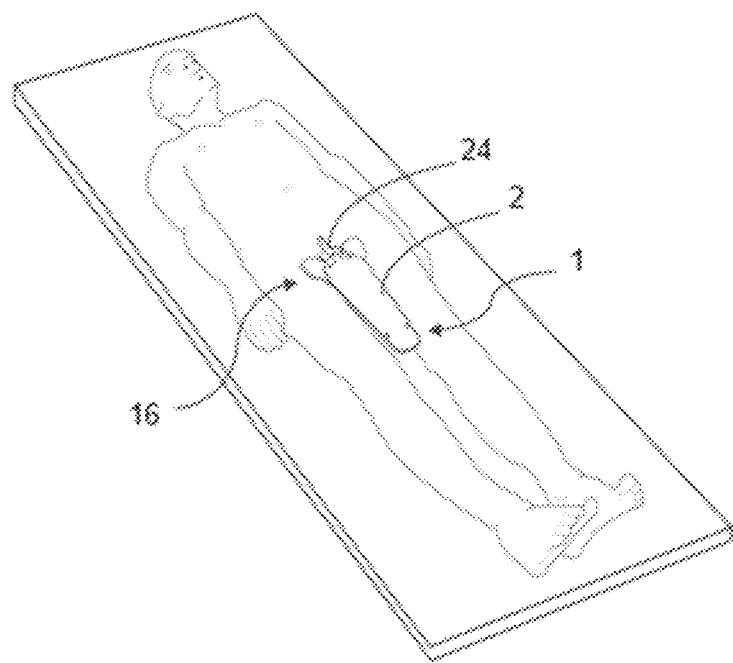
FIGS. 2B-2C illustrate a prone patient wearing a urine removal device according to an example embodiment.
Figure 2C:
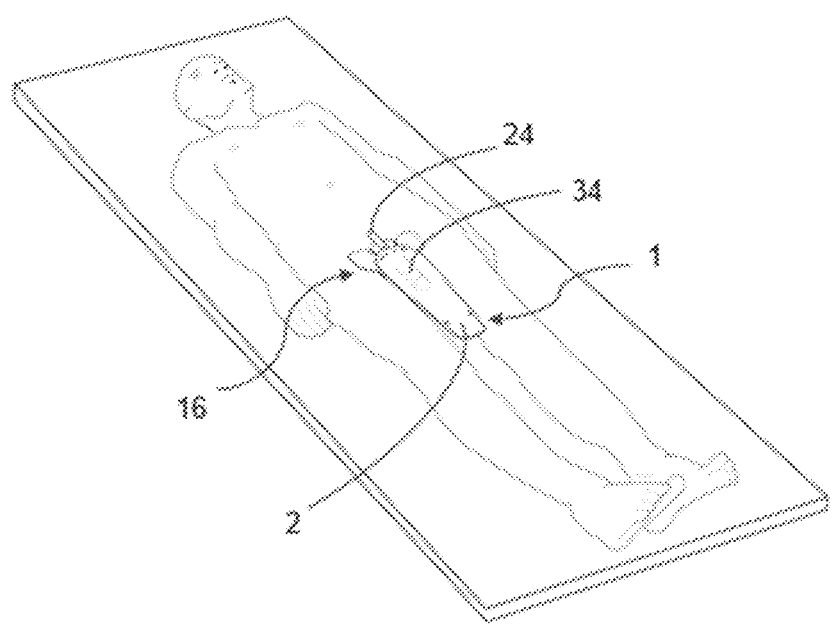

As illustrated in FIG. 2B, the patient is shown laying supine with the urine removal device 1 attached. In this embodiment, the device 1 attaches around the penis such that the suction source tube 24 resides near the lower abdomen rather than between the legs, as is the case with commonly used urinary incontinence devices. This arrangement addresses the problems of the tube contacting the patient's legs and the associated discomfort, pressure point injuries, kinking, leakage, and tangling because no hoses or tubes are residing on or between the thighs. FIG. 2C shows a similar view of the pelvic area however showing the penis 34 residing inside of the pouch 2 near the proximal end 16 of the device 1.

Figure 2D:
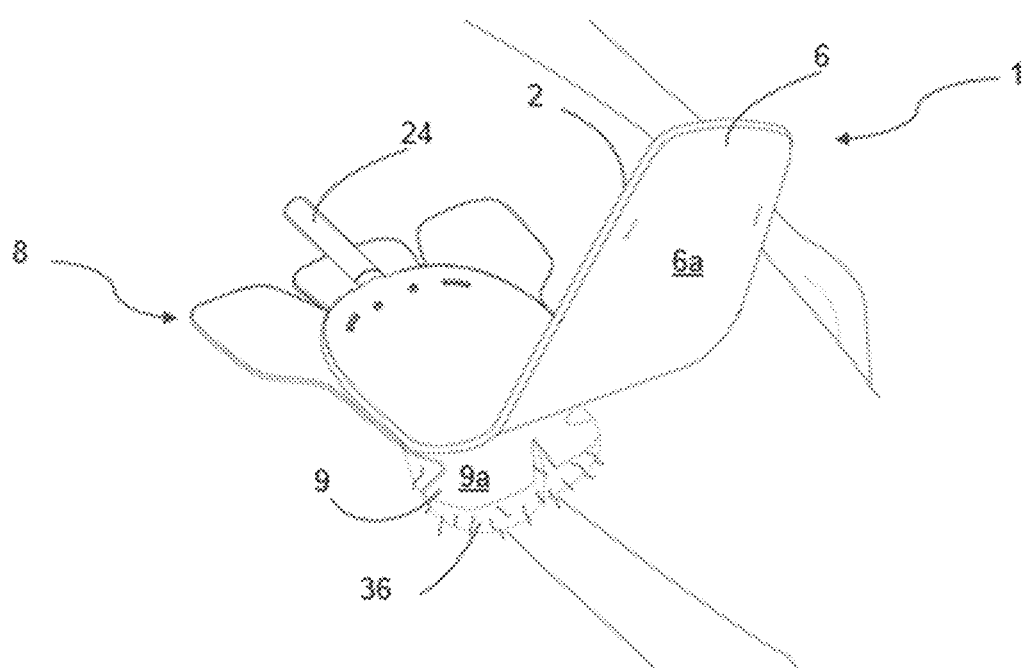
FIG. 2D illustrates a close-up view of the urine removal device of FIGS. 2A-2B showing the attachment to the scrotum.

Now with reference to FIG. 2D, which illustrates how, in some embodiments, the adhesive patch 8 may attach to the scrotum 36. This view shows the pouch 2 folded up only for the purpose of displaying the outer surface 9a of the substrate layer 9, which attaches to the outer surface 6a of the second wall 6 of the pouch 2. The attachment between the outer surface 6a and the outer surface 9a may span the entire outer surface 9a or only part of the outer surface 9a so that in some embodiments, the pouch 2 may articulate somewhat independently of the adhesive patch 8. The inner layer (not shown) of the adhesive patch 8 contacts the body and has an adhesive that allows it to adhere to the scrotum 36, even overtop hair follicles, skin folds, wrinkles, as well as the sweat and moisture that may precipitate in the scrotum and groin area, while being painless to remove from the scrotum 36. One skilled in the art would recognize that there are many appropriate adhesives including porous and nonporous silicones. Adhesive patch embodiments are described below in the section titled 'BODY ATTACHMENT' below.

Figure 3A:
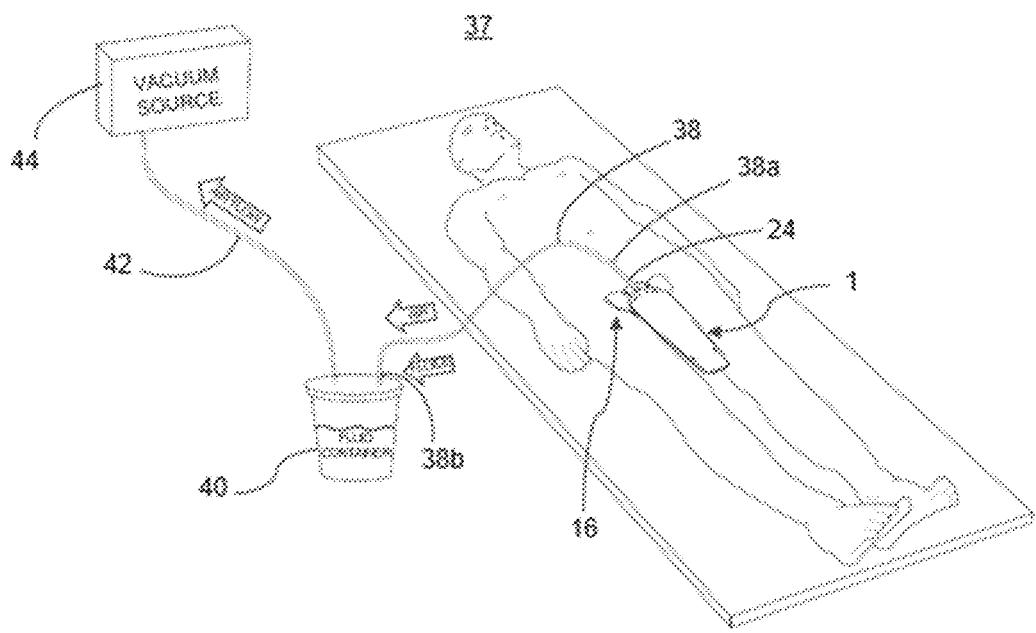
FIG. 3A illustrates a urine management system according to an example embodiment.

Vacuum-assisted urine collection systems typically have a suction tube that runs from the outlet tubing, across the patient, to an external collection system. Conventional effluent collection systems for urine and stool have drainage tubing connection points between the legs, which may lead to leg-entanglement or obstruction from a limb or bedding, and is a known risk factor pressure point injuries and skin breakdown. Placing the access point in the suprapubic region and draping the tubing over the pelvis, hips, or midsection reduces these risks. FIG. 3A illustrates a simplified schematic of a urine management system 37 for collecting urine according to an example embodiment. As shown in FIG. 3A, the system 37 includes the urine removal device 1 described above, a drain tube 38, a urine collection reservoir 40, a vacuum source tube 42, and a vacuum source 44.

The proximal end 16 of the urine removal device 1 is coupled to the drain tube 38, which interfaces with the suction source tube 24 at a first end 38a of the drain tube 38. Any type of connector know by those in the art may be used to connect the drain tube 38 to the suction source tube 24 while being within the scope of this disclosure; examples include a Luer lock, thread, step, or other connector with or without one-way valve. Alternatively, the drain tube and the suction source tube 24 may be one contiguous tube. The drain tube 38 may be a flexible tube that can be manipulated by the practitioner and draped over or under the arm. Notably, the drain tube 38 attaches to the proximal end 16 of the device 1 such that it passes over the abdomen rather than between the legs, where it is directed away from the body (e.g., off of the bed). This arrangement reduces entanglement with the legs and bed sheets covering the legs and reduces accidental pulling of the drain tube 38 from the suction source tube 24, thus preventing leakage when the patient moves and turns in bed while preventing the discomfort of having a tube winding amongst the legs. Having the drain tube 38 accessible across the middle of the body also provides easy access for practitioners as they do not have to search for the drain tube 38 between or underneath the legs.

The second end 38b of the drain tube 38 is coupled to the urine collection reservoir 40 which contains the urine from the drain tube 38. The urine collection reservoir 40 may be a urine collection bag, such as a leg bag or drainage bag, or another container such as a bottle, bucket or canister. The urine collection reservoir 40 may be a sealed device to reduce spillage; in some examples, it may be a disposable unit or it may be a reusable unit that may be washable and/or sterilizable.

The urine collection reservoir connects to the vacuum source 44, which applies vacuum pressure to the vacuum source tube 42 and drain tube 38 to assist in directing the urine from the suction source tube 24 to the urine collection reservoir 40. The vacuum source 44 may be a wall vacuum integrated into a room of a medical facility to its central vacuum generation unit. In other examples, the vacuum source 44 can be integrated with the patient's bed. In general, the urine collection reservoir 40 may include a filter or valve system to prevent urine from transiting up the vacuum source tube and into the vacuum source 44. The system 37 may also include a clip or valve for shutting off the supply of urine from the drain tube 38 so that the urine collection reservoir 40 may be emptied or changed.

Figure 3B:
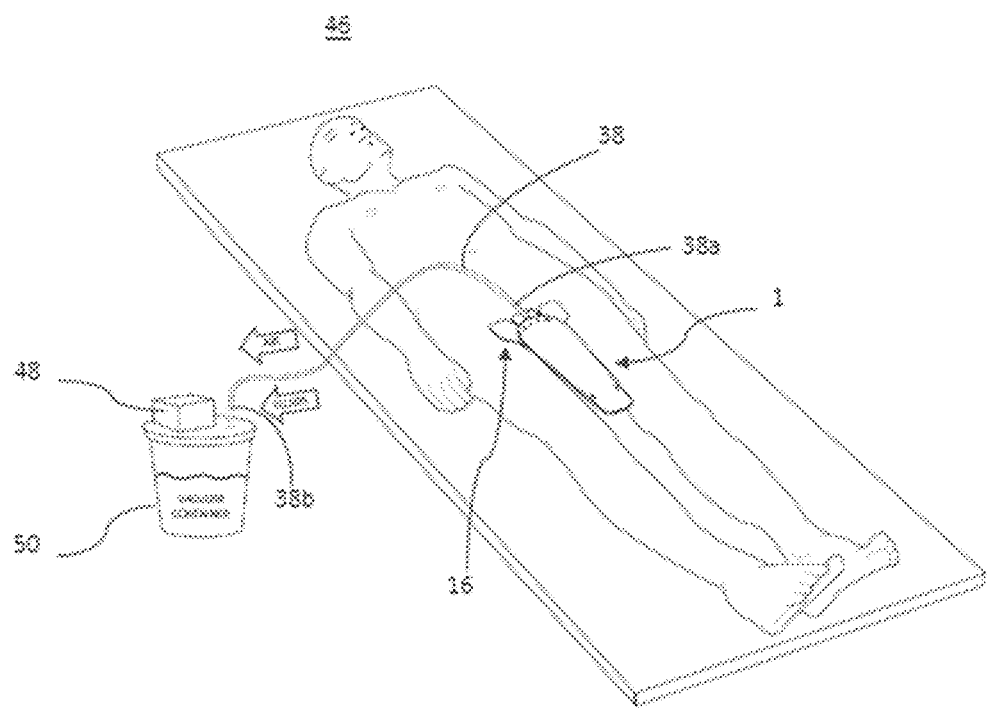
FIG. 3B illustrates a urine management system according to another example embodiment.

Another embodiment of a urine management system 46 is illustrated in FIG. 3B; this embodiment differs from the urine management system 37 of FIG. 3A in that the urine collection reservoir 50 has an onboard vacuum generating unit 48 to create vacuum independently of any hospital or facility vacuum source. Thus, the second end 38b of the drain tube 38 connects into the collection reservoir 50, which has a vacuum source or vacuum generating unit 48 to draw urine into the collection reservoir 50. Since there is no requirement for hospital/facility wall suction, this urine management system 46 offers more flexibility for use in the home, hospice, or long-term care, for example. Additionally, in some embodiments, the onboard vacuum generating unit 48 may be powered by onboard batteries, obviating the need for a power plug and a wall power source, thus providing more flexibility for use in different locations and settings such as a mobile platform, mobile bed, or wheelchair. The urine collection reservoir 50 may be fully reusable, or disposable, or in other embodiments, the urine collection portion may be disposable while the onboard vacuum generating unit 48 may be disposable or reusable.

Fluid & Moisture Removal

The ability of the system to effectively remove fluid & moisture is influenced by at least three aspects of the device design: the pouch, the fluid flow system, and the structural support system, all of which may be coupled. More detailed descriptions of each aspect are described below.

Pouch

The pouch is defined by a substantially flexible and liquid impermeable form with a fluid receiving area between one or more walls (for example a first wall and a second wall). The form creates an essentially enclosed space, either independently or when in communication with the body, and has a patient-side (second wall) and an environment-side (first wall). The form is configured to be liquid impermeable and essentially enclosed to provide a receiving area to receive urine and at least temporarily hold urine within the enclosed space. The impermeable form may be constructed of multiple layers, either coupled or uncoupled, and the entire construction of layers, whether single or multiple, may be described as a flexible wall.

The outermost aspect of the flexible wall is composed of a liquid impermeable material to ensure any effluents received are temporarily contained within the form. The flexible wall is fashioned such that the internal aspect of the enclosed space will not allow the flexible form to collapse in a way that can fully or partially block fluid communication between the proximal and distal ends of the space. Fluid communication requires some viable flow channels between the surfaces and may be achieved with a variety of constructions. Furthermore, the flexible wall can be fabricated to reduce or eliminate the occurrence of a vacuum lock. In these instances, a low pressure pulls a surface against either the source itself in such a way to prevent fluid communication or pulls two or more surfaces against each other in a manner that creates a separate chamber surrounding the source resulting in a chamber that is no longer in fluid communication with the original enclosed space.

As described in more detail herein, example embodiments of the pouch illustrate features for maintaining fluid communication between opposing ends of the liquid impermeable form such as by way of nonlimiting example: the addition of physical separation components running from one end of the form to another end or through a section of the form, the inclusion of material within the form involving physical characteristics such as webbing or mesh, texturing of the form internal or external surfaces, creating undulations or texture-like features by altering the form's cross-sectional shape, or utilizing a material and design that provides a shape whose structure is stronger than the forces that would collapse the form. One skilled in the art would recognize that there are many other ways to maintain fluid communication inside the pouch and such designs are within the spirit of the embodiments disclosed herein and contemplated in this disclosure.

"Flow directors," as used herein refers to features on or within the pouch that provide for fluid flow channels or pathways to provide for urine flow within and out of the pouch, for example when the urine removal device is exposed to applied vacuum. The features may be at a small scale such as where capillary forces govern, or larger features, or combinations of small and large features, with for example, surface treatments that may affect hydrophobicity. The flow directors provide grooves (channels) when the pouch walls come together under vacuum, thus preventing vacuum lock between the layers of the pouch. In some embodiments the flow directors are oriented in the direction of the desired flow but in other embodiments flow directors may be at other angles or randomly arranged. The following figures and descriptions provide non-limiting examples of flow directors.

Flow directors can be formed from the same base material as that of the pouch layer or of different material which may be then bonded with the pouch layer using the process of heat or other method of lamination, gluing, chemical bonding, printing, or any other similar processes practiced in the art. When flow directors are made of same base material as that of the pouch layer, they can be formed during the primary extrusion of the pouch layer or later using a secondary process such as embossing, chemical etching, laser etching, grooving, engraving, carving, imprinting, etc. The flow directors may be left uncoated or coated with chemicals such as Teflon, PTFE, etc. or nanoparticles to improve hydrophobicity. The size of flow directors can range from few nanometers, as it would be in case of etching, to few microns as it would be in case of embossing, to tens of hundreds of microns as it would be in case of the lamination processes. The flow directors can be linear, such that they substantially align with the axis connecting the proximal and distal end of the pouch, wavy, diamond, honeycomb or any other similar shape, or completely random, that may be interconnected with one another in such a way that the gross effect attained by the flow directors is in the desired direction of flow. The flow directors can be on the entire surface or some part of the inner surface of one or both pouch layers.

Figure 4A:
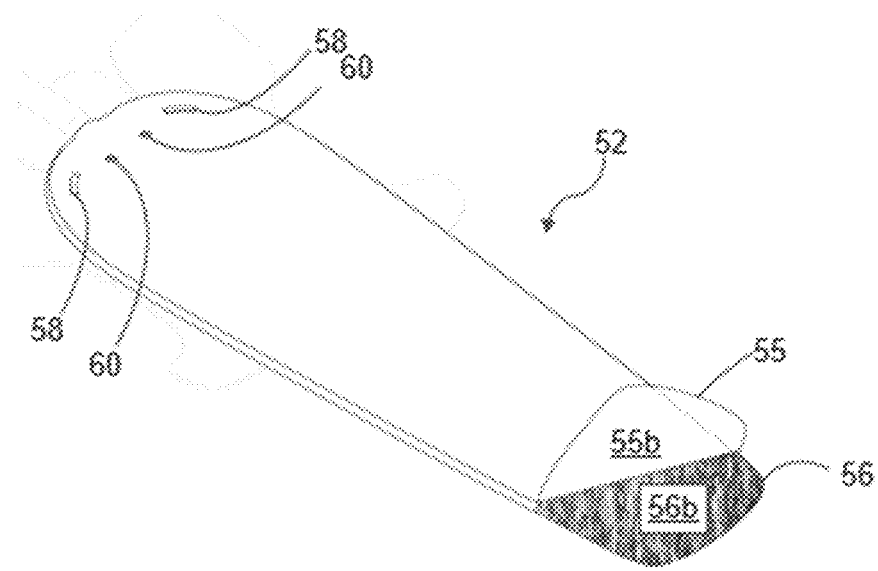
FIG. 4A illustrates a perspective view of a urine removal device having flow directors on a second wall according to an example embodiment.

FIGS. 4A-4D show pouch embodiments with differing layups that include surfaces with flow directors. With reference to FIG. 4A, an embodiment of a pouch 52 is shown which may have conduit member retainers 58, air ports 60, and a first wall 55, through which the air ports 60 pass, and a second wall 56 connected to the first wall 55. In embodiments, the inner surface 55*b* of the first wall 55 may be substantially bare, as shown, that is, untreated and unlaminated, while the inner surface 56*b* of the second wall 56 may have flow directors which may, for example, be molded, hot-rolled, deposited, bonded, spray-coated, etched, formed or embossed in the inner surface 56*b* or attached as a laminate on inner surface 56*b*. Inner surface 56*b* is shown shaded in the figures to illustrate that it has flow directors.

Figure 4B:
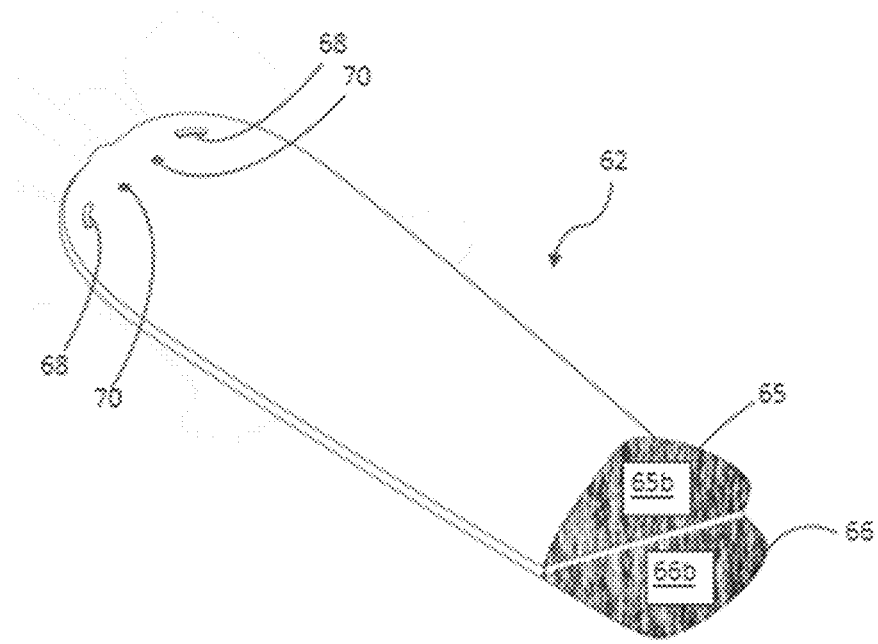
FIG. 4B illustrates a perspective view of a urine removal device having flow directors on a second wall and a first wall according to an example embodiment.

With reference to FIG. 4B, an embodiment of a pouch 62 is shown which may have conduit member retainers 68, air ports 70, and a first wall 65, through which the air ports 70 pass; the first wall 65 is connected to a second wall 66. This embodiment differs from that in FIG. 4A in that both the inner surface 66*b* of the second wall 66 and the inner surface 65*b* of the first wall 65 may have flow directors which may be molded, hot-rolled, deposited, bonded, spray-coated, etched, formed or embossed in the inner surfaces 65*b* and 66*b*, or attached as a laminate on inner surface 65*b* or 66*b*, for example. Inner surface 66*b* and inner surface 65*b* are shown shaded in the figures to illustrate that each has flow directors.

Referring now to FIG. 4C, another embodiment of a pouch 72 is shown which may have conduit member retainers 78, air ports 80, and a first wall 75, through which the air ports 80 pass; the first wall 75 is connected to a second wall 76. This embodiment differs from that in FIG. 4B in that both the inner surface 76*b* of the second wall 76 and the inner surface 75*b* of the first wall 75 may be bare, while flow directors may be either molded, hot-rolled, deposited, bonded, spray-coated, etched, formed or embossed or attached as a laminate on one or both sides of the middle layer 79 which is disposed between the second wall 76 and the first wall 75. Furthermore, the middle layer 79 resides captive between the first wall 75 and the second wall 76 and it may be floating, that is not directly attached, or it may be attached to one or both walls 76 or 75 by, for example, lamination, bonding or heat staking. One skilled in the art will recognize that there are many types of flow directors and concomitant manufacturing and attachment methods that serve to separate the walls and provide small channels for fluid to pass, and several examples will be described in more detail below.

In this and other pouch embodiments disclosed herein, (referring to FIG. 4A) the first wall 55 and second wall 56 may be attached at their peripheral edges, or at other points between them, or a combination of the peripheral edges and discrete or continuous surfaces or lines between the layers. The walls may be joined by any method for joining polymeric sheets as known by one skilled in the art such as heat sealing (heat staking) or adhesive or solvent bonding. The conduit member retainers may be made by joining discrete spots or lines between the first wall 55 and second wall 56, for example, and may also be locations where the first wall 55 and second wall 56 are joined together. Alternatively, in other embodiments, the conduit members may be joined directly to one or both walls directly as described elsewhere in this disclosure.

As noted above, flow directors may be located on any one or more of the surfaces on the inside of the pouch. In some embodiments, and with reference to the pouch 52 in FIG. 5A, the inner surface 56b of the second wall 56 may have flow directors as depicted by the shaded striations extending longitudinally in FIG. 5A. This arrangement is essentially the same as that shown in FIG. 4A, except that the first wall 55 is peeled up longitudinally to show a portion of the inside of the pouch 52. The flow directors may be any type of texture that tends to keep the second wall 56 and first wall 55 separate in at least some areas of the inside internal compartment of the pouch so that liquid (urine) and air may flow without having a partial or total vacuum lock condition—a condition wherein the walls stick together due to the air suction and/or capillary or stiction forces between the walls. In addition, the flow directors may have some preferential orientation, either entirely across the surface, or on average, such that urine is channeled from one end to the other end of the pouch as it is drawn by the tips of the conduit members.

The orientation of the flow directors is further emphasized in FIGS. 5B-5D, which show various orientations of the directors with respect to the longitudinal (proximal to distal) axis of a pouch. FIG. 5B shows a section of a pouch wall with directors indicated by shaded striations oriented along 0 degree vectors 82 indicating alignment with the pouch longitudinal axis, as described below in more detail. FIG. 5C shows a section of a pouch second wall with directors indicated by shaded striations oriented along vectors 84, indicating 15 degrees of angle with respect to the pouch longitudinal axis. FIG. 5D shows a section of a pouch second wall with directors indicated by shaded striations oriented along 90 degree vectors 86 indicating orthogonality with the pouch longitudinal axis and preferred air/liquid flow direction. Depending on the structural features used to create the flow directors, they may or may not be fully aligned homogenously. That is, a distribution of channels, fibers, or whiskers may have a net orientation along the 0 degree vector 82 orientation, but there may be a distribution of angles due to manufacturing processes such that the average angle of these features aligns approximately with the vector 82 orientation (approximately 0 deg.).

In some embodiments, fibers 87, 88, and 89, as shown in FIGS. 5B-5D, may serve as flow directors, and they may be attached to the wall of any of the layers described above and shown in FIGS. 4A-4C, or the fibers 87, 88, and 89 may be attached to a substrate that is, in turn, attached to one of the pouch walls. The fibers 87 may be continuous along the length of the pouch or discrete, having many smaller lengths that overlap, and the size may be lightweight, such as 1-10 denier, or heavy weight in some applications, up to 50 denier or heavier. The height of the fibers 87 should be high enough to allow the fibers 87 to create a channel for fluids to flow between the fibers 87 as the pouch walls are brought together by force or under suction. That is, the height should be large enough to allow urine to flow between the pouch walls without incurring a vacuum lock.

Figure 5E:
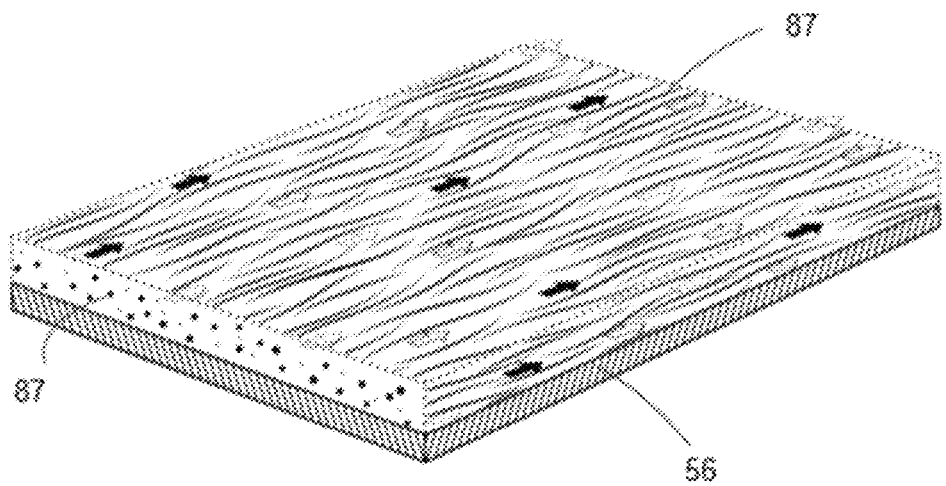
FIG. 5E illustrates a wall having a flow director layer.
Figure 5F:
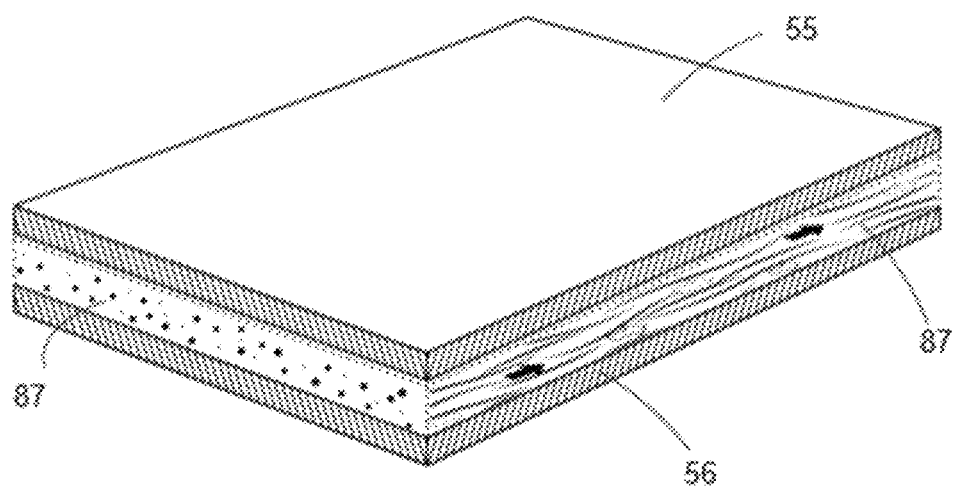
FIG. 5F illustrates a wall having a flow director layer and an opposing wall in contact with the flow director layer.

FIG. 5E shows a detailed view of a section of the second wall 56 of a pouch having flow directors. In this example, the flow directors are comprised of fibers 87 indicated by the various sized dots shown on the end of the cross-section and lines shown on the top and side surfaces. The fibers 87 are generally aligned such that fluid flows in the direction of the arrows, which may be aligned from the proximal to distal end of the pouch. Gaps are formed between the fibers 87 which create grooves for fluid flow. For example, as shown in FIG. 5F, when the first wall 55 and the second wall 56 are drawn together, by vacuum for example, the fibers maintain flow channels so that fluid may flow as indicated by the arrows, the fluid being drawn, for example, by a pressure differential acting on the fluid in that direction.

In some embodiments, the manufacturing process to create the substrate involves having fibers 87 laid down along a moving conveyor belt and then blown with hot air to melt them together. This substrate may be described as melt-blown, airlaid, or hot air through. The fibers may be made of a single material, or multiple materials, for example, wherein two materials (e.g., PE and PP) are joined together in small extruders such that each strand has both materials in a base/binder configuration, wherein the binder has a lower melting temperature. The base/binder ratio may be, for example, from 1:20 up to 20:1. The final substrate (sheet) that contains the fibers may have a sheet weight of about 5-500 gsm and a thickness of approximately 5-500 microns, in some example embodiments.

The fiber material may be a thermoplastic polymer, a thermoset polymer, or combination thereof, or a natural fiber. Examples of suitable thermoplastics include but are not limited to: polyethylene, polypropylene, polyethylene terephthalate, polyamide, polyvinyl chloride, polyester, polyether, polyurethane, polytetrafluoroethylene, block-co-polymer elastomers, polyamid. Examples of suitable thermosets/rubbers include but are not limited to: butyl, chloroprene, epichlorohydrin, ethylene/acrylic, ethylene-propylene, fluorocarbon, fluorosilicone, silicone rubber, natural rubber, nitrile, hydrogenated nitrile, perfluoroelastomer, polyacrylate, polysulfide, styrene butadiene. Examples of suitable natural fibers include but are not limited to: linen, silk, and wool.

In some embodiments, the fibers 87 are hydrophobic either because the underlying fiber material is inherently hydrophobic, or it is treated with a hydrophobic compound making it non-wicking. Hydrophobicity tends to prevent attraction (wetting or wicking) of the urine to the surface. However, depending on the nature, size, and orientation of the fibers, a neutral or hydrophilic material may be similarly functional. Additionally or alternatively, the fibers may be constructed of a nonwoven material.

A nonwoven fibrous surface may be particularly slippery against skin so that the penis does not get stuck while inserting it into the pouch, making the application of the device convenient for the operator and comfortable for the patient. Furthermore, a nonwoven fibrous material tends to dry to the touch rapidly when the urine is partially or fully evacuated so that nearly all liquid can be removed quickly, reducing the risk of skin maceration.

Figure 6A:
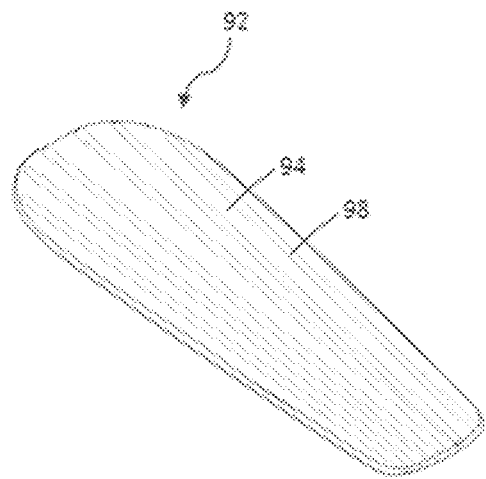
FIGS. 6A and 6B illustrate a perspective view and an exploded view, respectively of a pouch having flow directors according to an example embodiment.
Figure 6B:
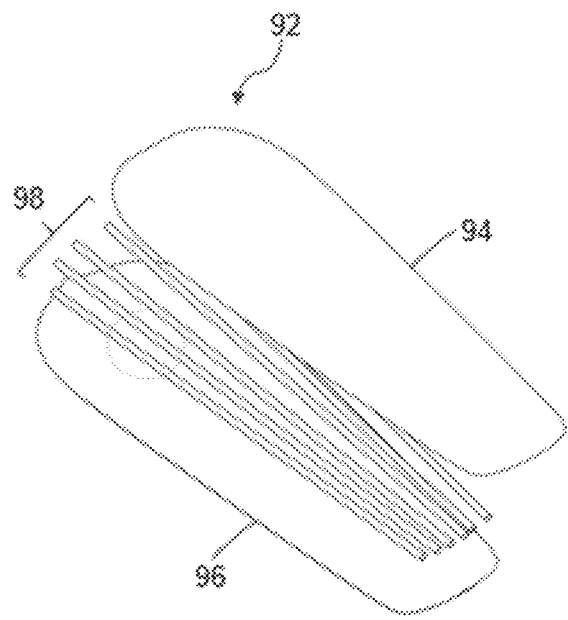

One skilled in the art would recognize that there are many physical shapes or materials that can maintain space between the pouch walls to prevent vacuum locking. By way of example, further embodiments are shown in FIGS. 6A-12. For example, FIGS. 6A-6B show a perspective view and an exploded view respectively, of a pouch 92 having a plurality of elongate members 98, such as rods, located inside the pouch 92, between the first wall 94 and the second wall 96. The elongate members 98 may be discrete or attached to each other, and they may be captive inside of the pouch with or without a direct attachment. Alternatively, they may be attached to either the first wall 94 or the second wall 96, or both by bonding or melting with heat (e.g. heat staking). The elongate members 98 are approximately aligned with the longitudinal axis of the pouch and they may span the entire length of the pouch 92 or have a length shorter than the pouch 92.

Figure 7A:
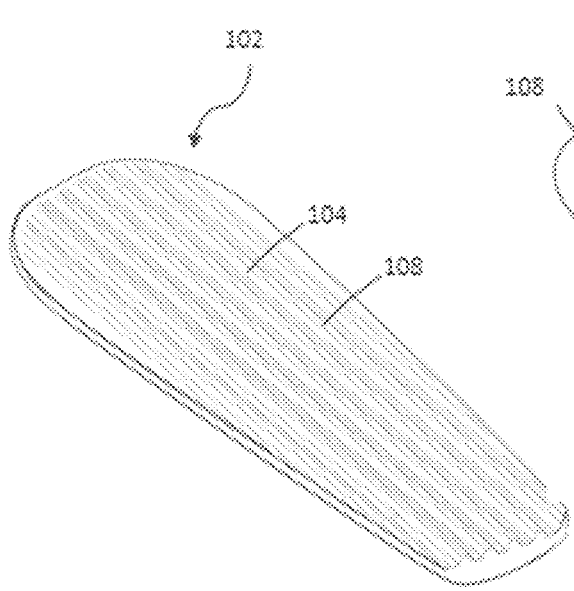
FIGS. 7A and 7B illustrate a perspective view and an exploded view, respectively of a pouch having flow directors according to an example embodiment.
Figure 7B:
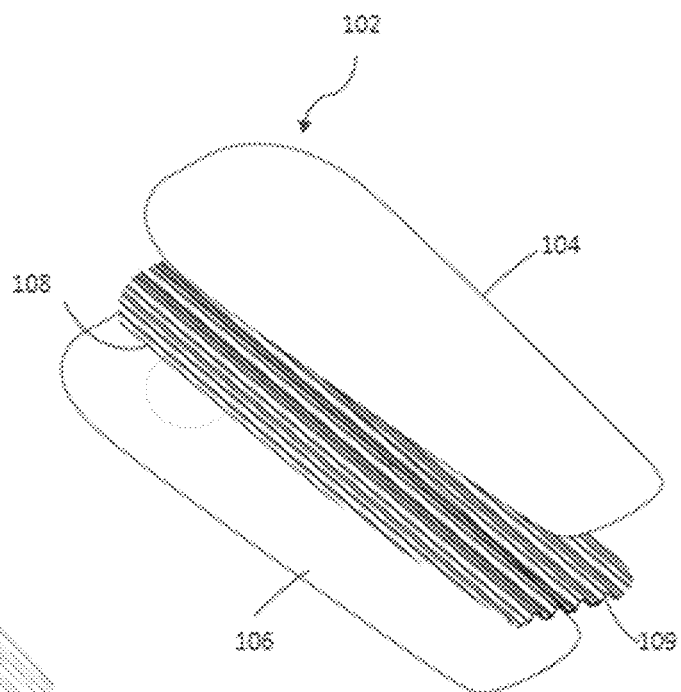

FIGS. 7A-7B show a perspective view and an exploded view respectively, of a pouch 102 having corrugated sheet 108 located inside of the pouch 102 between the first wall 104 and the second wall 106. The corrugated sheet 108 may be captive inside of the pouch with or without a direct attachment. Alternatively, the sheet 108 may be attached to either the first wall 104 or the second wall 106, or both by, for example, bonding or melting with heat (e.g., heat staking or thermal bonding). The channels 109 in the sheet 108 are aligned or approximately aligned with the longitudinal axis of the pouch, and they may span the entire length of the pouch 102 or have a length shorter than the pouch 102.

FIGS. 8A-8B show a perspective view and an exploded view respectively, of another embodiment of a pouch 112 having mesh 118 located inside of the pouch 112, between the first wall 114 and the second wall 116. The mesh 118 may be captive inside of the pouch 112 with or without a direct attachment to the first wall 114 or second wall 116. Alternatively, the mesh 118 may be attached to either the first wall 114 or the second wall 116, or both by, for example, bonding or melting with heat (e.g., heat staking or thermal bonding). The grids 119 in the mesh 118 are approximately aligned with the longitudinal axis of the pouch, and they may span the entire length of the pouch 112 or have a length shorter than the pouch 112.

FIGS. 9A-9B show a perspective view and an exploded view respectively, of another embodiment of a pouch 122 having ribcage 128 located inside of the pouch 122, between the first wall 124 and the second wall 126. The ribcage 128 may be captive inside of the pouch 122 with or without a direct attachment to the first wall 124 or second wall 126. Alternatively, the ribcage 128 may be attached to either the first wall 124 or the second wall 126, or both by, for example, bonding or melting with heat (e.g., heat staking or thermal bonding). The grids 129 in the ribcage 128 are approximately aligned with the longitudinal axis of the pouch, and they may span the entire length of the pouch 122 or have a length shorter than the pouch 122.

Figure 10A:
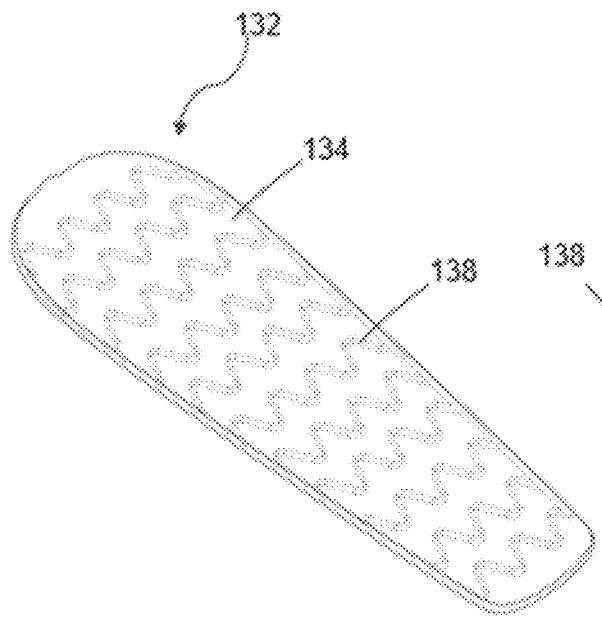
FIGS. 10A and 10B illustrate a perspective view and an exploded view, respectively of a pouch having flow directors according to an example embodiment.
Figure 10B:
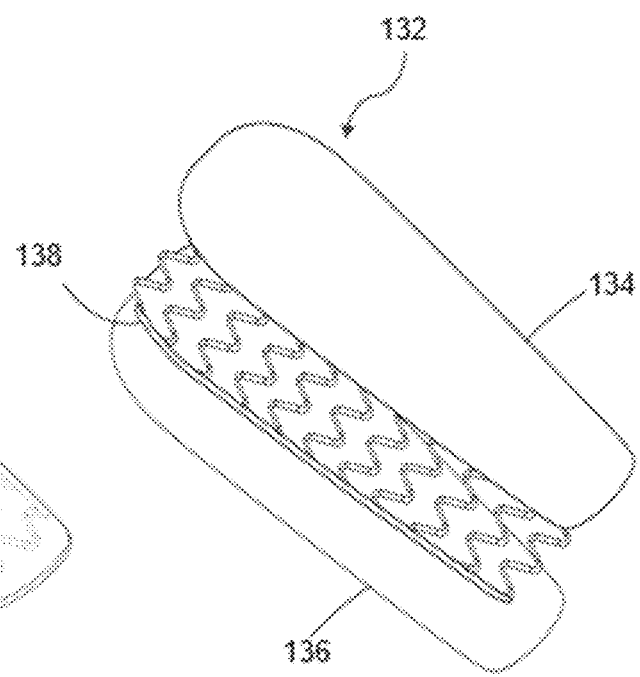

FIGS. 10A-10B show a perspective view and an exploded view respectively, of another embodiment of a pouch 132 having lattice 138 located inside of the pouch 132, between the first wall 134 and the second wall 136. The lattice 138 may be captive inside of the pouch 132 with or without a direct attachment to the first wall 134 or second wall 136. Alternatively, the lattice 138 may be attached to either the first wall 134 or the second wall 136, or both by, for example, bonding or melting with heat (e.g., heat staking or thermal bonding). The lattice 138 may span the entire length of the pouch 132 or have a length shorter than the pouch 132.

Flow directors, including the aforementioned flow directors disclosed herein (e.g., in FIGS. 4A-10B), or other embodiments of directors not particularly detailed here but within the scope of the disclosure, may be made of a polymeric material that may be fabricated by injection molding, blow molding, layer deposition, extruding, or compression molding, for example. Examples of suitable thermoplastics include but are not limited to: polyethylene, polypropylene, polyethylene terephthalate, polyamide, polyvinyl chloride, polyester, polyether, polyurethane, polytetrafluoroethylene, block-copolymer elastomers, and polyamid. Examples of suitable thermosets/rubbers include but are not limited to: butyl, chloroprene, epichlorohydrin, ethylene/acrylic, ethylene-propylene, fluorocarbon, fluorosilicone, silicone rubber, natural rubber, nitrile, hydrogenated nitrile, perfluoroelastomer, polyacrylate, polysulfide, styrene butadiene. Alternatively, the flow directors may be made of a metal such as steel, nitinol or any other suitable metal. The flow directors disclosed herein may be hydrophobic either due to the innate characteristics of the material or due to a hydrophobic coating applied to the material. A hydrophobic surface tends to be non-wicking so as to prevent urine from adhering to the surface so that it can be more readily entrained in the vacuum-driven flow of fluid through the pouch.

Figure 11:
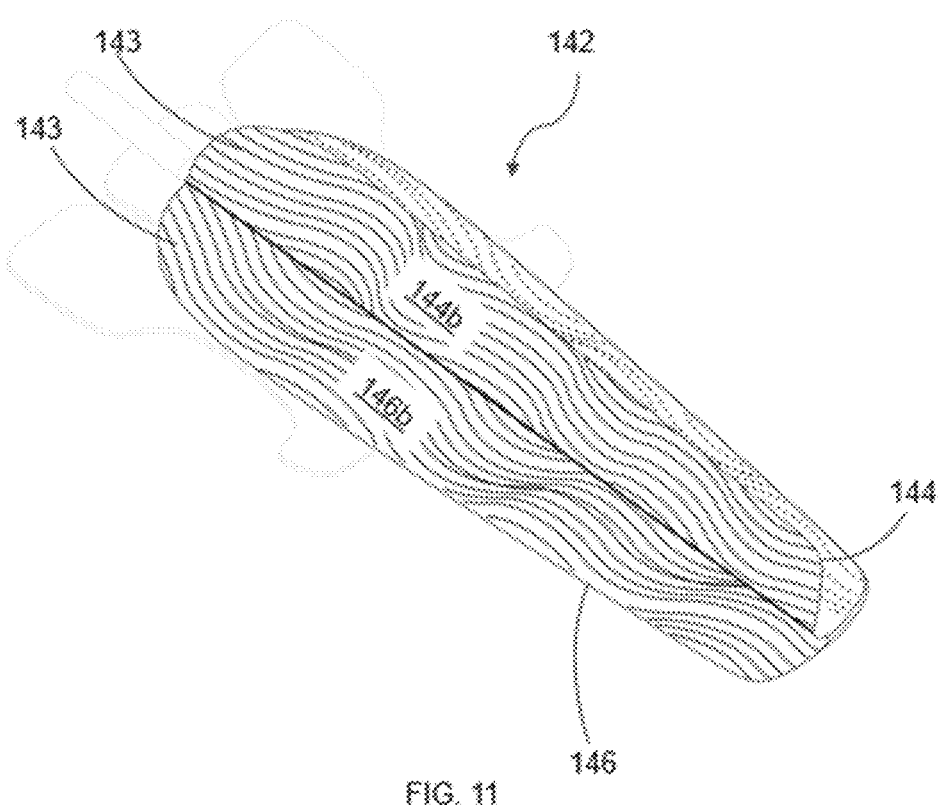
FIG. 11 illustrates a perspective view of a pouch having flow directors according to an example embodiment.

In some embodiments, flow directors may be embedded in the first wall or the second wall, or in a middle layer. The features may be embossed or etched into the material or molded or extruded as part of the fabrication process for the sheet or film material or substrate having the texture. FIG. 11 illustrates an example embodiment of a pouch 142 having a first wall 144 that is shown peeled up longitudinally to expose the inner surface 146*b* of the second wall 146. The inner surface 146*b* has a wave-like pattern 143 of lines that are either raised or recessed into the inner surface 146*b*. This pattern creates a flow director, which maintains flow channels between the first wall 144 and second wall 146 due to the height of the lines. In some embodiments, the inner surface 144*b* of the first wall 144 may have a wave-like pattern 143 in addition to the inner surface 146*b* or instead of the inner surface 146*b*.

Figure 12A:
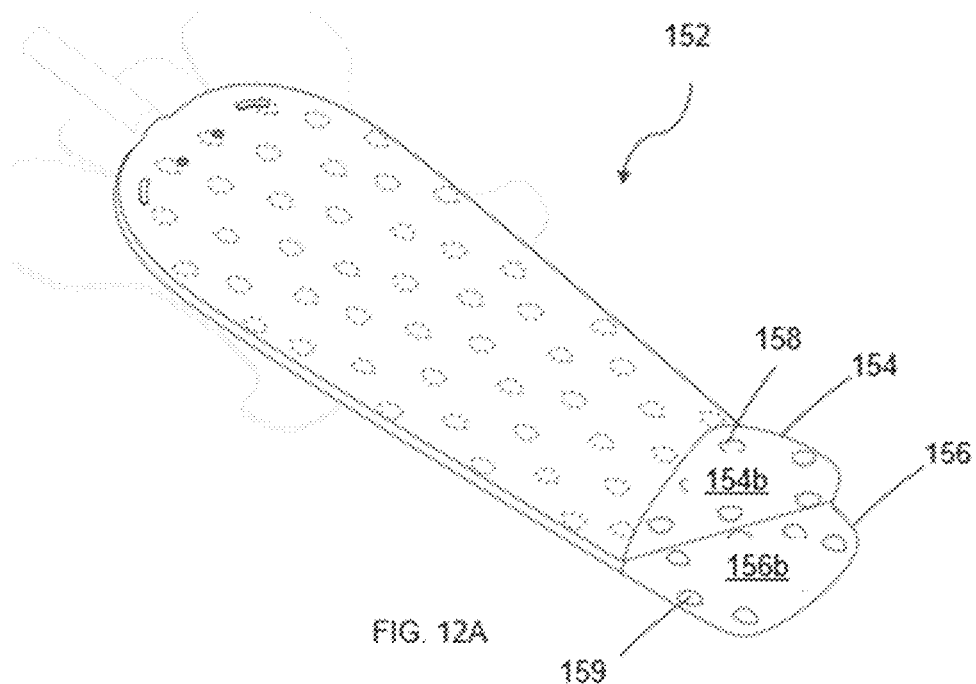
FIG. 12A illustrates a perspective view of a pouch having flow directors according to an example embodiment.

One skilled in the art would recognize that there are many raised patterns that can be made on the inside of one or more pouch surfaces to create an effective flow director. Examples include straight lines, grids, and repetitive patterns such as herringbone, fish scales, diamond, picket, triangle, or arabesque. For example, FIG. 12A illustrates an embodiment having protuberances 158 arranged on the first wall 154 and protuberances 159 arranged on the second wall 156. The protuberances 158 and 159 extend into the interior cavity of the pouch 152; that is, the protuberances 158 on the inner surface 154*b* of the first wall 154 extend toward the second wall 156 and the protuberances 159 on the inner surface 156*b* of the second wall 156 extend toward the first wall 154. The protuberances 158 and 159 may contact the opposing wall to prevent the walls from coming into full contact over significant areas, thus reducing the incidence of vacuum lock. Therefore, gaps between the protuberances 158 and 159 create interstices (acting as flow directors) through which air and urine can flow. The protuberances may be actual solid or semi-solid bumps on the inner walls that are molded in place, or attached via melting, or bonded in place. In other embodiments, the protuberances may be formed in the wall, like a dome, having the same wall thickness as the nominal wall.

Figure 12B:
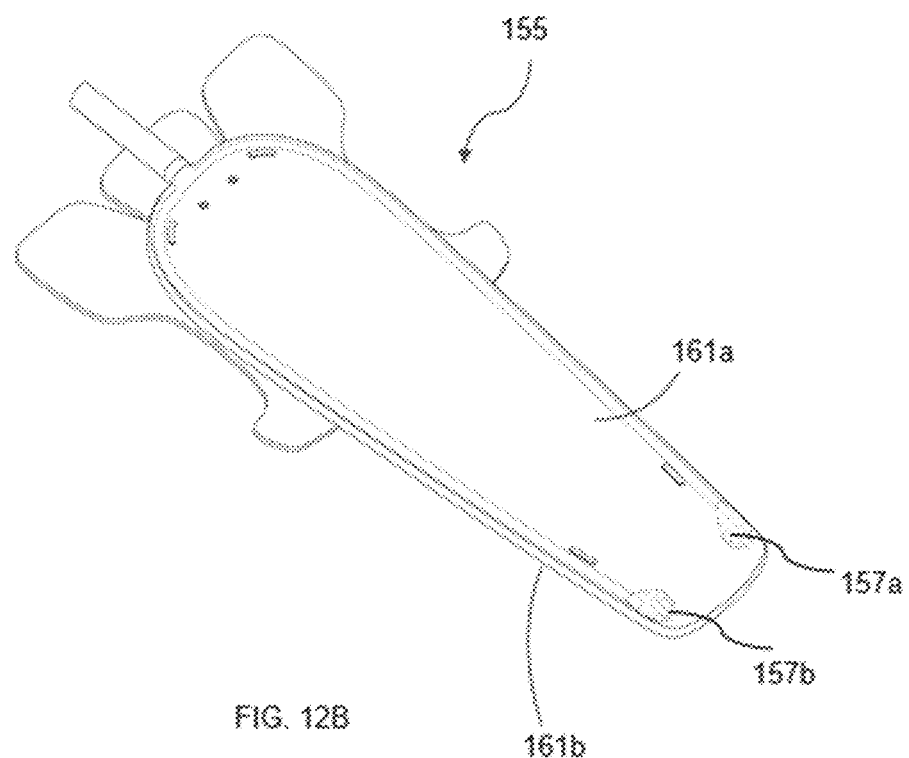
FIG. 12B illustrates a pouch embodiment having flow directors provided only on specific portions inside the pouch.
Figure 12C:
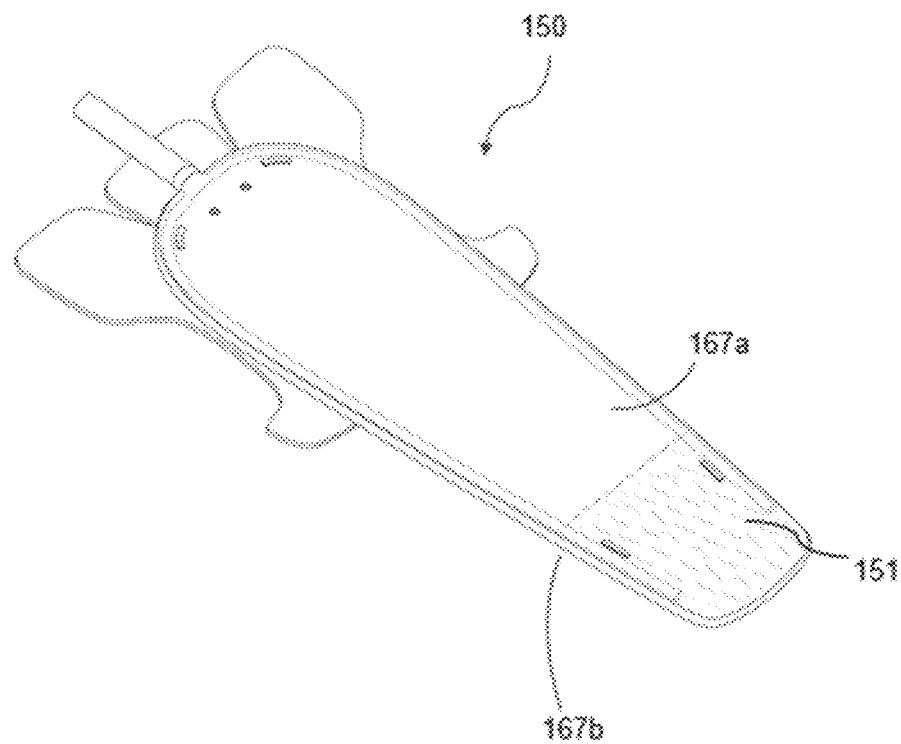
FIG. 12C illustrates a pouch embodiment having flow directors provided only on specific portions of internal walls of the pouch.

Flow directors need not be uniformly arranged on the entire inner surfaces of the pouch. In some embodiments, flow director structures may simply be formed or provided on inner surfaces of the pouch that are located in the vicinity of one or more fluid inlets within the pouch. FIGS. 12B and 12C, respectively, illustrate perspective views of pouch embodiments having flow directors provided only on specific portions of internal walls of said pouch.

FIG. 12B illustrates an embodiment of a pouch 155 where two teardrop shaped flow director structures 157*a* and 157*b* are formed on one or both of the inside surfaces of the first wall 161*a* and the second wall 161*b* of the pouch 155 and in the vicinity of the fluid inlets of the conduit members in the pouch 155. FIG. 12C illustrates an embodiment of a pouch 150 having a region comprising one or more flow director structure(s) 151, formed on one or both inside surfaces of pouch 150 between the first wall 167*a* and the second wall 167b at the distal end of the pouch 150, i.e., located at a distal end of the pouch 150 in the vicinity of the fluid inlets of the conduit members inside of the pouch 150.

Figure 13:
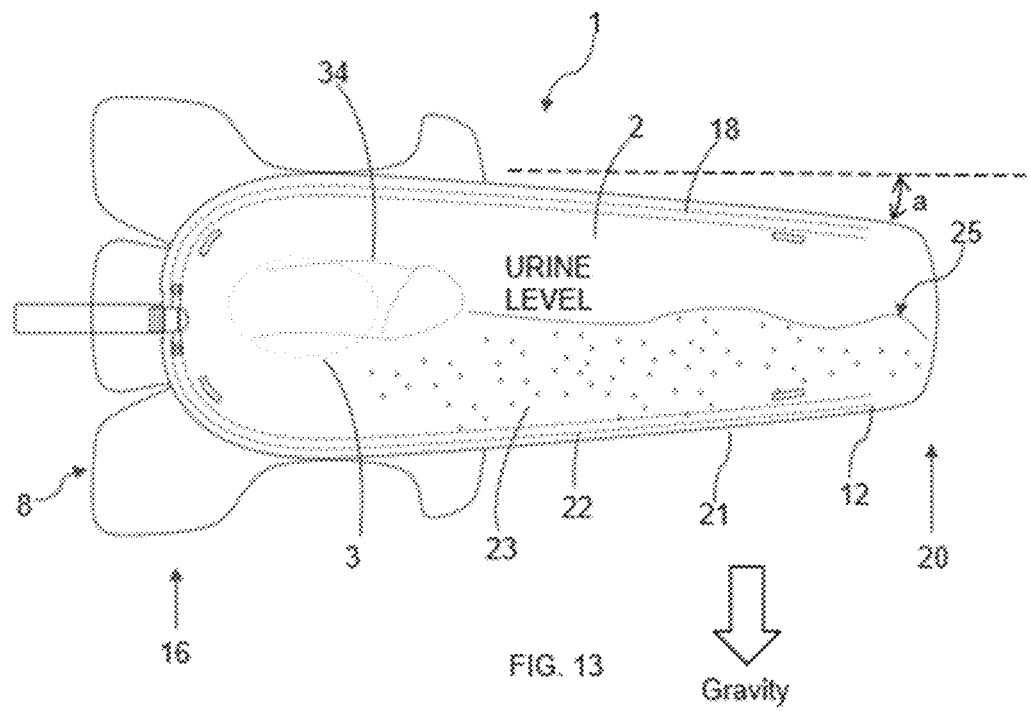
FIG. 13 illustrates the urine removal device oriented on a side showing urine temporarily pooling to one side of the device according to an example embodiment.

The shape of the pouch 2 is generally rectangular with a proximal end 16 that has rounded corners and a distal end 20 that is relatively blunt, as illustrated in a top view in FIG. 13. The device 1 of FIG. 13 is filled partially with urine 23 and it is lying on its side such that the urine 23 fills one side of the pouch 2; this circumstance may occur, for example, if the patient lies on his side. The fluid inlet opening 12 of the conduit member 22 terminates near to but before the distal end 20 of the pouch 2 so that it cannot become blocked by the end of the pouch 2 and it cannot suck the end of the pouch 2 up against the fluid inlet opening 12 of the conduit member 22 which could block the influx of air and urine. In addition, the fluid inlet opening 12 of the conduit member is proximal to the urine 25 that accumulates in the distal end 20 of the pouch 2. Thus, even in this sideways orientation, the side 21 of the pouch 2, being relatively horizontal, allows the conduit member 22 to reside relatively flat so that even when the fluid level decreases, the conduit member 22 will still be able to aspirate most of the urine 23 that has accumulated to the side of the pouch 2. In embodiments, the taper angle "a" of the pouch 2, may be as little as 0 degrees or larger, such as 15 degrees. Even with a 15 degree taper, experiments have shown that with the device 1 on its side as shown in FIG. 13, while exposed to suction, the device can evacuate substantially all pooled urine. Having two conduit members positioned on opposing sides of the pouch can accommodate suction while the pouch is lying sideways in either direction.

When the pouch is tilted, as in FIG. 13, the urine level may be so low that the fluid inlet opening 12 is not submerged in urine. This can cause the conduit to suck in air leaving a pool of urine towards the proximal end of the pouch 2. As such, some embodiments, a conduit may have multiple inlets along its length. Having multiple inlets along the length of the conduit may reduce the amount of pooled urine because there is a greater chance of having one of the inlets submerged in urine when the pouch 2 sits at various pouch orientations. In other embodiments, a conduit may be multi-lumen with each lumen having side openings at various lengths along the lumen mitigate pooling at various pouch orientations. In yet other embodiments, there may be multiple conduits of different lengths adjacent to each other such that the tip of each conduit presents a different inlet along the side of the pouch, again, to mitigate the chance of missing pooled fluid when the pouch 2 resides in various tilted positions.

The pouches disclosed herein may have walls that are made of any suitable material that is highly flexible, i.e., low in flexural modulus and/or thin-walled. In addition, the pouch material may be chosen in some embodiments so that the resulting wall has a thickness of about 5-100 µm, or in some embodiments the thickness may be up to 1 mm. The pouch is liquid impermeable and may be heat weldable, or may otherwise be laminated, bonded, or solvent bonded, to another flexible wall. Examples of suitable materials may include but are not limited to, polyurethane, ethylene vinyl acetate, polyethylene, silicone, rubber, latex, polyolefin, or any other suitable thermoplastic. Furthermore, the pouch walls may be made fully or partially of an odor-blocking material such as a polyamide, polyvinylidene dichloride, ethylene vinyl alcohol or EVOH or similar materials, or alternatively, the odor-blocking material may comprise one or more films coextruded with other suitable materials or otherwise attached to the pouch walls.

While the comfort and environment inside of the pouch is of paramount importance, as described above, the external surface also touches the body on and in-between the legs; although this surface is not typically wet, it may cause a sensation or irritation to the skin over time. As such, the outer surface(s) of the pouch may have a layer of material attached to aid in patient comfort. The layer may be made of suitable thermoplastics, including but not limited to: polyethylene, polypropylene, polyethylene terephthalate, polyamide, polyvinyl chloride, polyester, polyether, polyurethane, polytetrafluoroethylene, block-copolymer elastomers, silicone, rubber, latex, or polyamids. Alternatively, or in combination, natural fibers may be used, including but not limited to cellulose-based materials such as cotton, linen, rayon, or various others such as silk or wool.

Fluid Flow System

The action of a fluid, such as air, passing through the pouch section is integral to the function of the system with respect to the removal of liquid and remnant moisture from the enclosed area created by the liquid impermeable pouch. More specifically, the system may be arranged such that the air flow through the pouch section assists in performing two distinct functions, both a result of the pressure differential created between the pouch section and the conduit system.

The first function is to drain "pooling volumes" of urine received by the pouch section more quickly into the conduit system; this reduces the amount of time that the weight of the urine inside the pouch can act to pull the pouch downward via gravity. During use, the adhesive patch is coupled with the body on one side and attached to the pouch section on the other side. Any weight acting on the adhesive increases stress on the coupling between the adhesive patch and the body, subsequently increasing the risk of dislodgement of the system from its intended location. Furthermore, excess fluid in the pouch can create a force on the patient's legs due to the increased size and weight of the urine-filled device. Transfer of fluid into the conduit system and out of the device reduces these undesirable effects.

The second function is to remove any remnant moisture from the pouch section, which may exist after drainage of larger, pooling internal compartments of liquid. Pressure and concomitant air flow ultimately cause the removal of remnant liquid and moisture from the pouch section into the conduit system. This occurs via two independent mechanisms.

The first mechanism is physical, where negative pressure and the action of air moving across the inside surface of the pouch wall pushes smaller urine droplets that have clung to the surface towards the conduit system. This mechanism is effective when air is pulled through the pouch via the conduit system and flows over the flow directors. The unified design may cause the pressure exerted by the air flow on the droplets to create a force that is greater than the attractive forces between the liquid and the surface, which acts to hold the droplets to the surface. As the size of the water droplet decreases, the cross-section area upon which the air flow has to act decreases, which in turn decreases the exertion force of the air. There will be a balance of forces that eventually results in some small droplets and remnant moisture unable to be moved into the conduit system, which is where the second mechanism is important.

The second mechanism is physical, where the air moving across the inside surface of the pouch wall causes small water droplets and remnant moisture to evaporate and be removed from the enclosed space along with the air itself. Evaporation is dependent on many variables; however, with respect to variables that may be controlled within the disclosed device, volumetric air flow rate, surface area and air velocity are relevant. All of these variables are directly proportional to the rate of evaporation. Furthermore, in embodiments having flow directors, to increase the removal of moisture via this mechanism, the size and orientation of the flow directors with respect to the conduit system may be balanced to adequately expose the urine droplets to the air velocity across different areas within the enclosed space. In experiments, some of the pouch embodiments disclosed herein can be evacuated of urine and dry to the touch within 0.5-15 minutes depending on factors such as the amount of wetness inside the pouch, rate of air flow velocity, vacuum pressure, ambient temperature & humidity, hydrophobicity of the materials, and type and size of flow directors.

Figure 14:
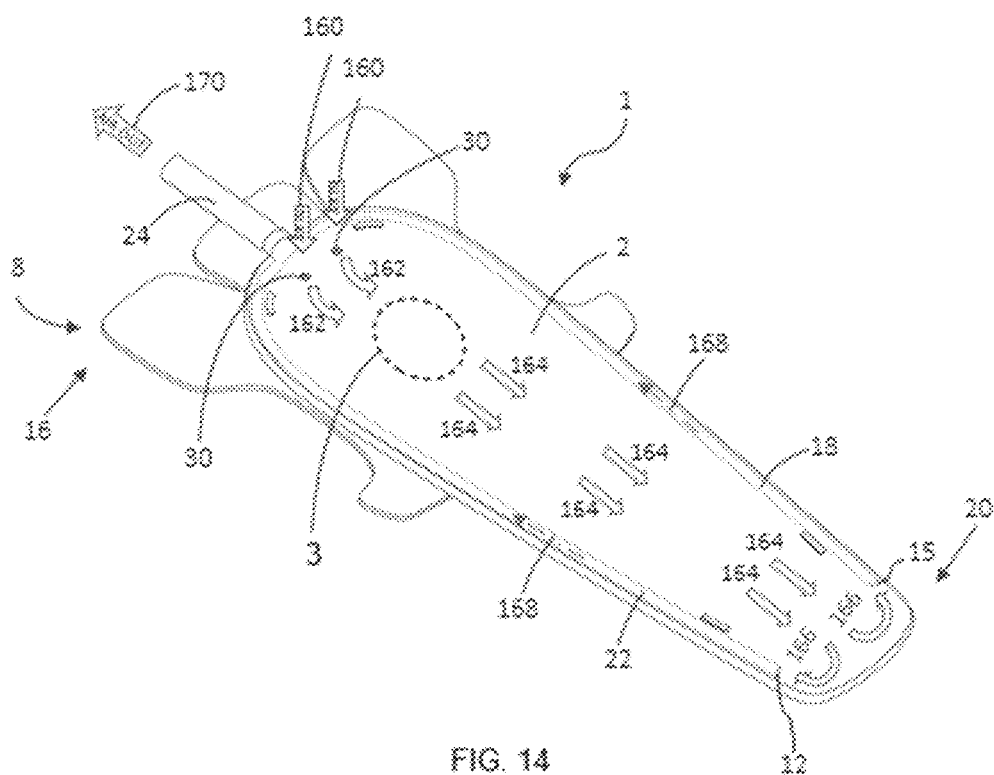
FIG. 14 illustrates the air flow paths of a urine removal device according to an example embodiment.
Figure 15:
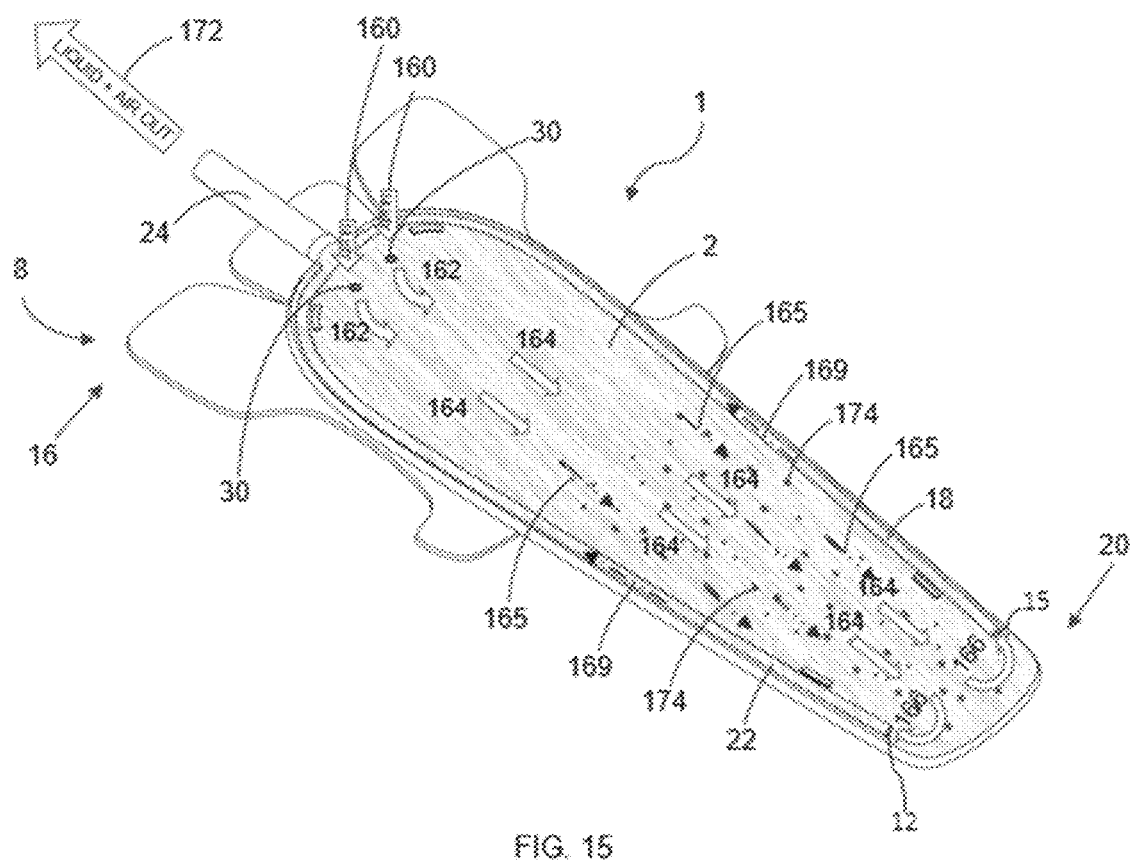
FIG. 15 illustrates the air flow and urine flow paths of a urine removal device according to an example embodiment.
Figure 16:
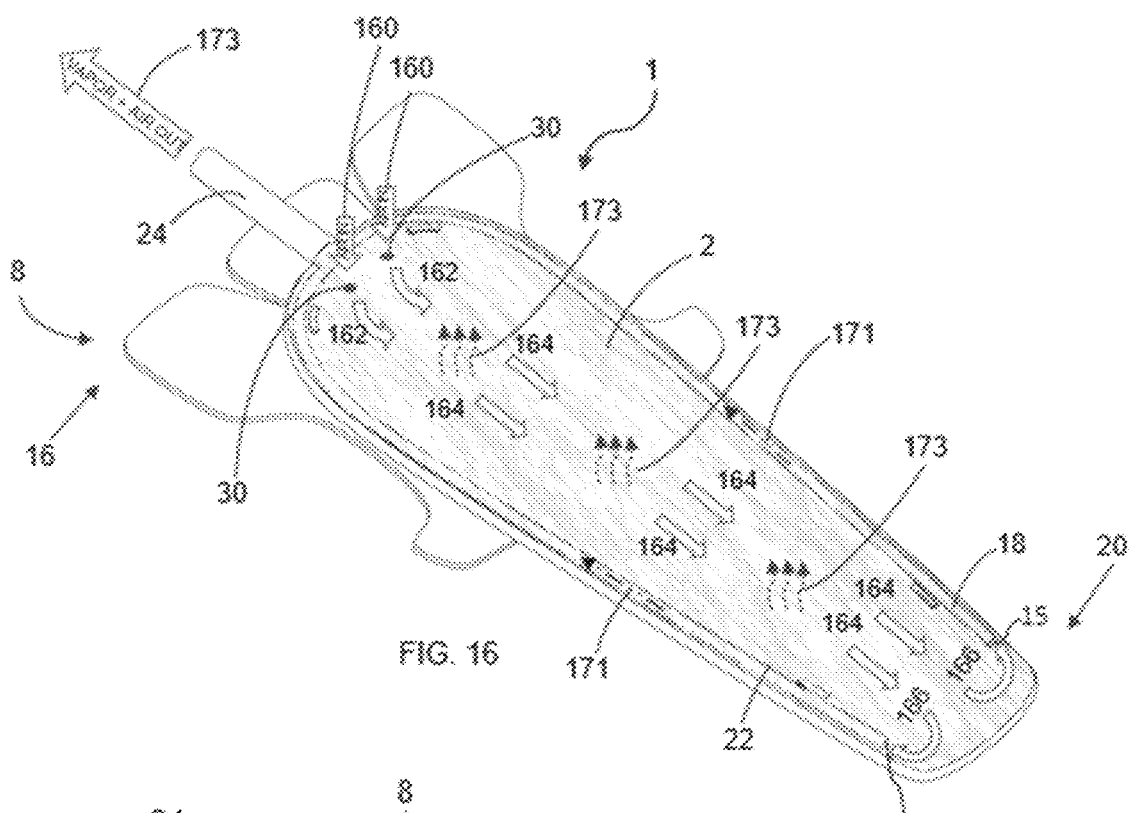
FIG. 16 illustrates the air flow and vapor flow paths of a urine removal device according to an example embodiment.
Figure 17A:
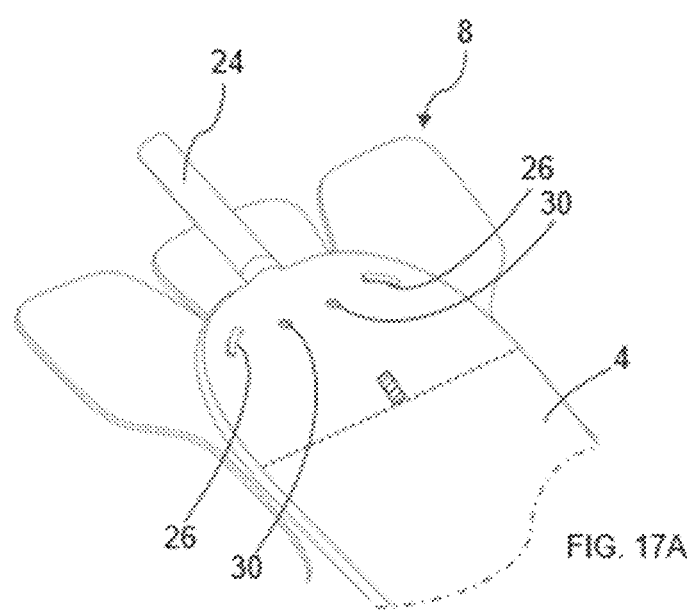
FIGS. 17A-17H illustrates a urine removal device and various types of optional valves for air ingress according to various example embodiments.
Figures 17B, 17C, 17D, 17E, 17F, 17G, 17H:
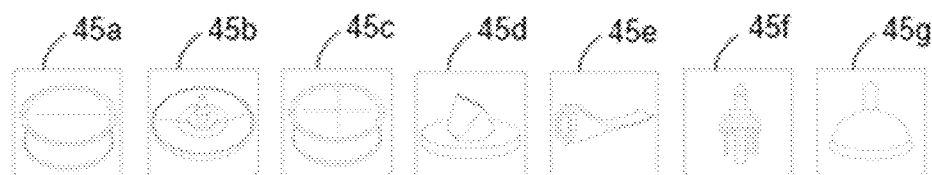

The air and urine flow pathways are illustrated schematically in FIGS. 14-16 in the context of the urine removal device 1 described previously herein. FIG. 14 shows an empty pouch, without urine, with air flow paths depicted by arrows. In embodiments disclosed herein, the air flow is driven by a pressure differential that may be provided by a pressure or vacuum source, which draws air out, as indicated by arrow 170, through the suction source tube 24. The arrows 160 depict air flowing into the pouch 2 through the air ports 30. The air is entrained in the pouch 2 as indicated by arrows 162, after which it flows from the proximal end 16 toward the distal end 20 of the pouch 2 as indicated by arrows 164. Near the distal end of the pouch 2, the air is pulled in through the first conduit member 18 and the second conduit member 22 through fluid inlets 15 and 12 respectively, as indicated by arrows 166, where it travels through the conduit members as indicated by arrows 168. Finally, the air is drawn out through the suction source tube 24 by the applied pressure differential. Notably, in embodiments such as this, the air ports 30 are located near the proximal end 16 of the device 1. This allows the air flow as indicated by arrows 164 to pass by the penis (not shown) because the aperture 3 through which the penis is inserted is distal to the air ports 30.

Now with reference to FIG. 15, which shows a device 1 in an arrangement that is otherwise the same as that in FIG. 14, except that liquid (urine 174) is present in the pouch 2 as indicated by the shading and the droplets. The arrows 160 depict air flowing in through the air ports 30. Next, the air is entrained into the pouch 2 as indicated by arrows 162, after which it flows from the proximal end 16 toward the distal end 20 of the pouch 2 as indicated by arrows 164. In doing so, the air entrains the urine 174 such that it flows along with the air flow as indicated by arrows 165. Near the distal end, the air and urine are pulled in through the first conduit member 18 and the second conduit member 22, as indicated by arrows 166 where the mixture travels through the conduit members 18 and 22 through fluid inlet 15 and 12 respectively, as indicated by arrows 169. Finally, the air/urine mixture is drawn out through the suction source tube 24 by the applied pressure differential as indicated by arrow 172. Thus, the air and urine flow from the proximal to the distal end of the device 1 is driven by the conduit members 18 and 22 having their inlet at the distal end of the pouch 2. This flow conduit arrangement tends to pull the urine away from the penis, which resides in the pouch 2 toward the proximal end 16 of the device 1, resulting in a more comfortable experience for the patient because the urine does not pool or otherwise reside around the penis for an excessive amount of time. Additionally, as a result of the airflow within pouch 2, the air/microclimate within the pouch 2 is quickly dehumidified, and as a consequence the discomfort felt by the patient is minimized.

Now with reference to FIG. 16, which shows a device 1 in an arrangement that is otherwise the same as that in FIG. 14, except that dampness is present in the pouch 2, as indicated by the shading. The dampness is a result of residual urine in the pouch 2 and/or sweat from the patient. As noted above, arrows 160 depict air flowing in through the air ports 30. Next, the air is entrained into the pouch 2 as indicated by arrows 162, after which it flows from the proximal end 16 toward the distal end 20 of the pouch 2 as indicated by arrows 164. In doing so, the air flows across the damp surfaces and through the damp air resulting in evaporation as depicted by arrows 173. The evaporation is enhanced by the forced convection of the air flowing through the pouch 2. Near the distal end 20, the air and urine vapor are pulled in through the first conduit member 18 and the second conduit member 22 through the fluid inlets 15 and 12 respectively, as indicated by arrows 166 where the mixture travels through the conduit members 18 and 22 as indicated by arrows 171. Finally, the air/urine vapor mixture is drawn out through the suction source tube 24 by the applied pressure differential as indicated by arrow 173. Thus, the air and urine vapor flow from the proximal end 16 to the distal end 20 of the device 1 is driven by the conduit members 18 and 22 through their inlet at the distal end of the pouch 2.

In the illustrations shown in FIGS. 14-16, the penis would generally be inside of the pouch, although for clarity, it is not shown. In general, the flow of air through the pouch provides rapid drying of the interior environment of the pouch, which includes the penis, which may also produce sweat in the form of vapor or condensed vapor. The flow directors disclosed herein may increase drying speed as described above. Furthermore, if the flow directors and other materials inside of the pouch are made of nonabsorbent materials, drying may be further accelerated, resulting in a lightweight system with little or no accumulated urine inside. For example, if the nonwoven fiber surface is made of a material that is nonabsorbent, liquids will tend not to absorb or adhere to the pouch materials making the liquids easily entrained with the air flow, leading to faster drying.

In some embodiments, air may also flow into the pouch through the gaps around the location where the adhesive patch 8 attaches to the body. These gaps, do not adversely affect performance because they are near the proximal end 16 of the device 1 and, since the net flow rate in the pouch 2 is away from the proximal end, the flow may ensue in much the same manner as if air is drawn in through the air ports 30. However, if the gaps are very large, they may permit leakage of urine in the proximal direction onto the patient. Furthermore, in some embodiments, air ports may not be necessary because the air gaps around the adhesive patch 8 may provide adequate ventilation to support the suction pressure without collapsing the pouch 2 in a vacuum lock condition.

One skilled in the art will recognize that there are other ways for providing air to the pouch, such as through ports and valves or through gaps, voids, or apertures where the device 1 mounts to the body; all of such variations are within the scope of this disclosure. Next, turning to FIGS. 17A-17H, the proximal end 16 of the urine removal device 1 is once again shown illustrating the air ports 30 through a wall of pouch 2, for example the first wall 4 of the pouch 2. The air ports 30 may comprise one or more small holes or slits, and the risk of leakage through the air ports 30 is reduced by the direction of flow away from the air ports 30 and because the cavity inside of the pouch 2 dries quickly. However, in some circumstances leakage may be caused by, for example, a rapidly urinating patient filling the pouch, the patient or nurse squeezing the pouch, the patient rolling onto it, suction failure, tube kinking, vacuum suction failure, or general handling by a caretaker, or some combination of these factors. In some embodiments, a valve may be used in place of or in addition to the aforementioned air port 30 to create some resistance to the leakage of urine out of the device. One skilled in the art would recognize that there are many valve types and styles that can provide this function, for example a slit valve 45a, an umbrella or flapper valve 45b, a cross-slit valve 45c, a duckbill valve 45d, a flutter valve 45e, a check valve 45f, and a dome valve 45g are shown in FIGS. 17A-17H as examples. These valves may be located at the location where the air ports 30 are located or elsewhere on the pouch 2 generally toward the proximal end of the pouch 2 or toward the middle of the pouch 2 in some embodiments.

Figure 18:
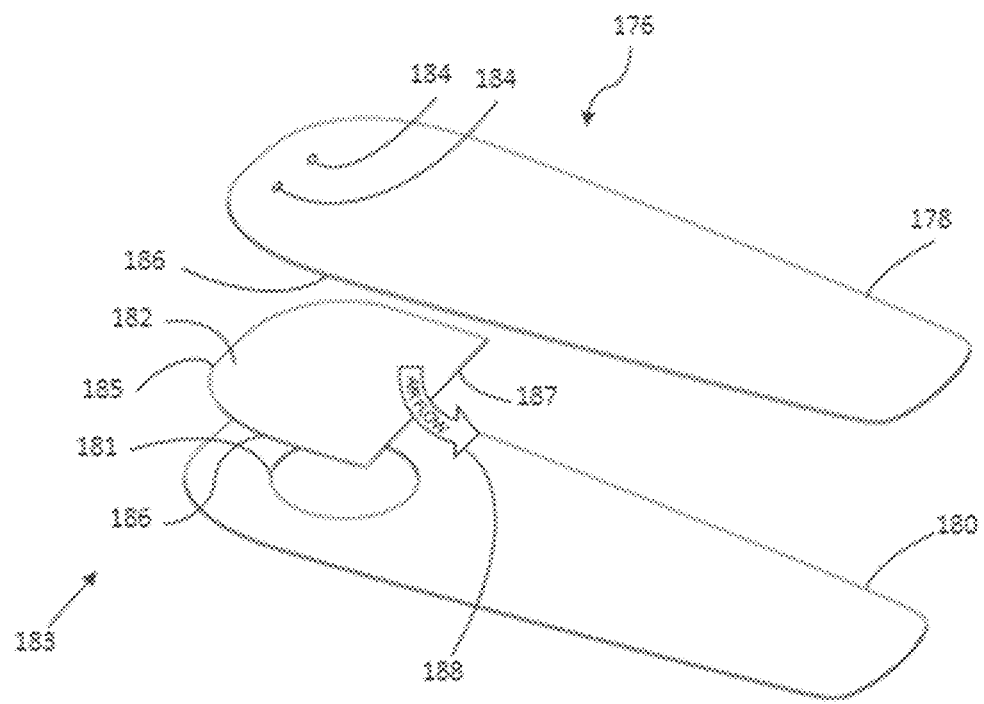
FIG. 18 illustrates the exploded view of a urine removal device having a one-way valve across the air ingress inlets and penis access aperture according to an example embodiment.

Another embodiment of a pouch 176 is illustrated in FIG. 18 in an exploded view showing three layers: a first wall 178, a second wall 180, and a valve layer 182. Air ports 184 and the pouch aperture 181 are also shown in FIG. 18, but for clarity, other features are not shown. The valve layer 182 provides a one-way valve to prevent urine from flowing proximally toward the air ports 184. The valve layer 182 may be attached (or sealed) to the first wall 178 of the pouch 176 at or near the proximal end 185 of the valve layer 182 or at the sides 186 of the valve layer 182 or at the proximal end 185 and the sides 186. The distal end 187 of the valve layer 182 is at least partially open, that is, not attached or sealed to the first wall 178, so that air may flow between the valve layer 182 and the first wall 178 in the direction of the arrow 188. This will allow the air to interact with any urine or liquid vapor in the device in the same manner as shown in FIGS. 14-16 as described above. However, if the bag is tilted or squeezed, liquid may move toward the proximal end 183 of the pouch 176 and reach the distal edge 187 of the valve layer 182 wherein the liquid will generally force the distal edge 187 against the first wall 178, thus preventing backflow into the air ports 184. This operation is similar to a flutter valve.

Structural Support System

As described in more detail above, the conduit system has at least one opening in the proximal and the distal end, with fluid communication between the ends. The open end or ends are intended to divert fluid received by the pouch section away from the penis through the conduit system to an opposing end. The conduit system may include one or more independent lumens, or be configured to create a lumen when coupled with the pouch section. The system may be composed of a single component and single material, or be derived from a combination of various components and materials. The construction is chosen, so that a balance is struck between flexibility and rigidity such that the pouch may bend or flex without obstructing the fluid communication between the proximal and distal ends of the pouch.

The conduit system is arranged within the pouch such that fluid communication between the enclosed area of the pouch and the lumen of the conduit system remains open and substantially unobstructed. More specifically, the coupling is devised so that the movement of either the pouch or the conduit system, such as during bending or twisting of both sections together or of the individual sections in relation to each other, will not reduce the ability for fluid through the pouch and into the conduit members. That is, the intersection between the conduit system and the pouch should not restrict the flow to a point where it is the rate-limiting factor of the system. This may be achieved in various embodiments that tend to keep the pouch and conduit system in a relatively fixed orientation such that they do not appreciably deform relative to each other. In these embodiments, the pouch resists kinking and bending and stays relatively congruent with the conduit system so that flow of air and urine is maintained. This may be achieved, for example, by altering part of either section so the stiffness becomes more similar to that of the other section, or by coupling the sections so that the more flexible portion (pouch) is held in place by the stiffer portion (diverter system). For example, FIG. 19 shows such a scenario wherein the pouch deforms, but the conduit members stay in their place relative to the pouch to provide a restoring force due to their stiffness.

In an embodiment, the conduit system may be comprised of one or more single or multi-lumen lumen extrusions and the pouch may be an essentially elongated shape with a proximal end near the body and a distal end away from the body. The conduit system may run along the pouch section to have an open end near the distal end of the pouch section and an outlet near the proximal end of the pouch. The conduit system may be coupled to the pouch section along at least part of the overlapping length such that movement of the conduit system causes the coupled areas to move in tandem. In some embodiments, the added structural stiffness is due to the size of the conduit members as compared to the thickness of the pouch. For example, a pouch may be flexible because it is made of a polymer having a wall thickness of 50 microns, or even 500 microns, for example, while the conduit members may be made of a polymer and have a diameter of 1 mm-10 mm; when coupled together, the resulting device has a bending stiffness that is orders of magnitude higher than the pouch alone, which may have negligible bending stiffness.

Figure 19:
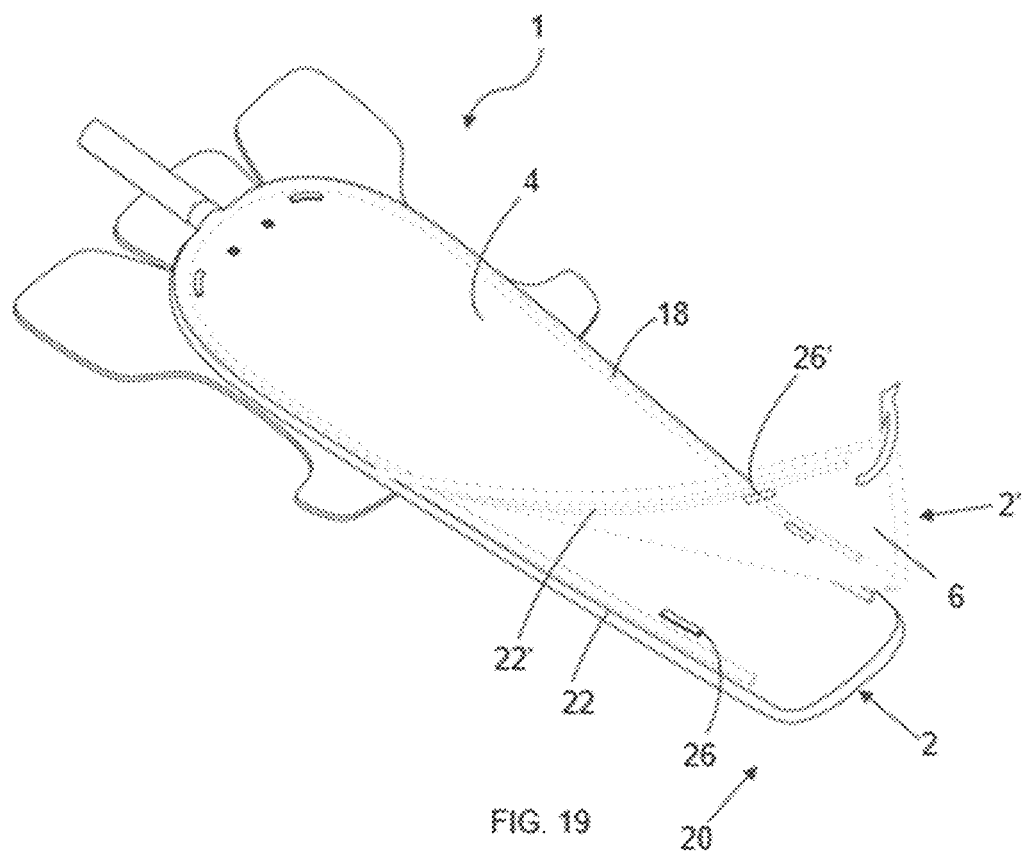
FIG. 19 illustrates a urine removal device having a deformed view overlaid on a perspective view according to an example embodiment.
Figure 20:
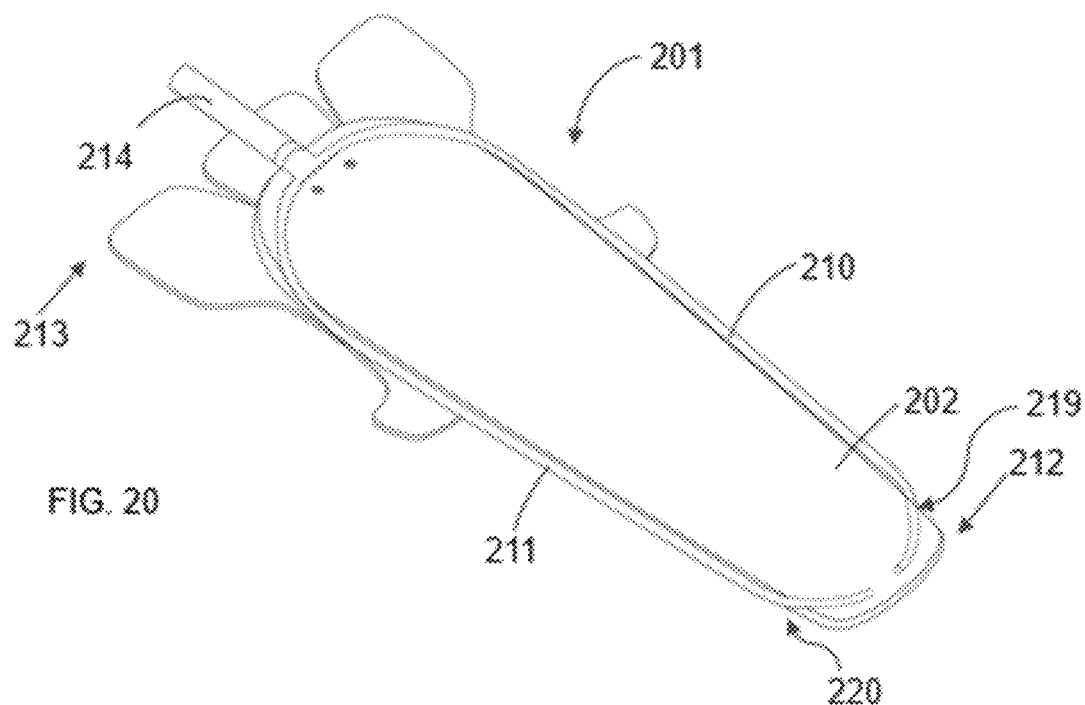
FIG. 20 illustrates a perspective view of a urine removal device having external conduit members according to an example embodiment.

As shown in FIG. 19, the urine removal device 1 is shown with a deformed configuration overlay using dotted lines to illustrate deformation. When the device 1 is loaded such that the pouch 2 deforms, the pouch 2 may rise at the distal end 20 or twist, as shown as the deformed pouch 2'. Likewise, the second conduit member 22' deforms with the pouch 2 to a deformed pouch 2' while staying in place in the deformed pouch 2' because the second conduit member 22' is retained by the conduit member retainer 26' which keeps the second conduit member 22' toward the outer edge of the deformed pouch 2'. Thus, the distal end 20 of the deformed pouch 2' stays relatively straight and taught and does not fold or collapse and the conduit members 18 and 22' are not blocked so that they can still evacuate air and urine. Furthermore, the first wall 4 and second wall 6 can remain relatively adjacent to each other even while the device 1 is loaded and deformed to prevent significant contact, creases, or folding which may stifle the flow of fluids.

One skilled in the art will recognize that there are other arrangements of a conduit system and pouch that provide the structural integrity to keep the fluid flow system operable. Some example embodiments are shown in FIGS. 20-35, but other designs, permutations, and configurations are within the scope of this disclosure. For clarity, the embodiments disclosed herein, in particular the embodiments illustrated in FIGS. 20-35, may not show all of the features, such as air ports, as shown in other embodiments (e.g., FIG. 1) even though they may have these features; emphasis instead being on the differences between the various embodiments.

FIGS. 20-22B illustrate embodiments having different conduit system arrangements. Now with reference to FIG. 20, which shows a device 201 having an alternative conduit member arrangement wherein the first conduit member 210 and the second conduit member 211 attach to a suction source tube 214 at the proximal end 213 of the urine removal device 201. In this embodiment, the first conduit member 210 and the second conduit member 211 reside outside of the pouch 202 except near the distal end 212 of the pouch 202 where the first conduit member 210 enters the pouch 202 at a first pouch entry point 219 and the second conduit member 211 enters the pouch 202 at a second pouch entry point 220 so that the distal tips of the first conduit member 210 and second conduit member 211 reside inside the pouch 202 to function similarly to that described above, in urine removal device 1. The pouch 202 may be attached to the first conduit member 210 and the second conduit member 211 continuously along the outer periphery of the pouch 202 or at discrete locations so that the rather flaccid pouch can be supported by the conduit members 210 and 211 to prevent excessive bending and kinking.

Figure 21:
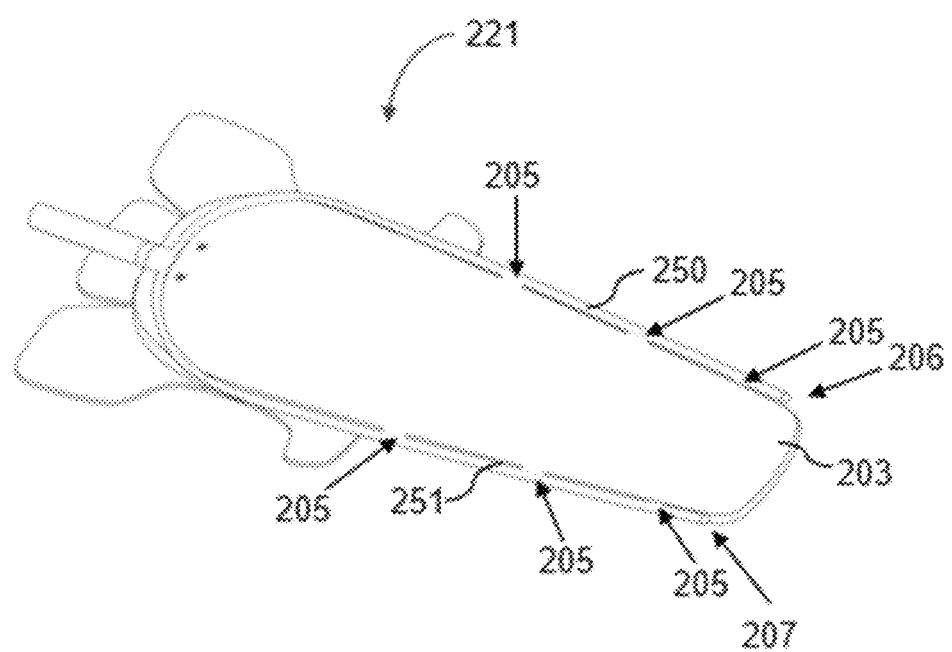
FIG. 21 illustrates a perspective view of a urine removal device having a having external conduit members with one or more inlets according to an example embodiment.

In another embodiment of urine removal device 1, illustrated in FIG. 21, conduit members 250 and 251 are disposed external surfaces to the pouch 203, wherein each conduit member 250 and 251 is in fluid communication with the internal compartment, defined by pouch 203, through one or more connecting channels 205. The distal ends 206 and 207 of the conduit members 250 and 251, respectively, may be external to the pouch 203 and blocked (i.e., no flow in or out).

Figure 22A:
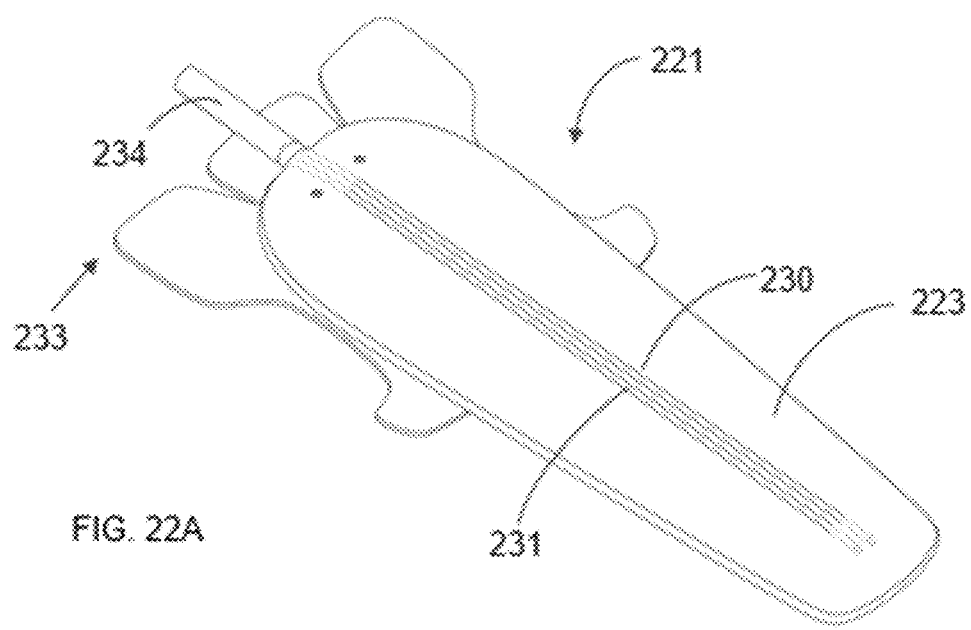
FIG. 22A illustrates a perspective view of a urine removal device having a centrally located conduit member pair according to an example embodiment.
Figure 22B:
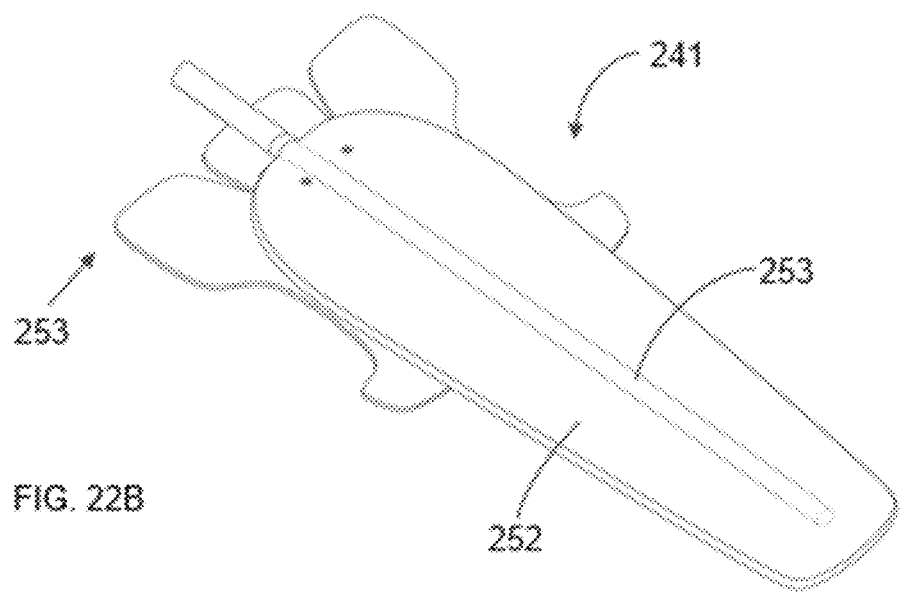
FIG. 22B illustrates a perspective view of a urine removal device having a centrally located conduit member according to an example embodiment.

FIG. 22A illustrates another embodiment of a urine removal device 221 having an alternative conduit member arrangement with a first conduit member 230 and a second conduit member 231 located along the middle of the pouch 223 connecting to the suction source tube 234 at the proximal end 233 of the urine removal device 221. The pouch 223 may be attached to the first conduit member 230 and the second conduit member 211 continuously along the outer periphery of the pouch 222 or at discrete locations so that the rather flaccid pouch can be supported by the conduit members 230 and 231 to prevent excessive bending and kinking. Furthermore, in other similar embodiments, such as the urine removal device 241 shown in FIG. 22B, the conduit system may comprise a single conduit member 253 located along a midline of the pouch 252. In each of the aforementioned embodiments, devices 221 and 241, the conduit members may run entirely inside of the pouch or may be located partially outside of the pouch except where the distal tips reside at the distal end inside of the pouch.

Figure 23A:
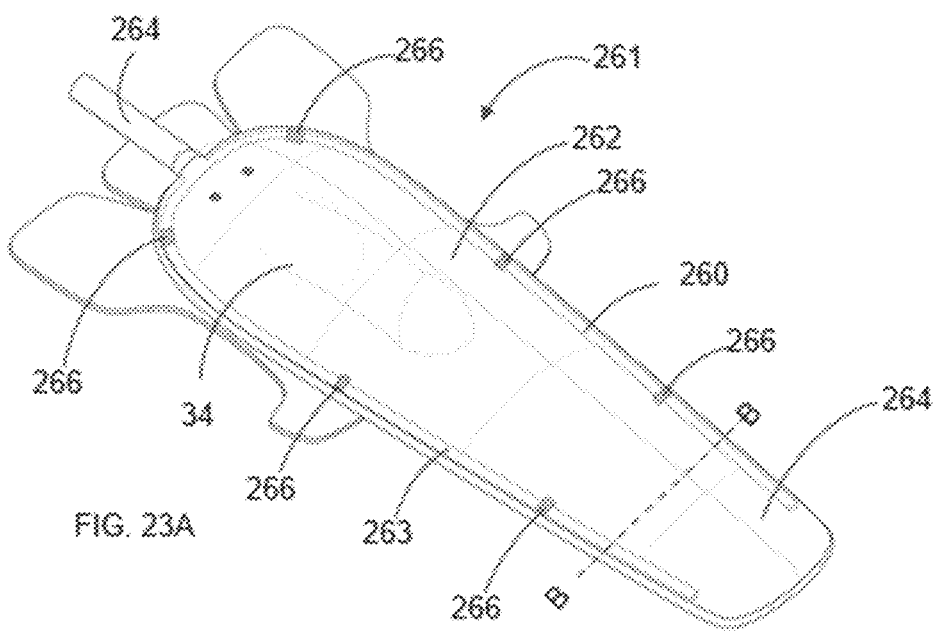
FIGS. 23A-23C illustrate a perspective view, a side view, and a sectional view respectively of a urine removal device according to another example embodiment.
Figure 23B:
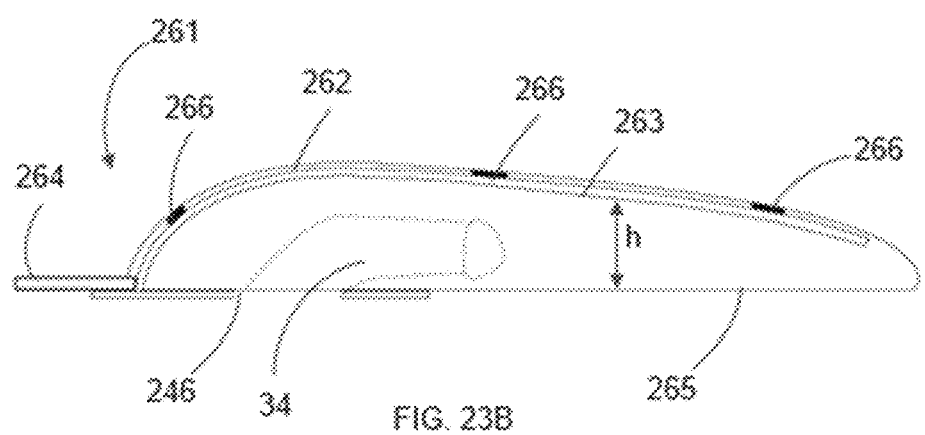
Figure 23C:
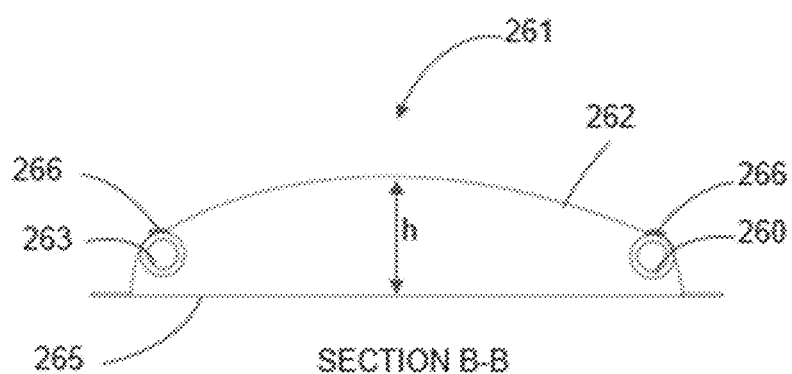
Figure 24:
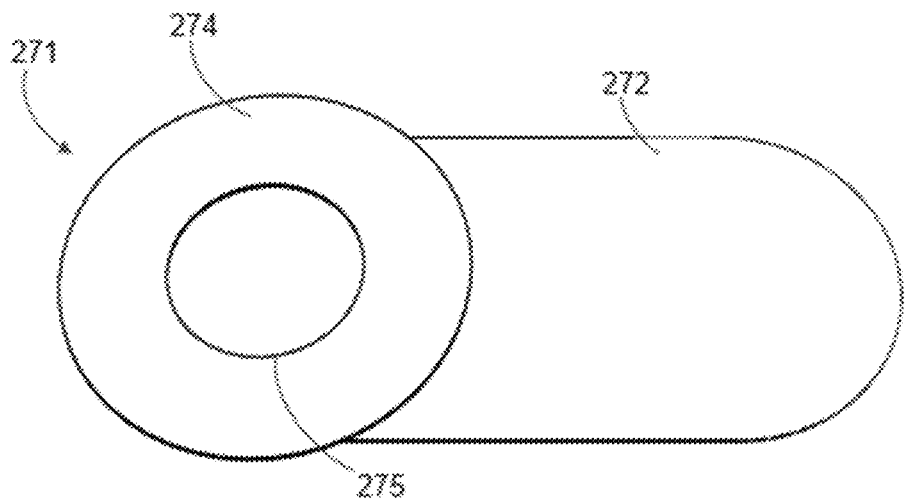
FIG. 24 illustrates a bottom view of a urine removal device according to an example embodiment.

In some embodiments, the pouch may have a domed profile such that the first wall of the pouch is spaced away from the inner layer, either due to the penis propping the pouch up or by the structure of the pouch creating an open cavity inside of the pouch as shown in FIGS. 23A-23C. As illustrated in FIG. 23A, the urine removal device 261 has a first conduit member 260 and a second conduit member 263, both of which are attached to the first wall 262 of the pouch 264 with conduit member attachments 266 which may, for example, be adhesive bonds or thermal welds (i.e., heat stakes). In this embodiment, the conduit members 260 and 263 are curved out of plane so that the first wall 262, which is attached, is tented away from the second wall 265 by a height "h" as shown in FIG. 23B. This allows the first wall 262 to reside above the penis 34 as shown, or depending on the height "h," the first wall 262 it may still contact the penis 34 but may do so with relatively low contact force due to the domed shape. FIG. 23C is a cross-sectional view through plane B-B in FIG. 23A. FIG. 23C illustrates how the first conduit member 260 may be attached to the first wall 262 via a conduit member attachment 266 and similarly the second conduit member 263 may be attached to the first wall 262 via a conduit member attachment 266; the conduit member attachments 266 may be located on the top, the side, or anywhere around the circumference of the conduit member. Embodiments, such as that shown in FIGS. 23A-23C, where the first wall 262 is attached directly to the conduit members 260 and 263, may provide more interior pouch internal space as compared to embodiments wherein the conduit members are enveloped by the walls (e.g., see FIG. 1D) because in the former, the pouch walls 262 and 265 are not tacked together inboard of the pouches, leaving a more open interior space.

There are many other embodiments of urine removal devices having various architectures that are within the scope of this disclosure and various combinations of those included herein are contemplated. By way of nonlimiting example, some of these are shown in the figures. For example, one embodiment is shown in a view from the inner side, that is, the patient-facing side, in FIG. 24. The urine removal device 271 has a relatively simple design having relatively fewer parts, including a pouch 272 and a round adhesive patch 274 surrounding an aperture 275.

Figure 25:
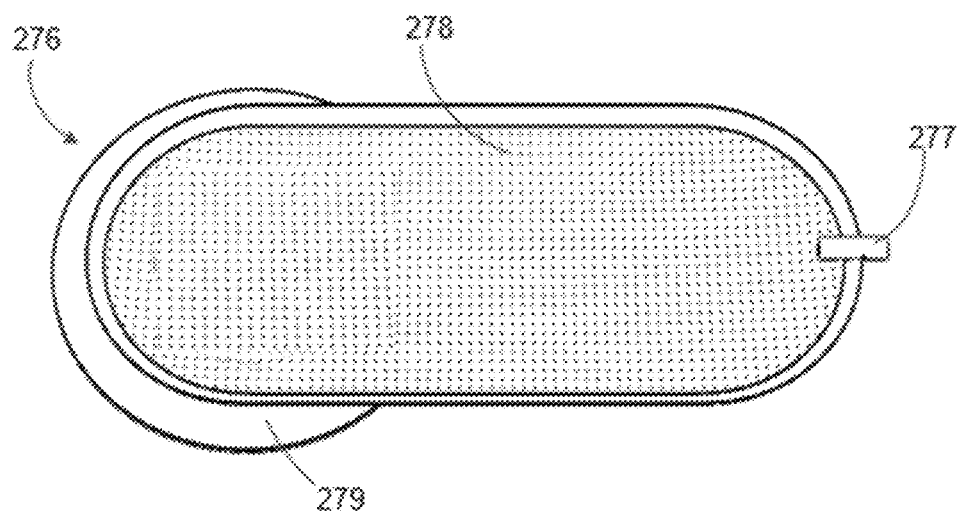
FIG. 25 illustrates a top view of a urine removal device according to another example embodiment.
Figure 26:
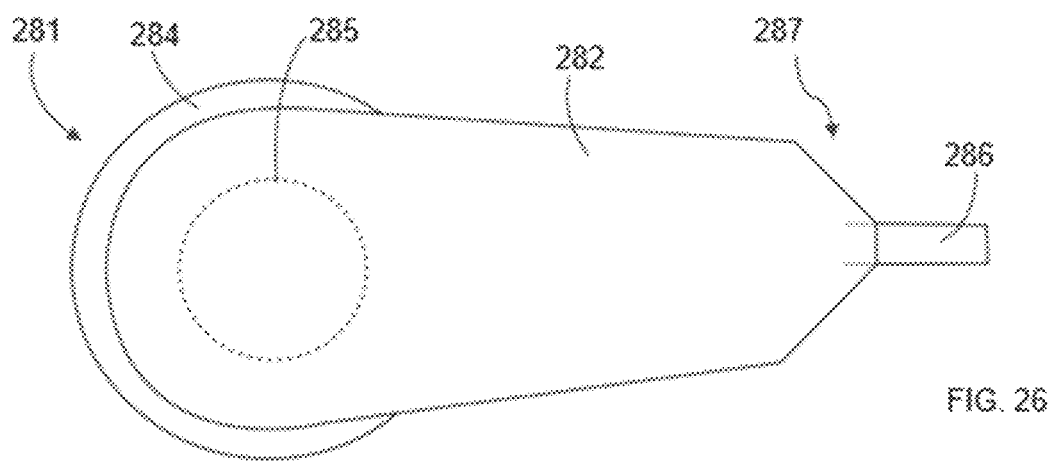
FIG. 26 illustrates a top view of a urine removal device according to another example embodiment.
Figure 27:
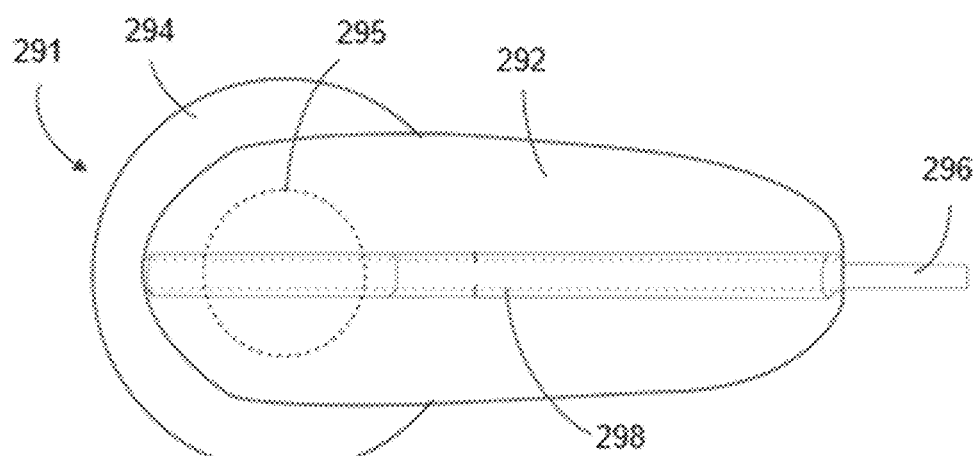
FIG. 27 illustrates a top view of a urine removal device according to another example embodiment.
Figure 28:
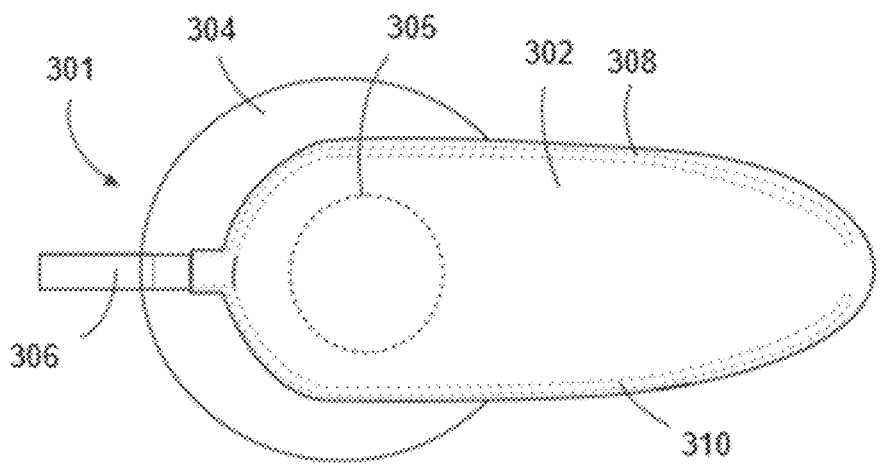
FIG. 28 illustrates a top view of a urine removal device according to another example embodiment.

Another embodiment is shown in FIG. 25, the urine removal device 276 having an adhesive patch 279 attached to a pouch 278 which includes a suction source tube 277 at the distal portion of the pouch 278 that can be connected to a vacuum source to provide suction to the interior of the pouch 278. A similar urine removal device 281, as shown in FIG. 26, has a pouch 282 that is tapered toward the distal end 287 where a suction source tube 286 is attached. The device 281 may have an adhesive patch 284 that is round, encircling an aperture 285 where the penis enters the pouch 282 in a similar fashion to other embodiments disclosed herein. In yet another embodiment, FIG. 27 shows a urine removal device 291 with a similar layout to the device of FIG. 26 with an adhesive patch 294 that is round, encircling an aperture 295 where the penis enters the pouch 292; this embodiment includes a gusset 298 arranged along the longitudinal axis or at some angle from the proximal to the distal end of the pouch 292. The gusset 298 includes at least one pleat, which is folded as the pouch 292 lays flat, but may open/unfold to increase surface area and internal compartment as the pouch 292 expands due to air or fluid that may accumulate inside of the pouch 292. A suction source tube 296 is located at the distal end and in fluid communication with the pouch 292. Another embodiment is shown in FIG. 28; the urine removal device 301 having an adhesive patch 304 that is round, encircling an aperture 305 where the penis enters the pouch 302, a suction source tube 306 at the proximal end connecting to a first conduit member 308 and a second conduit member 310 both of which extend to the distal end 309 of the pouch 302 where they curve toward the center of the pouch 302 to conform to the tapered shape of the pouch 302.

Figure 29:
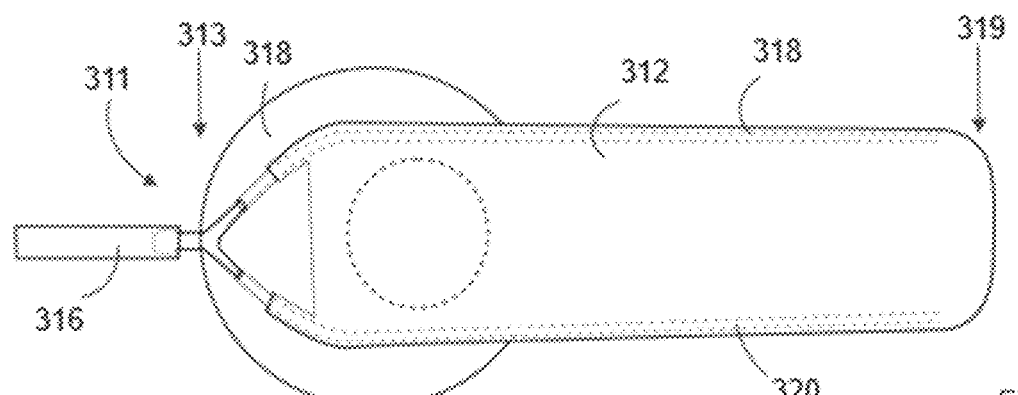
FIG. 29 illustrates a top view of a urine removal device according to another example embodiment.
Figure 30:
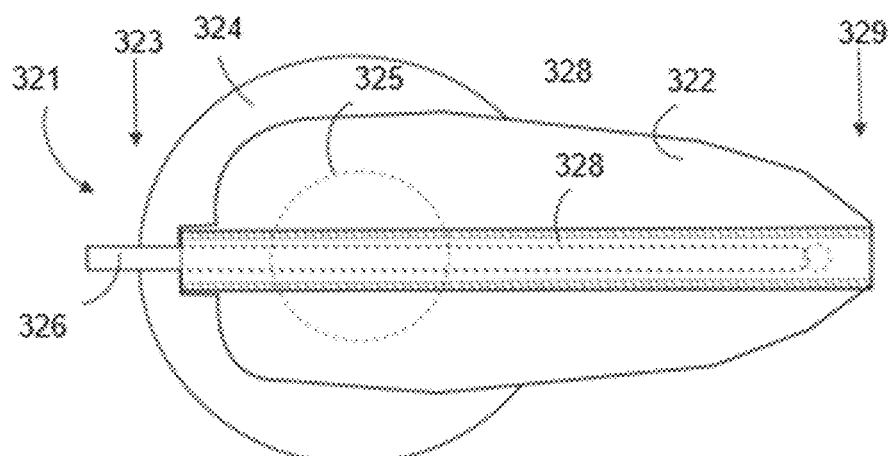
FIG. 30 illustrates a top view of a urine removal device according to another example embodiment.
Figure 31:
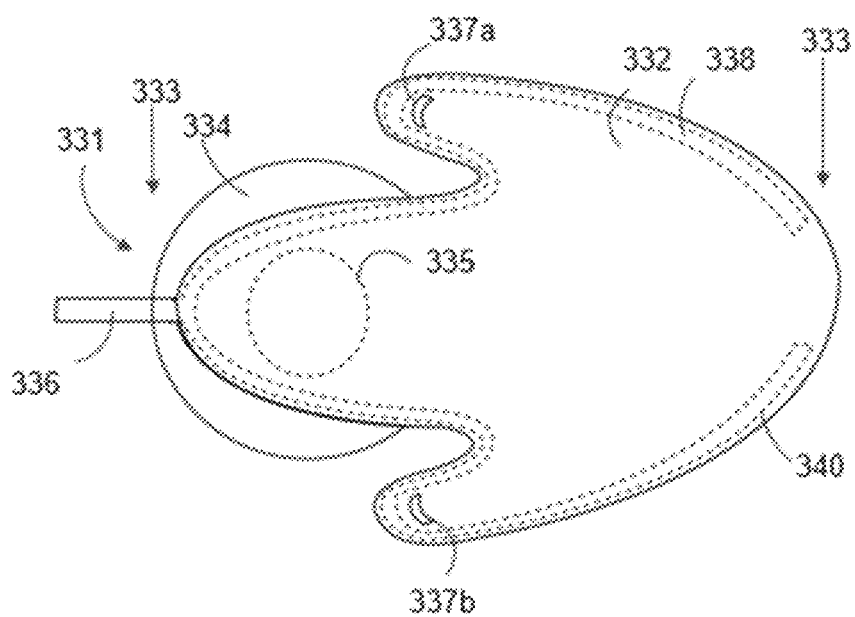
FIG. 31 illustrates a top view of a urine removal device according to another example embodiment.

Now with reference to FIG. 29 another embodiment of a urine removal device 311 is illustrated having a suction source tube 316 at its proximal end 313 that fork or wishbone external to a pouch 312 into a first conduit member 318 and a second conduit member 320, both of which extend to the distal end 319 of the pouch 312 which has a blunt, flat end. In this another embodiments, the conduit system provides a relatively stiff frame that provides structure to the device 311 to prevent excessive bending, twisting, buckling, and creasing, which may slow the flow of urine. FIG. 30 shows another embodiment of a urine removal device 321 having a suction source tube 326 at the proximal end 323 that attaches to a conduit member 328 that extends along the axis of the pouch 322 to the distal end 329 of the pouch 322. The device 321 has an adhesive patch 324 that is circular, the adhesive patch 324 having an aperture 325 providing access to the pouch 322. Another embodiment of a urine removal device 331 having wings is shown in FIG. 31. The device 331 includes a pouch 332 having a first wing section 337a and a second wing section 337b on the opposite side. Similar to other embodiments, the device 331 may include a suction source tube 336 attached to a first conduit member 338 and a second conduit member 340 both of which terminate near the distal end 333 of the pouch 332. The conduit members 338 and 340 may extend along the periphery of the pouch 332 conforming to the wing shape as shown to provide structural support to retain the shape of the pouch. An adhesive patch 334 may be disposed on the pouch 332, and an aperture 335 protrudes through the adhesive patch 334 and the pouch 332 to provide access to the inside of the pouch 332. In some circumstances, the device 331 may reside sideways either because the patient is on his side, or because the device 331 is laying sideways, for example between the patient's legs. In such cases, urine within the pouch 332 may pool in one of the wings (337a and 337b) due to gravity, and once in the wing, the urine can be captured so that it does not traverse proximally or medially such that it contacts the penis. In this sense, the wings 337a and 337b tend to shield the penis from the urine when the device 331 is oriented sideways.

Figure 32:
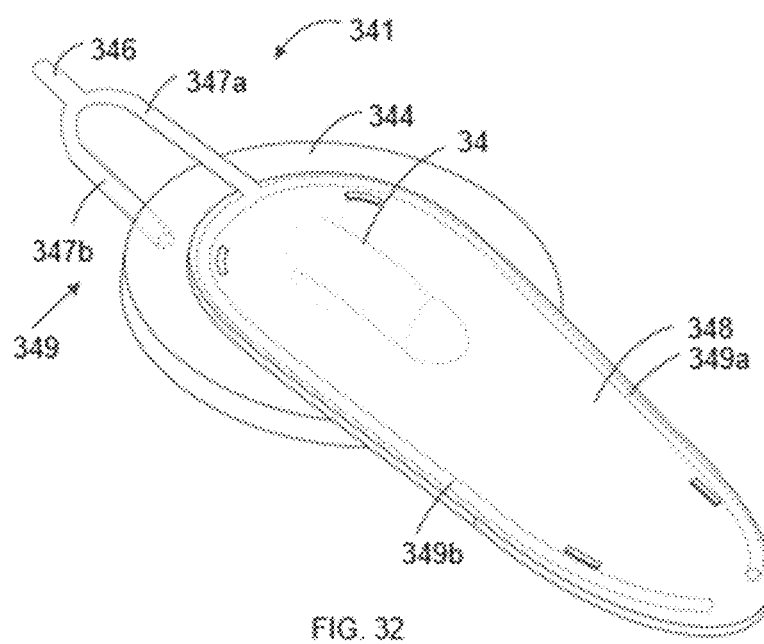
FIG. 32 illustrates a top view of a urine removal device according to another example embodiment.

Now with reference to FIG. 32 which shows a urine removal device 341 having a suction source tube 346 at its proximal end 349; the suction source tube 346 bifurcates into two channels forming a pouch conduit member 347a and an attachment conduit member 347b. The pouch conduit member 347a is a conduit to provide vacuum to the pouch 348 similar to other embodiments disclosed herein (e.g., FIG. 1) in that it connects to a first conduit member 349a and an opposing second conduit member 349b to draw out air, urine, and vapor as disclosed herein. The conduit member 347b is connected to a body attachment 344 which, like the adhesive patches disclosed herein, may have an adhesive for adhering to the body. However, in this embodiment, the body attachment 344 may have air flow channels in fluid communication with the skin to draw the body attachment 344 to the body so that the device 341 stays adhered to the body around the penis 34. reducing the risk of urine leakage In this and other embodiments disclosed herein, the suction pressure can be regulated or calibrated to provide enough vacuum to remove moisture from the pouch without having excessive suction that may cause discomfort, sensation, or necrosis on the penis or surrounding skin. Such regulation may be accomplished by adjusting the care facility's vacuum source, adjusting the vacuum pump operatively attached to the urine removal device, or providing a valve or other flow restrictor on the suction source tube or any tubes or apparatus' in fluid communication with the suction source tube. In embodiments, the suction source tube may not be a tube, but may be a fitting or connector directly attached to the pouch and providing fluid communication between an inner cavity of the pouch (or conduit members or channels) and the outside of the pouch.

In various embodiments, the conduit members may be made of any suitable polymeric material. Nonlimiting examples of thermoplastics include polyethylene, HDPE, polypropylene, polyethylene terephthalate, polyamide, polyvinyl chloride, polyester, polyether, polyurethane, and block-copolymer elastomers. Nonlimiting examples of thermoset polymers/rubbers include butyl, chloroprene, epichlorohydrin, ethylene/acrylic, ethylene-propylene, fluorocarbon, fluorosilicone, silicone rubber, natural rubber, nitrile, hydrogenated nitrile, perfluoroelastomer, polyacrylate, polysulfide, polytetrafluoroethylene, and styrene butadiene. The conduit members may be sized such that they do not take up excessive space in or around the pouch but they are large enough to provide adequate support to prevent the pouch from kinking or bending excessively as described elsewhere in this disclosure. As such, the inner diameter of the tubes may be from approximately 1 mm-9 mm and the outer diameter may be from 2 mm-10 mm while the wall thickness may be in a range from 0.5 mm-5 mm or the wall thickness may be about 15-25% of the outer diameter in some embodiments. More particularly, in some embodiments, the conduit members may have an inside diameter of about 2.8 mm and an outside diameter of about 3.9 mm, while the suction source tube may have an inside diameter of 6.5 mm and an outside diameter of about 8.5 mm. The durometer of the conduit members may be approximately 35-85 Shore A in some embodiments.

Figure 33A:
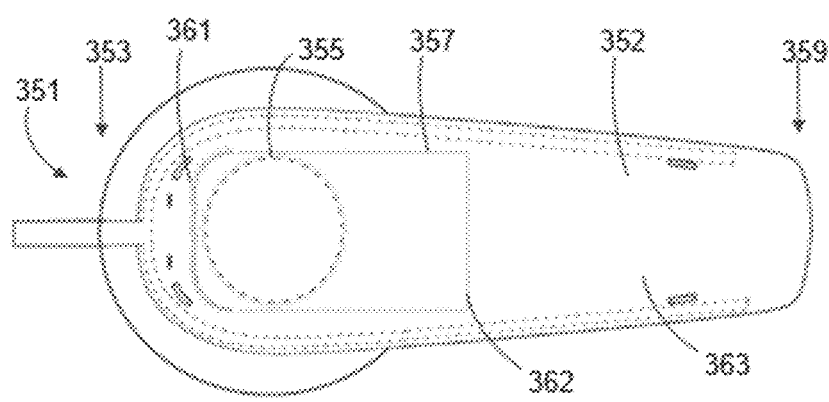
FIG. 33A illustrates a top view of a urine removal device having a flap over the pouch aperture acting as one-way valve according to an example embodiment.
Figure 33B:
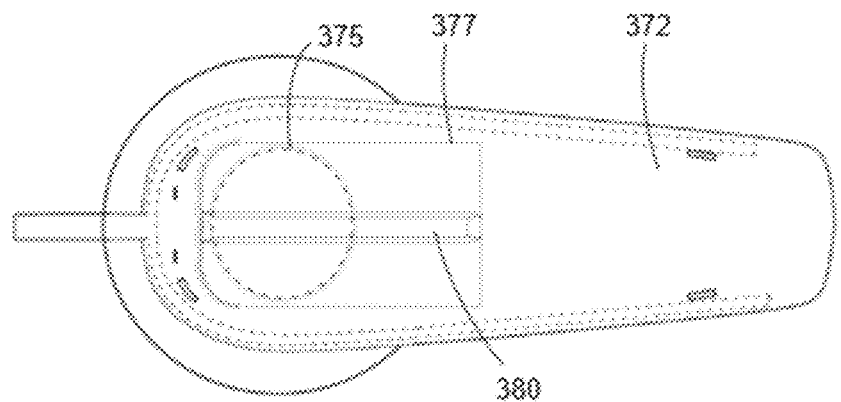
FIG. 33B illustrates a top view of a urine removal device having a flap with a gusset acting as one-way valve according to another example embodiment.

FIGS. 33A-33B illustrate embodiments having a sleeve that covers the penis inside of the pouch, such that the sleeve serves like a flutter valve to prevent backflow of urine. The urine removal device 351 has a sleeve 357 with a proximal end 361 that is closed and has an aperture that is attached to the aperture 355 of the pouch 352 (to the inner wall, not shown, of the lower layer of the device 351) where it may be joined by any suitable method of joining polymers such as gluing, bonding or thermal bonding (e.g., heat staking). The sides of the sleeve 357 may also be partially attached to the pouch in some embodiments. The sleeve 357 covers the aperture 355 to the pouch 352 and extends over the penis (not shown), which protrudes through the aperture 355. The distal end 362 of the sleeve 357 is open such that it may reside against the two walls of the pouch 352 but when fluid bears upon it from the proximal end, that is from the penis, the sleeve 357 can gap open and allow urine through to the distal end 359 of the pouch 352. However, if urine bears upon it from the distal end 359, the sleeve 357 will tend to close around the penis as the force of the urine causes the sleeve 357 to bear down itself. This action is similar to that of a flutter valve. In FIG. 33A, the second wall is not shown because it is below the first wall 363 of the pouch 352, as the pouch 352 is otherwise similar to other embodiments discussed herein and, for example, shown in FIG. 1. The embodiment shown in FIG. 33B is similar to that shown in FIG. 33A, having a sleeve 377 attached to the pouch 372. However, the sleeve 377 has a gusset 380 that may be a pleat or a fanfold. The gusset 380 tends to unfold laterally when the sleeve 377 is pressed outward, such as forced by the penis as it passes through the aperture 375, or by flowing urine; the unfolding increases the surface area of the sleeve 377 and hence increases coverage over the penis to shield it from the backflow of urine.

Figure 34:
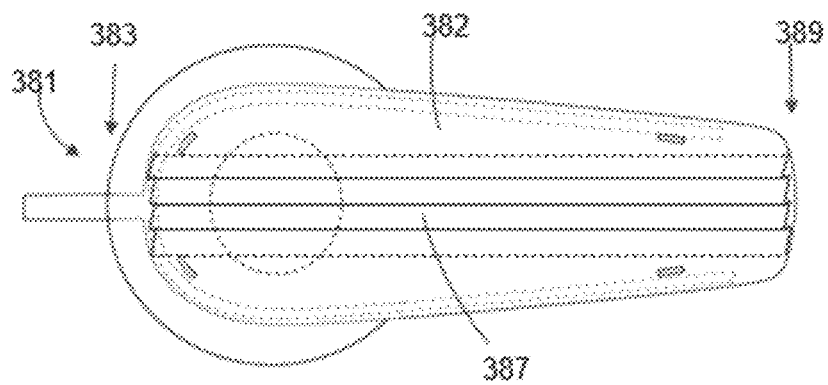
FIG. 34 illustrates a top view of a urine removal device having a pleat or pleats on the pouch according to an example embodiment.

Another embodiment having a gusset in the outer wall of the pouch is shown in FIG. 34. The urine removal device 381 shown may have a gusset 387 extending down a midline from the proximal end 383 of the pouch 382 toward the distal end 389 of the pouch 382. The gusset 387 may be constructed as a single or multiple pleat, or fanfold, that serves to increase the surface area of the pouch 382 as the pouch 382 expands due to, for example, insertion of the penis, air, gas, or urine pressure from within the pouch 382. Notably, the gusset 387 may make it easier for the operator to install the device 381 on the patient because the pleats enhance the ability of the operator to manipulate the device 381 around the penis while attaching it.

Figure 35:
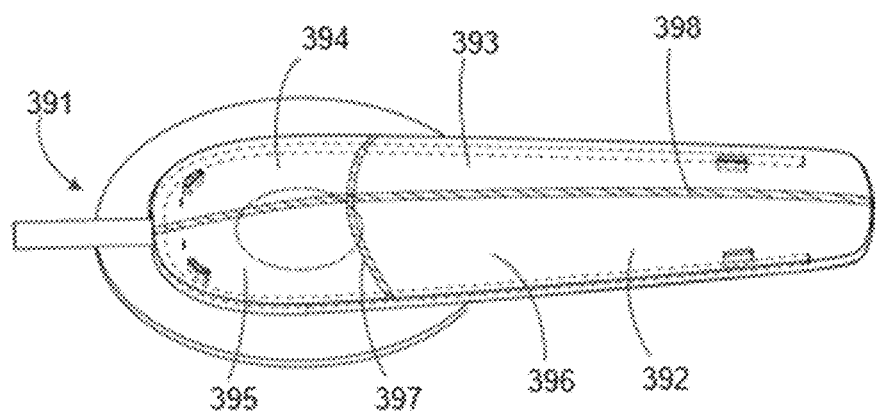
FIG. 35 illustrates a perspective view of a urine removal device having a pouch with a domed shape according to an example embodiment.

An embodiment having a domed pouch shape is illustrated in FIG. 35. The urine removal device 391 has a pouch 392 which has a first wall that is divided into multiple sections, for example, four sections in this embodiment, a first section 393, a second section 394, a third section 395, and a fourth section 396 that are joined together through a longitudinal seam 398 running proximal to distal along the pouch 392, and a lateral seam 397 running transversely across the pouch 392. The sections may be fabricated by cutting them in specific two-dimensional shapes having curved or straight edges, such that when they are joined via the seams, they form a domed shape as illustrated in the pouch 392. The domed shape provides space inside of the pouch 392 to reduce or eliminate contact of the pouch 392 with the penis. One skilled in the art will recognize that, depending on how the sections are shaped, the pouch 392 may have a tent-like shape with substantially flat sections rather than a dome shape that is typically substantially curved.

Figure 36:
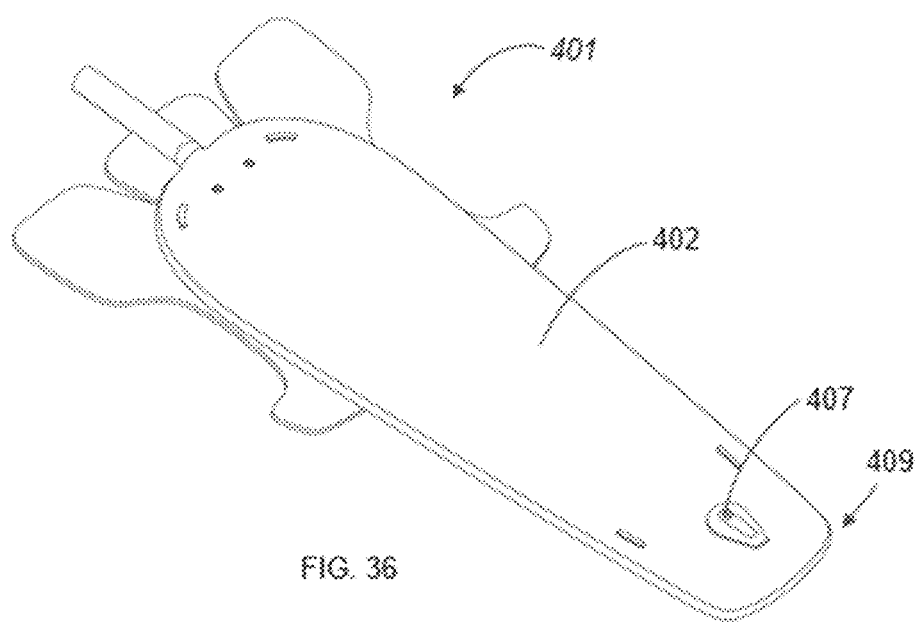
FIG. 36 illustrates a perspective view of a urine removal device having a urine sample port according to an example embodiment.

In some circumstances, it may be desirable to easily acquire a sample of urine for analysis, for example, for testing pH, or testing for nitrates or bacteria. A urine removal device 401 having a urine sample port 407 is shown in FIG. 36. The urine sample port 407 is located on the pouch 402 and it may capture urine from the pooled urine in the pouch 402. In some embodiments, the urine sample port 407 may be a module that can be removed from the pouch 402 after it is at least partially filled with urine, and periodic sampling may be conducted by inserting an empty module to replace the used module; after a period of time, the new module will be exposed to urine and it may be removed for sampling. In other embodiments, the urine sample port 407 may be a self-sealing membrane that can be punctured with a needle to aspirate a small amount of urine. In other embodiments, a sensor may also reside in the port to measure a physical or biological metric such as temperature, sediment, weight, color, blood, bacteria, or specific gravity for example. The sensor may be in contact with the fluid or the air/vapor space inside of the pouch depending on the type of sensor and metric being measured. The sensor may measure pressure, moisture, humidity, weight in the pouch, or any other relevant metric relevant for urinary incontinence patients. The sensor output may be used to automatically control the vacuum source by changing the applied pressure or turning it on or off, for example. While the urine sample port 407 is shown located toward the distal end 409 of the device 401, in other embodiments, it may be located in any other location such as on the proximal or middle region of the pouch 402.

Body Attachment

In the embodiments disclosed, the urine removal device may be attached at the base of the penile shaft, scrotum, and abdomen. There are several advantages and challenges of having an interface that is affixed on the groin, pelvic and abdominal region. In addition to the shape of the adhesive, the shape of the orifice, method of application (different peel points), and material of the adhesive may be tailored to this area of anatomy.

Due to a combination of factors, external collection systems face challenges with patient attachment as well as dislodgement. Variation in patient anatomy creates challenges in a one-size-fits-all solution. Genital skin is sensitive and prone to pain, which limits the strength of adhesive able to be used. The abdominal and genital region may also have various creases and folds that are unique to each patient. Movement of legs and hips causes significant bending, elongation, and compression of genital and perineal skin, requiring unique functions of both the adhesive and connected materials. Lastly, temporary containment of urine inside of an enclosed space increases weight, and subsequent force, acting on the adhesive, exacerbating the risk of dislodgement.

Figure 37A:
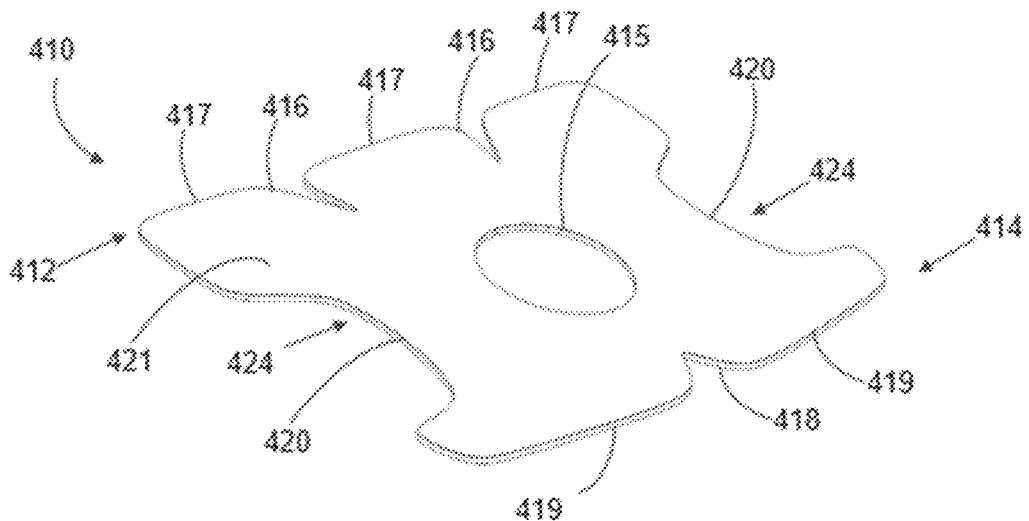
FIG. 37A illustrates a perspective view of an adhesive patch according to an example embodiment.

An embodiment of an adhesive patch 410 is illustrated in FIG. 37A. The adhesive patch 410 has an aperture 415 suitable to fit over the shaft of a penis and a wide proximal end 412 and a wide distal end 414, which attach to the lower abdomen and scrotum respectively, as shown in FIG. 2C. In embodiments, the adhesive patch 410 may have a narrowed central section 424 defined by concave sidewalls 420 as shown in FIG. 37A. The wide proximal end 412 provides a large surface area to improve adhesion to the body while stabilizing against twisting motions where it attaches to the suprapubic region. The width of the proximal end 412 may be approximately 15 cm across or between 2 and 30 cm across in embodiments. The proximal end 412 may have one or more slits 416 dividing the adhesive patch 410 into proximal tabs 417. Likewise, the distal end may have at least one slit 418 dividing the adhesive patch 410 into distal tabs 419. The slits 416 and 418 can reduce tension or compression of the adhesive patch 410 during body movement by providing a relief between each section of attached skin that is deforming, thus allowing the adhesive patch 410 to deform with the body without excessively resisting the motion which can cause discomfort or lead to dislodgement. The slits 416 and 418 may be straight cuts or, as shown, they may be approximately "v" shaped or any other shape, and in some embodiments having rounded corners to be more gentle and atraumatic to the skin.

The distal end 414 may be narrower than the proximal end 412 so that it fits onto the scrotum. The width of the distal end 414 may be approximately 14 cm across or, for example, from 2 cm to 30 cm in some embodiments.

The proximal end 412 and the distal end 414 attach to the suprapubic region and scrotum respectively, while the central section 424 lays around the penile shaft. As such, the central section 424 is narrower than the proximal end 412 and distal end 414 of the adhesive patch 410. The central section 424 may be approximately 9 cm across or from 5 cm to about 20 cm in some embodiments. The topology consists of rather variable surfaces in the anatomy in the region of the central section 424 so the reduced width can lessen the contact, and therefore the forces transferred, due to movement of, for example, the legs or scrotum, which can reduce the incidence of dislodgment of the adhesive patch 410. Furthermore, when the adhesive patch is applied around the penile shaft, the operator may press the large surface areas of the adhesive patch 410 onto the large surface areas of the body, for example by pressing the wide proximal end 412 onto the suprapubic region and the somewhat less wide distal end 414 onto the scrotum, while the central section 424 seats down around the shaft of the penis. The narrow, concave shape of the central section 424 facilitates this section seating deep enough to seat against the skin adjacent to the shaft of the penis without hanging up or being held back by the adjacent skin which has a relatively topology in the pubic region.

Figure 37B:
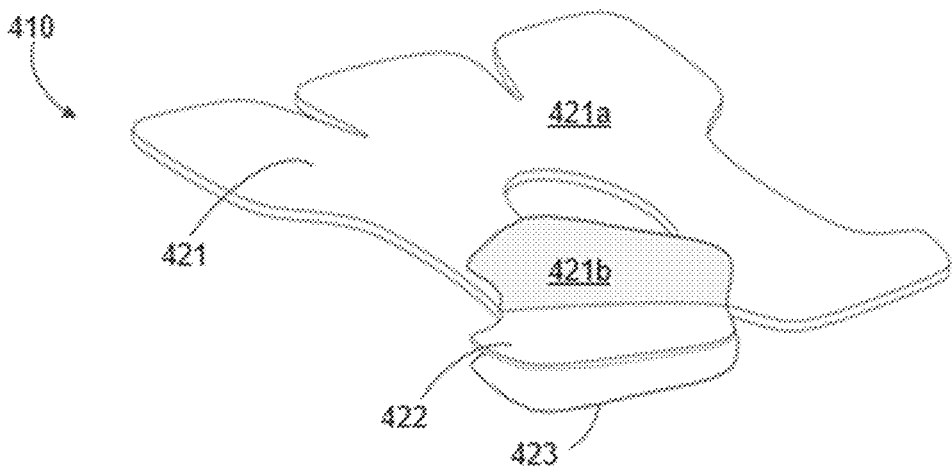
FIG. 37B illustrates a perspective view of the adhesive patch of FIG. 37A showing various layers according to an example embodiment.

FIG. 37B shows the adhesive patch 410 with the layers separated on a corner to more clearly show the different layers in this embodiment. The substrate layer 421 is a fixed layer in that it is permanently attached to the pouch (not shown, but see FIG. 1B) on its outer surface 421a and it is attached to the adhesive layer 422 on its inner surface 421b. The adhesive layer 422 may comprise a single adhesive layer or a layup of a plurality of layers configured to conform with skin on one side and the substrate layer 421 on the other side. The substrate layer 421 may be coupled to the pouch by thermal welding (heat staking), bonding with solvents or adhesives, or any other method for attaching thin layers. The substrate layer 421 is generally provided coupled to the pouch so that the adhesive patch 410 is already in place, but, in some embodiments, it may be provided uncoupled so that the operator attaches it to the pouch before use. The substrate layer 421 may be made of any material that allows it to adhere to both the adhesive layer 422 and the pouch; examples include but are not limited to a single or a mixture of a natural or thermoplastic or thermoset polymer in sheet, film, woven or non-woven fabric form; example materials include polyethylene, polypropylene, thermoplastic elastomer (TPE), polyurethane, EVA (ethylene-vinyl acetate), nylon, rayon, etc. In some embodiments, the substrate layer 421 may have a peel strength (relative to the adhesive layer 422) greater than 0.1N/cm.

The adhesive layer 422 is sandwiched between the substrate layer 421 and the release liner 423. The inner surface 422b (not shown) of the adhesive layer 422 is suitable for attachment to the body in the areas surrounding the penis including the scrotum, groin, and suprapubic area. The adhesive layer 422 is amenable to adhesion and removal from skin even with hairs emanating from the skin, while being flexible enough to move with the skin without peeling off. The peel strength with respect to steel can be approximately 0.1-5 N/cm in some embodiments. One skilled in the art will recognize that there many candidate materials that will adhere to the skin for the duration of urine capturing, adhere to the substrate layer 421, be easily removable without excessively pulling on the skin and hair, and leave behind little or no residue on the skin. For example, porous or nonporous silicone adhesives may be particularly suitable as they are comfortable to the patient and may leave no perceptible residue. Other candidate materials include pressure-sensitive adhesives, namely a variety of rubber-based materials, gel-matrix type adhesives like hydrocolloids and hydrogels, and thermoplastic-based adhesives including polyurethanes and acrylics as well as natural adhesive obtained from various plants or animals.

The release liner 423 covers and protects the adhesive layer 422 before use, that is, during manufacturing, shipping, and handling. The release liner 423 should be easy to release from the adhesive layer 422 so that the adhesive does not stretch and rebound when the operator peels the layers apart, as this may cause the adhesive patch 422 to fold and stick to itself. The release liner 423 should have a peel strength away from the adhesive that is less than both the peel strength between the adhesive layer 422 and the substrate layer 421, and less than the peel strength between the substrate layer 421 and the pouch. One skilled in the art will recognize that there are many candidate materials that are suitable to protect the adhesive layer 422 in such a way, such as, for example, paper-based liners including different combinations of coated and densified kraft papers and laminated papers, or film-based liners such as high-density polyethylene and polyester thermoplastics. Additionally, the use of release agents along with the release liners may be used.

Figure 38:
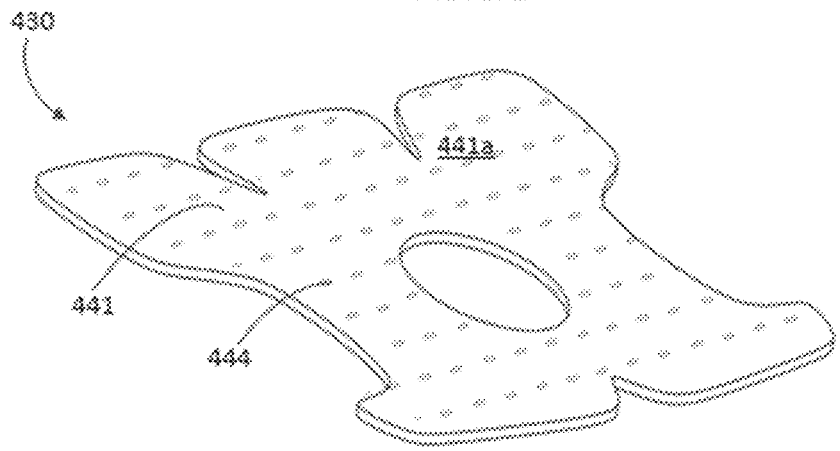
FIG. 38 illustrates a perspective view of an adhesive patch having perforations according to another example embodiment.
Figure 39:
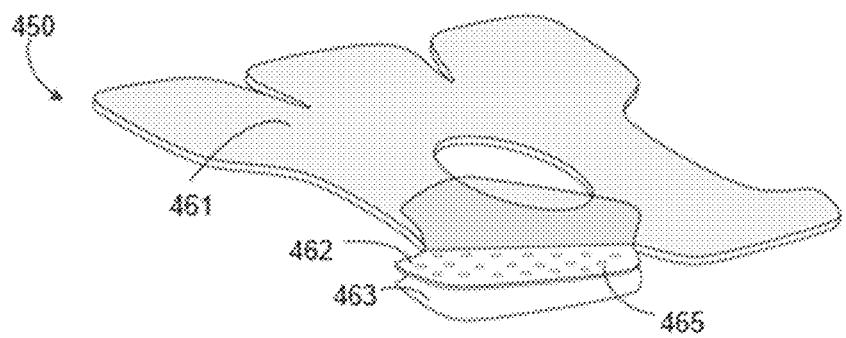
FIG. 39 illustrates a perspective view of an adhesive patch having perforations showing various layers according to another example embodiment.
Figure 40:
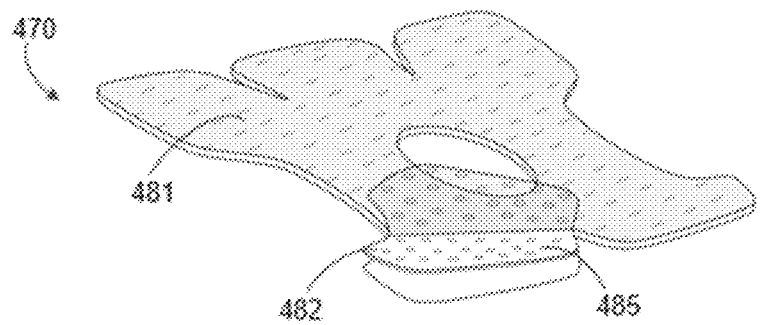
FIG. 40 illustrates a perspective view of an adhesive patch having perforations showing various layers according to another example embodiment.

One or more of the layers in the adhesive patch may be perforated to allow sweat to evaporate, which tends to reduce skin maceration. With reference to FIG. 38, an adhesive patch 430 is shown having a substrate layer 441 with perforations 444 shown in the outer surface 441a; in this and the following figures, while the reference numeral points to one perforation shown, it pertains to the entire array of perforations shown. The perforations 444 may channel through the entire thickness of the substrate layer 441. Alternatively, only the adhesive layer 462 may be perforated 465, as shown in FIG. 39, for improving sweat evaporation. In this adhesive patch 450, the substrate layer 461 is not perforated and the release liner 463 need not be perforated. Finally, as shown in FIG. 40, the adhesive patch 470 both the substrate layer 481 and the adhesive layer 482 have perforations 485 to further enhance sweat evaporation from the skin.

Figure 41A:
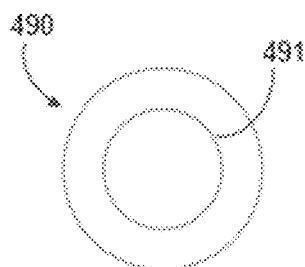
FIGS. 41A-L illustrates various adhesive patch shapes according to example embodiments.
Figure 41B:
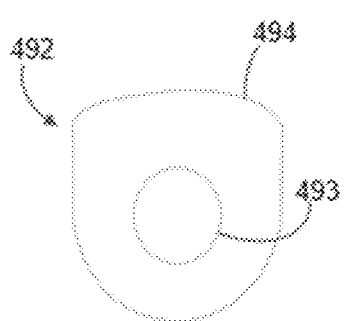
Figure 41C:
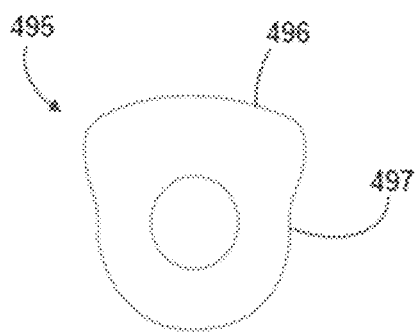
Figure 41D:
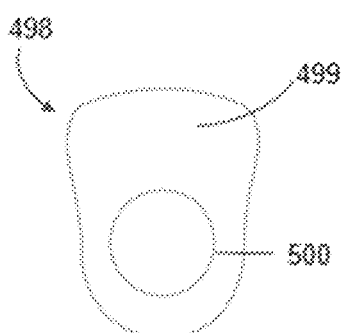
Figure 41E:
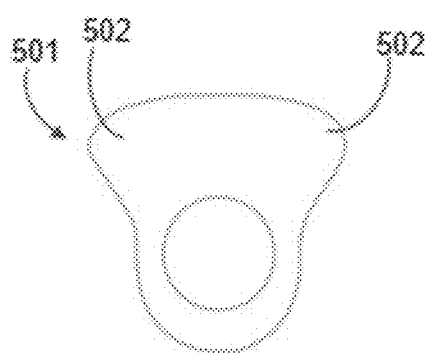
Figure 41F:
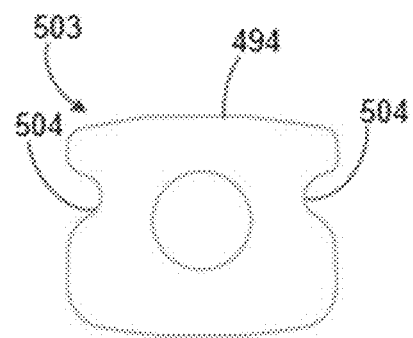
Figure 41G:
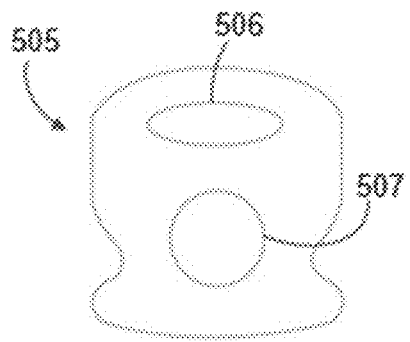
Figure 41H:
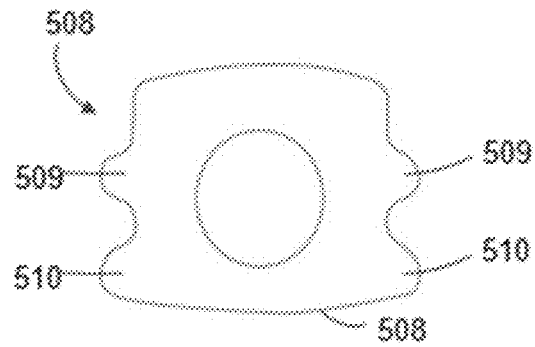
Figure 41I:
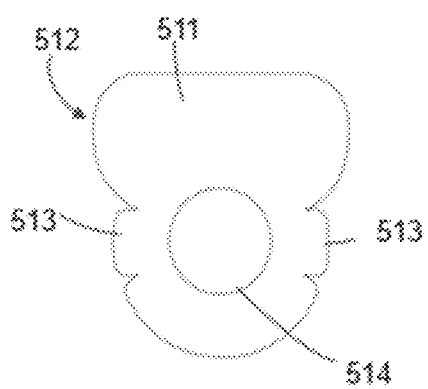
Figure 41J:
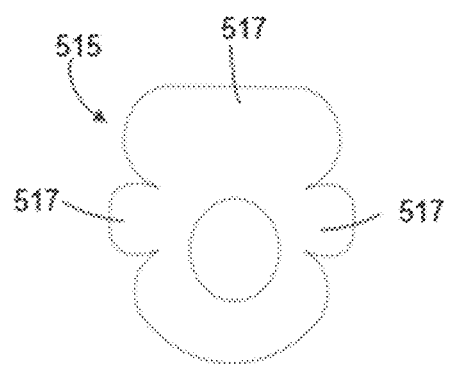
Figure 41K:
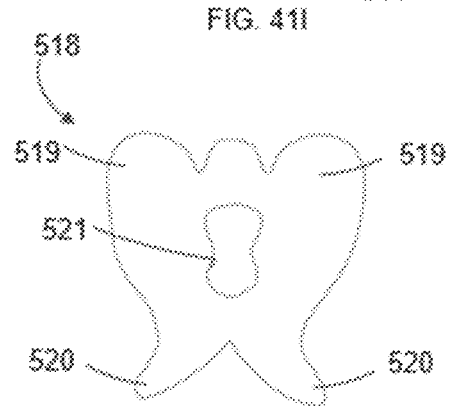
Figure 41L:
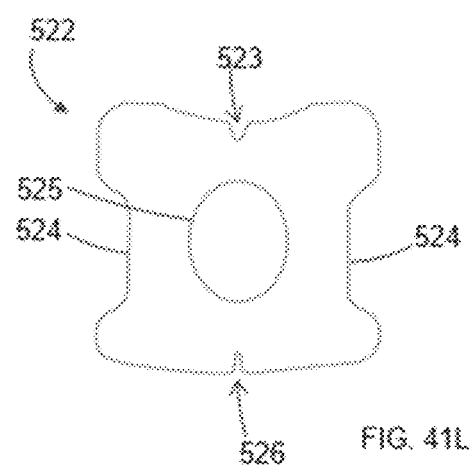
Figure 42:
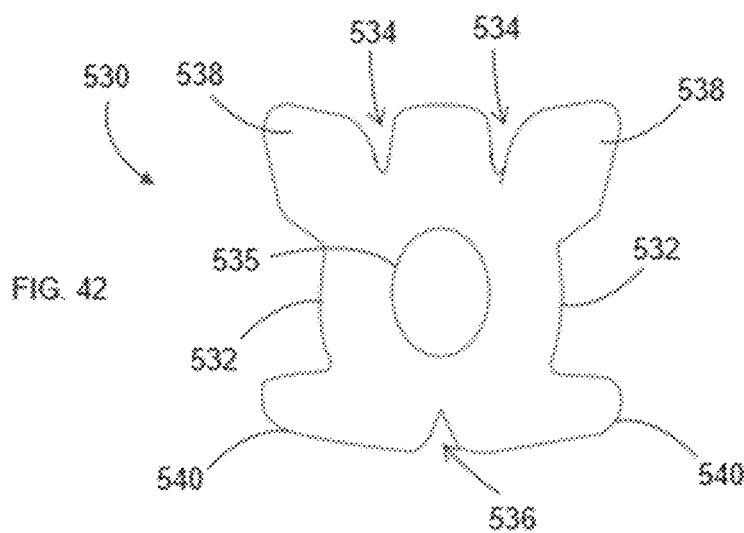
FIG. 42 illustrates an adhesive patch shape according to another example embodiment.

One skilled in the art will recognize that there are many different shapes of the adhesive patch that can be effective to fit within the anatomy around the penis and attach to the suprapubic area and the scrotum while not excessively interacting with the legs and groin area, in what is a geometrically complex area of the male anatomy. FIGS. 41A-L illustrate several embodiments having various shapes as nonlimiting examples; in the examples, the aperture identified designates the region through which the penis is placed for entry into the pouch and proximal is upward on each figure. FIG. 41A shows an adhesive patch 490 that is circular and centered around an aperture 491. FIG. 41B shows an adhesive patch 492 having a proximal section 494 that is high and broad and a distal section that is round, while the adhesive patch 495 of FIG. 41C similarly has a proximal section 496 that is high and broad but has scalloped sides 497. The adhesive patch 498 shown in FIG. 41D has a shape that is narrow around the aperture 500 with a high proximal section 499 opposed by a round distal end. The adhesive patch 501 shown in FIG. 41E has a high and broad proximal section with proximal flanges 502 and a round distal end. The adhesive patch 503 shown in FIG. 41F has a wide shape that is short proximally and has scallops 504 on the sides. The adhesive patch 505 has a second aperture 506 above the primary aperture 507, the second aperture being oval and extending laterally wider than the primary aperture 507, as shown in FIG. 41G. The adhesive patch 508 shown in FIG. 41H has a middle set of flanges 509 on each side and a lower set of flanges 510 near the distal end of the patch 508. FIG. 41I illustrates yet another embodiment wherein the adhesive patch 512 has a large, bulbous proximal section 511 and a pair of lateral tabs 513 next to the aperture 514. Similarly, the adhesive patch 515 shown in FIG. 41J has a bulbous proximal section 516 and large tabs 517 extending laterally. The adhesive patch 518 shown in FIG. 41K has a butterfly shape having large proximal wings 519, smaller pointed distal wings 520, and a keyhole-shaped aperture 521. Finally, FIG. 41L shows an adhesive patch 522 which has a proximal slit 523 along a top edge and a distal slit 526 along a bottom edge, an aperture 525 having an oval shape, and a narrow central section 524 on both sides of the aperture 525.

Now with reference to FIGS. 42-44C which show the adhesive patch of FIGS. 37A-B described above, along with two variations thereof. The adhesive patch 530 of FIG. 42 has an oval aperture 535, a proximal end having two proximal slits 534, a distal end having a slit 536, and a central section 532 on either side of the aperture 535. The central section 532 has a convex base and together with the proximal slits 534, delineates proximal wings 538. The distal edge has a slit 536, and together with the central section 532 delineates distal wings 540.

Figure 43:
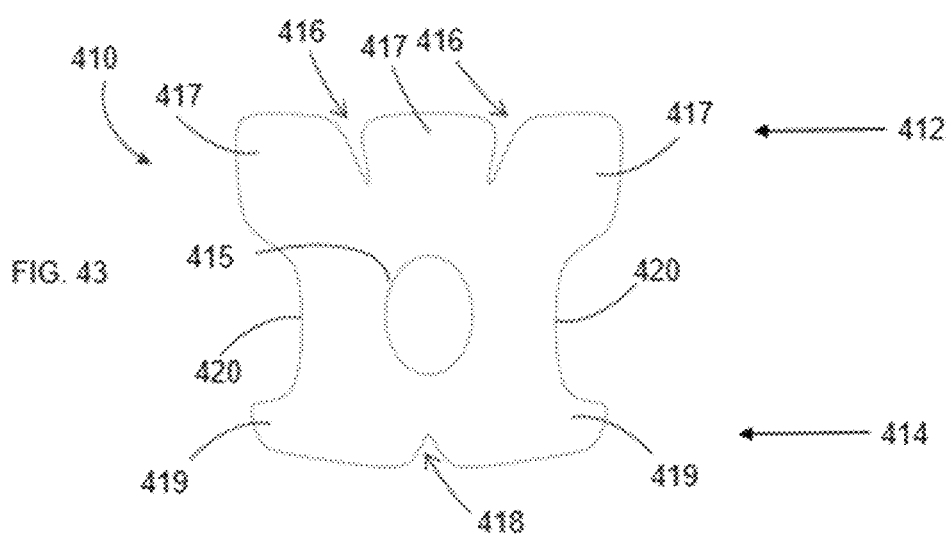
FIG. 43 illustrates a plan view of the adhesive patch of FIG. 37A.

FIG. 43 shows the same adhesive patch 410 as shown in FIG. 37A-B, but in a planar view to more accurately display the shape and proportions. The adhesive patch 410 has an oval aperture 415, a wide proximal end 412, and a wide distal end 414. The adhesive patch 410 has a narrowed central section 424 defined by concave sidewalls 420. The proximal end 412 may have one or more slits 416 dividing the adhesive patch 410 into proximal tabs 417. Likewise, the distal end 414 may have a slit 418 dividing the adhesive patch 410 into distal tabs 419. The proximal end 412 and the distal end 414 attach to the suprapubic region and scrotum respectively while the central section 413 lays around the penile shaft.

Figure 44:
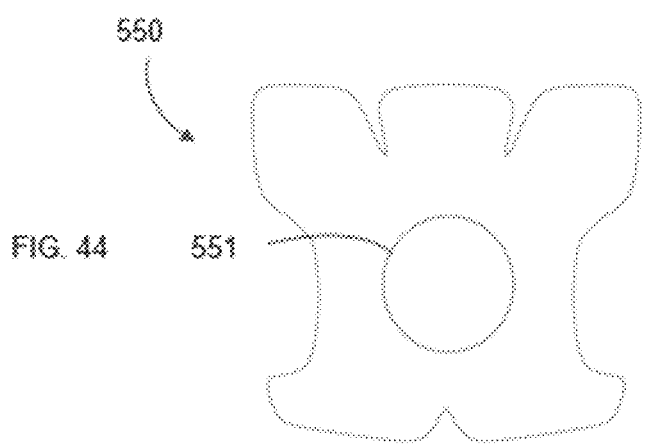
FIGS. 44-46 illustrate adhesive patch shapes according to other example embodiments.
Figure 45:
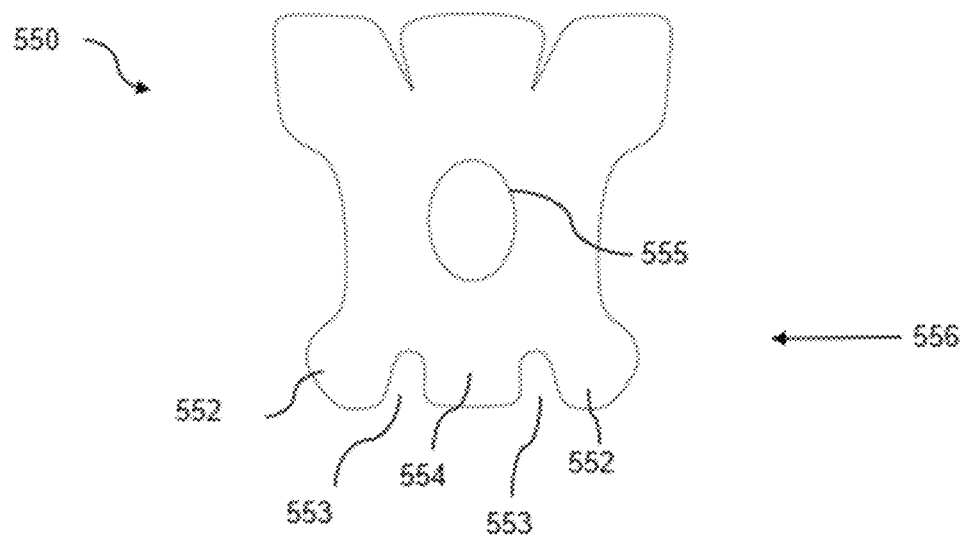
Figure 46:
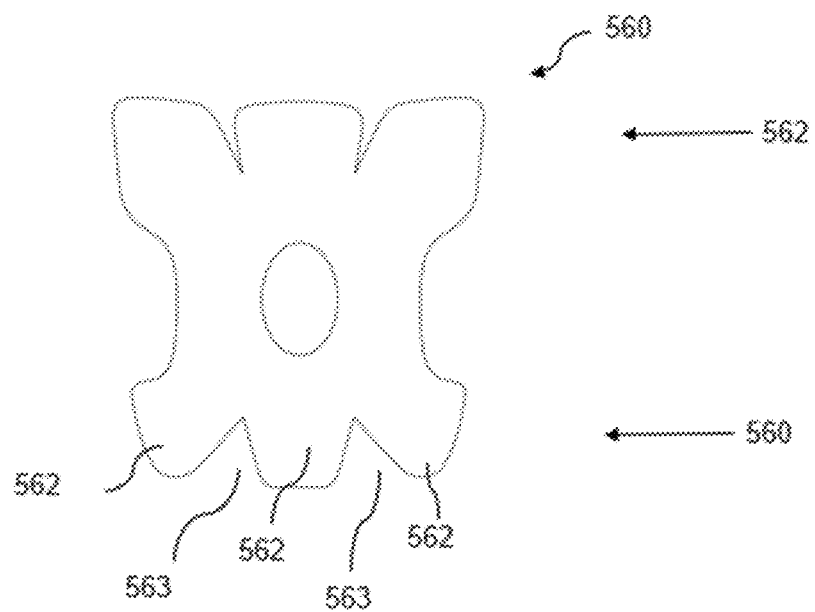

Another embodiment of an adhesive patch 550 is shown in FIG. 44; the patch 550 is otherwise the same as the previously described embodiment shown in FIG. 43, except that it has an aperture 551 which is circular. FIG. 45 illustrates another embodiment of an adhesive patch 550 having an oval aperture 555, wherein the distal end 556 is provided with a plurality of slits 553, dividing the distal end 556 into distal tabs 552, 554. The additional number of distal tabs promotes secure fastening of the adhesive patch 550. FIG. 46 illustrates another embodiment of an adhesive patch 5560 having an oval aperture 561B, wherein distal end 559 is provided with a plurality of slits 563 dividing said distal end 560 into distal tabs 562. The shape of the distal tabs 562 illustrated in FIG. 46 are a variation of the shapes of the distal tabs of FIG. 45, having a more open "V" shape, for improving adhesion to (or fastening over) the suprapubic region.

In some embodiments (for example, the urine removal device 570 of FIG. 47), an adhesive patch 571 may be removably attached to the pouch 572. That is, the adhesive patch 571 may be connected to the pouch 572 via an interface that may use threads, a twist-lock (¼ or ½ turn for example), an interfacing male/female flange pair 574 and 576, or any suitable interfacing component pair (comprising first and second interfacing components configured that interface with each other). The pouch 572 may have a corresponding interfacing member or receiving member 576 such as a flange to match a connector 574 on the adhesive patch 571. A detachable interface of this kind allows the operator to remove the pouch for cleaning or replacement while leaving the patch 571 secured via adhesive around the penis, which may save the operator time and effort while preventing any discomfort to the patient that may be incurred while removing and applying the adhesive patch.

Figure 48:
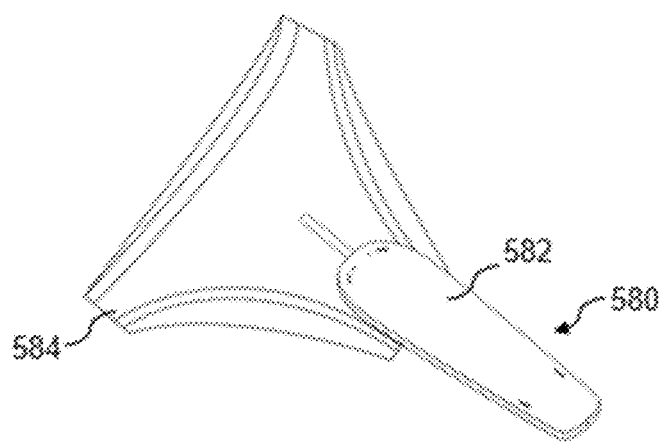
FIG. 48 illustrates a device having a removable attachment to a clothing.

FIG. 48 illustrates an embodiment of the urine removal device 580 that is capable of being affixed to clothing (for example, a diaper or undergarment 584 worn by a patient).

Figure 47:
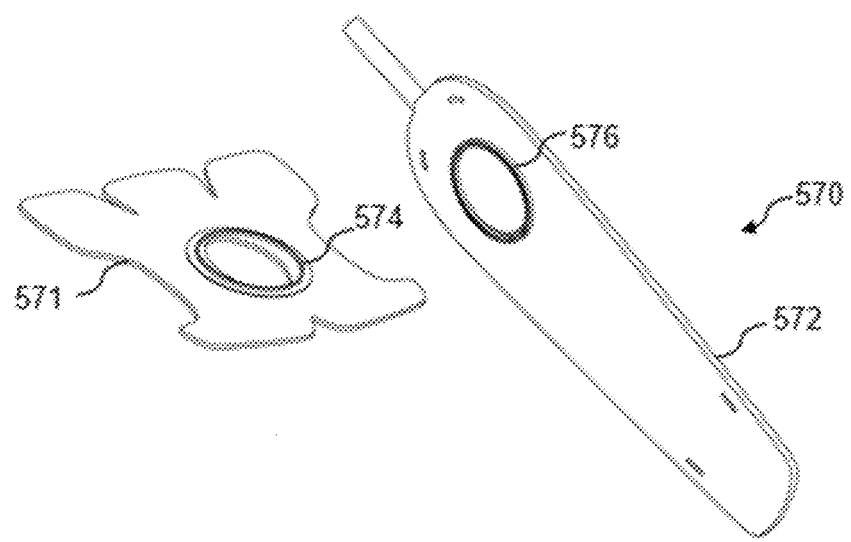
FIG. 47 illustrates a device having a removable attachment for the pouch.

As would be apparent from FIG. 48 that this may in an embodiment be achieved by incorporating the interfacing mechanism that has been discussed in connection with FIG. 47. In the embodiment illustrated in FIG. 48 the undergarment 584 to which the urine removal device 580 is intended to be affixed is provided with one of an interfacing component pair, or any other suitable interface, while the pouch 582 may have the other of the interfacing component pair (comprising first and second interfacing components configured to interface with each other) which enables the urine removal device 580 and the undergarment 584 to be removably interfaced. While the interfacing components are hidden in FIG. 48, they are similar to that shown in FIG. 47, namely, the first interfacing component may be affixed to the article of clothing, while the second interfacing component may be affixed to the pouch 582. By providing an aperture within the interfacing component (that is affixed to the article of clothing), and by providing affixing the second interfacing component onto the pouch 582, in a manner that it surrounds the aperture formed within pouch 582, the patient's penis can pass through such aperture and the interfacing component pair and into pouch 582 through the aperture provided on pouch 582. The interfacing component pair of FIGS. 47 and 48 may be configured to provide a fluid tight interference between the components.

Figure 49:
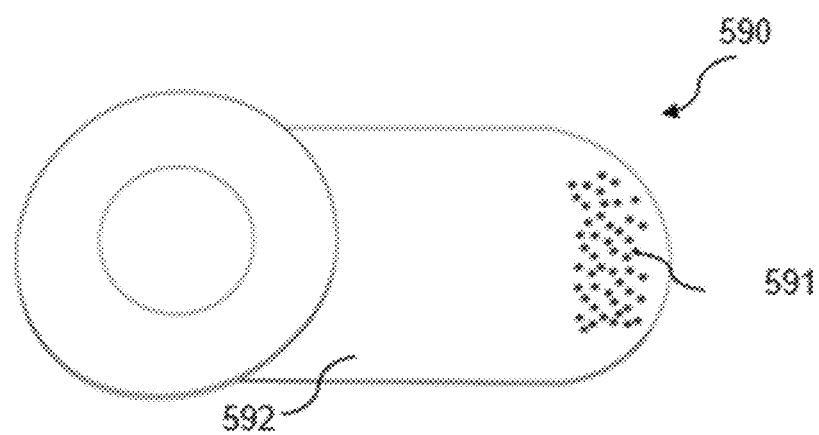
FIG. 49 illustrates an embodiment of the urine removal device that has superabsorbent material within the pouch.

In another embodiment, as illustrated in FIG. 49, a urine capture device 590 has a pouch 592 which includes one or more super-absorbent materials 591 (for example, a super-absorbent polymer) disposed therewithin, which when in contact with urine 25, the super-absorbant material 591 binds to form a non-liquid composition to prevent or minimize leakage or pooling of urine. It is within the scope of this disclosure that this super-absorbant material 591 may be included in other pouches presented herein to improve performance.

Figure 50:
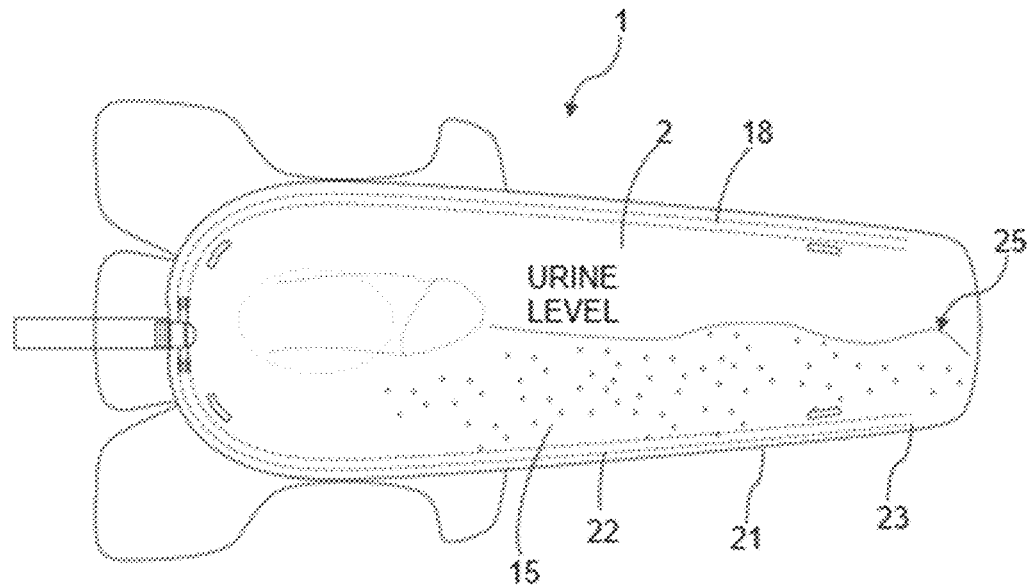
FIG. 50 illustrates the urine removal device oriented on a side showing urine temporarily pooling to one side of the device according to an example embodiment.

In some embodiments, urine evacuation may be improved by having one conduit member blocked so that suction is preferentially diverted to another conduit member. For example, FIG. 50 shows the urine removal device 1 previously described (also shown in FIG. 13) tilted sideways during use; the overall orientation is indicated by the arrow depicting gravity. Since the first conduit member 18 is not exposed to much urine, if any, the conduit member 18 will suck in air which may reduce the suction of the second conduit member 22 which is exposed to more urine due to the gravitational settling of the liquid. A conduit system having a valve that automatically blocks the upper conduit member (18) while allowing the lower conduit to maintain suction may increase the efficacy of the evacuation.

Figure 51:
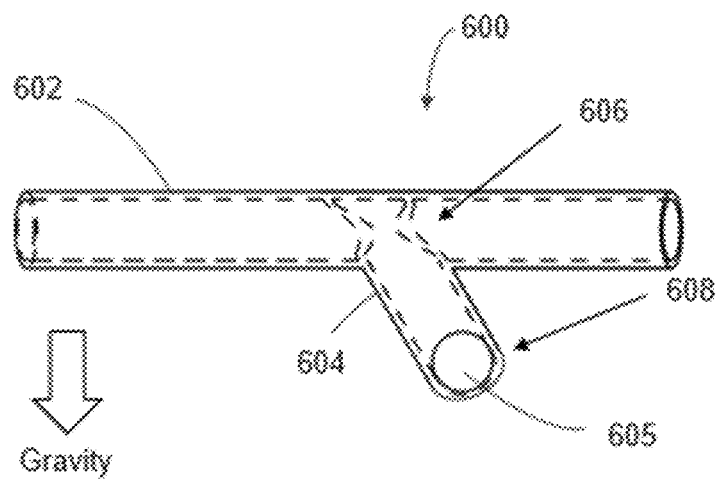
FIG. 51 illustrates an embodiment of a section of a conduit having a valve, wherein the valve is in the open configuration.

Now with reference to FIG. 51 which illustrates an example of a valve 600 for blocking flow in a conduit. The valve 600 comprises a section of a main conduit member 602 for evacuating urine, a branch 604 extending from the conduit member 602, and a ball 605 captive inside of the branch 604. The ball 605 is constrained to move between the end 608 of the branch and a retaining feature 606 inside of the lumen of the conduit member 602. As shown in FIG. 51 the valve 600 is in the open position such that flow is permitted through the conduit member 602.

Figure 52:
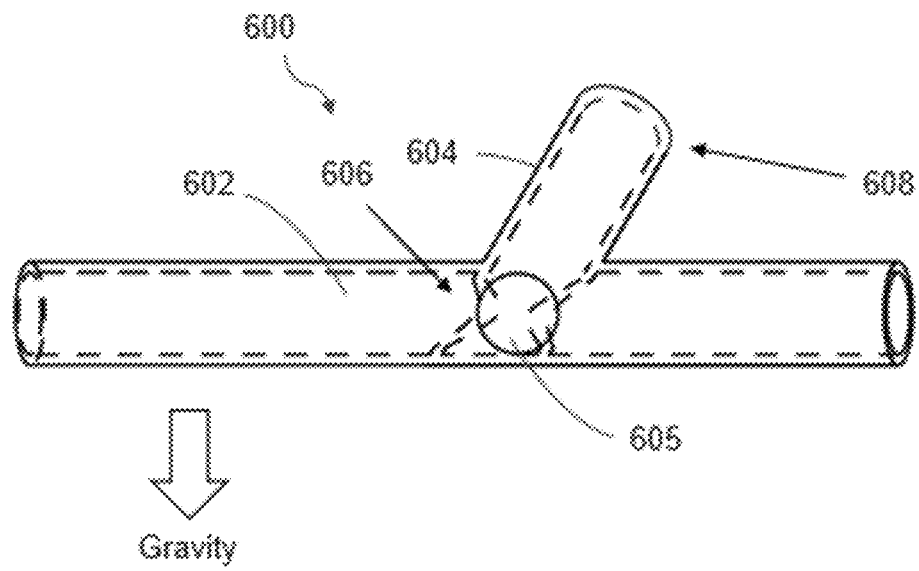
FIG. 52 illustrates an embodiment of a section of a conduit having a valve, wherein the valve is in the closed configuration.

FIG. 52 shows the valve 600 in the opposite (inverted) position wherein the flow in the conduit member 602 is blocked. When the branch 604 is substantially aligned with gravity, the ball 605 falls until it is stopped by the retaining feature 606, such that the ball 605 resides in the lumen of the conduit member 602 thus blocking or partially blocking fluid (air or liquid) flow past the ball 605. One skilled in the art would recognize that the ball 605 should be sized so that it fits into the retaining feature 606 at least partially blocking the conduit member 602 and is still free to translate back into the branch 604 when the orientation of the valve 600 changes. In embodiments a valve may be integral to the conduit member, or it may be a modular joint, like a "T" joint that can be attached in-line in a conduit.

Figure 53:
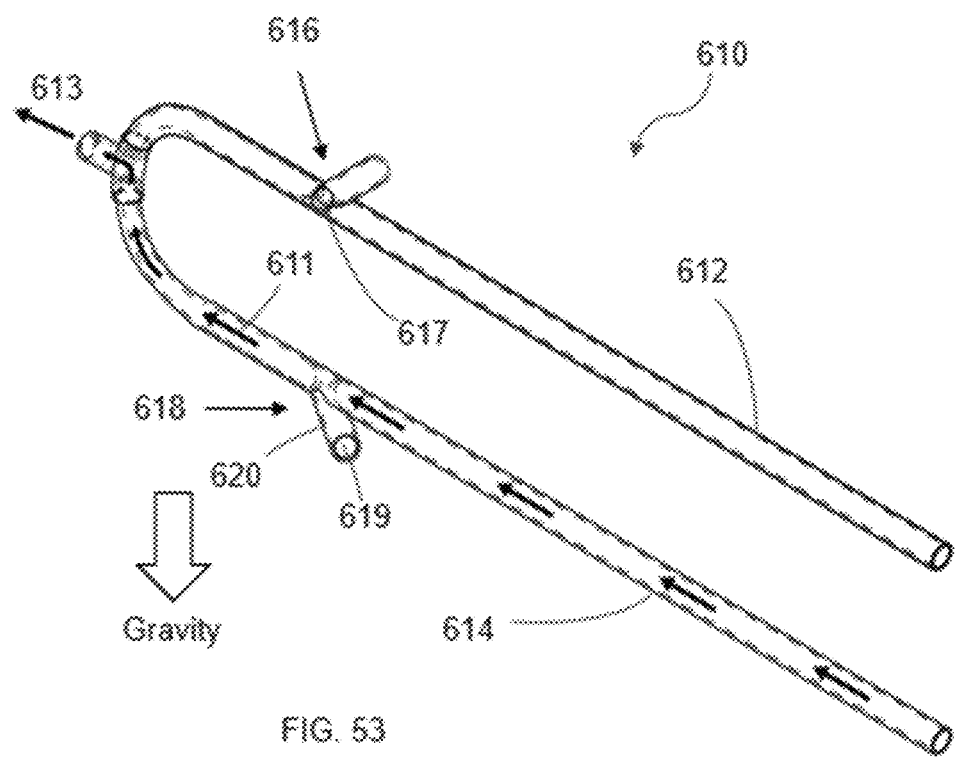
FIG. 53 illustrates a perspective view of an embodiment of a conduit system oriented horizontal or at an angle with respect to gravity.

FIG. 53 illustrates a conduit system 610 having a first valve 616 and a second valve 618, located on a first conduit member 612 and a second conduit member 614, respectively. In this embodiment, each valve is similar to that shown in FIGS. 51 and 52, however, the valves 616 and 618 have opposing orientations (facing away from the centerline of the conduit system 610) on each conduit member 612 and 614 such that only one valve closes when the system 610 tilts. The second valve 618 is in an open condition such that the ball 619 captive at the end of the branch 620 and away from the lumen of the second conduit member 614. This allows flow indicated by arrow 611 through the second conduit 614 and out of the suction conduit 613. In contrast, the first valve 616 is in the closed state because the ball has fallen into the lumen of the first conduit member 612, thus partially or full blocking air flow and permitting a stronger suction through the second conduit member 614 that is exposed to urine (not shown).

Figure 54:
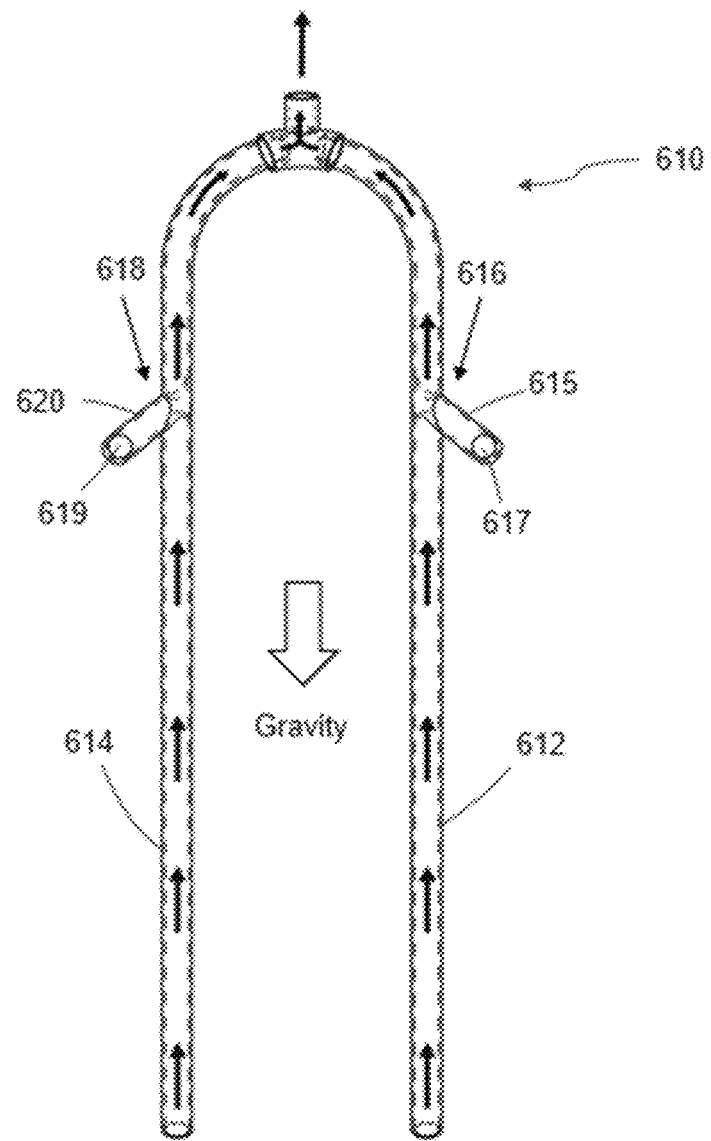
FIG. 54 illustrates an embodiment of a conduit system oriented vertically with respect to gravity.

Now with reference to FIG. 54, which shows the conduit system 610 of FIG. 53 in an upright orientation as if looking at a patient who is standing—gravity is pointing downward. This orientation shows that the branches 615 and 620 of the first and second valves 616 and 618, respectively, are oriented laterally and pointing somewhat downward from each conduit member 612 and 614, respectively. In the state shown, the conduit system 610 is open in both branches so that flow may ensue, as both conduit members 612 and 614 are open to fluid flow as indicated by the arrows. Thus, to accommodate both scenarios where the patient is standing and lying in bed with the conduit system on an angle, the branches are tilted downward and outward. One skilled in the art will recognize that there are many types of tilt activated valves that may be used for the purpose of substantially blocking one conduit member when a urine capture device tilts such that urine pools to one side of the pouch. Other valves accomplishing this function are within the scope and contemplated by this disclosure.

Method of Use

Figure 55:
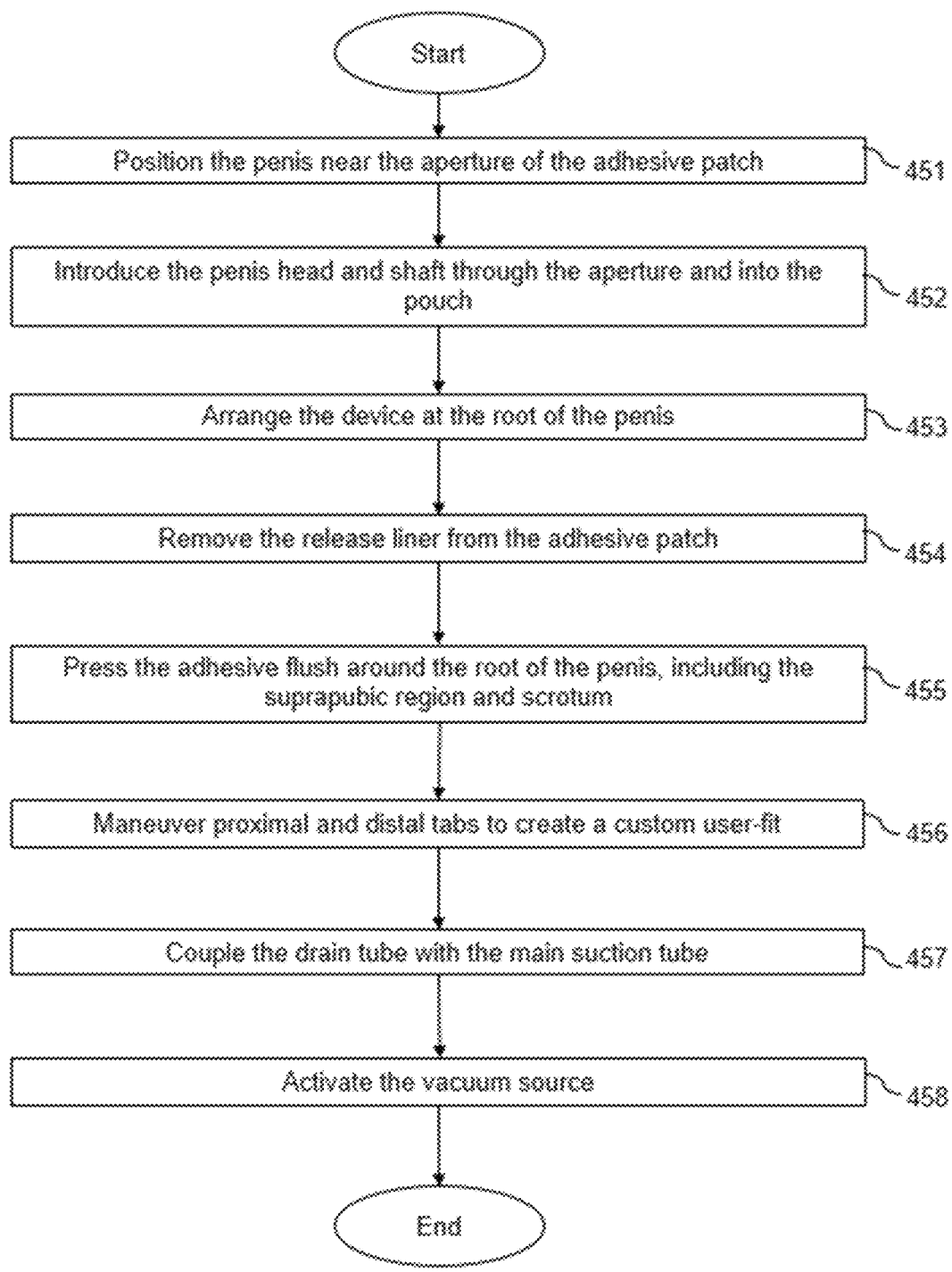
FIG. 55 is a flow chart illustrating the method of using a urine removal device according to an example embodiment.

With respect to the general use of embodiments of this disclosure, for clarity, a reader should refer to FIGS. 1A-B, which show an embodiment of a device, FIGS. 3A-3B, which provide a depiction of an embodiment during use on a user and along with vacuum source, FIG. 37A-37B, which details an exemplar layering of an adhesive patch, and FIG. 55, which represents a flowchart of a use scenario in some embodiments. The order of operations is for illustration only and is not meant to be limiting, as some operators may prefer an alternate sequence of steps, additional steps, or fewer steps. Such variations and modifications are within the scope and spirit of the inventions and embodiments contemplated herein.

Referring to FIG. 55 (and FIGS. 1A-1B, FIGS. 3A-3B, and FIGS. 37A-37B) first, a user may align the head of a penis with the aperture 43, and concomitantly, aperture 3 (step 451), such that positioning of the device over the penis will introduce the penis at least partially between first wall 4 and second wall 6 of the pouch 2 (step 452). It should be noted that in certain users, namely those with retracted or short-shaft penile variations, may only experience the aperture 43 (of the adhesive patch) surrounding the penis without touching or interacting with second wall 6. The device may subsequently be moved proximally toward the user such that adhesive patch 8 is in contact with or substantially near the root of the penis and surrounding skin (step 453). The release liner 423 may be removed from the adhesive layer 421 (step 454) to expose the inner surface 422b (not shown), which is sticky or tacky, and press the adhesive patch 8 against the skin adheres the inner surface 422b of the adhesive layer 422 such that it resides flush with the user (step 455). If required, the proximal tabs 417 and distal tabs 419 may be maneuvered either during adhesion or afterward to assist in customizing the adhesive fit with the user (step 456). Next, a drain tube 38 may be temporarily and removably coupled with suction source tube 24 (step 457), after which the vacuum source 44 may be activated (step 458). With reference to the flowchart of FIG. 55, as previously noted, it would not be necessary for each step to occur in the illustrated sequence; for example, steps 454 and 458 may be performed at a number of earlier stages.

The devices described in embodiments herein provide for urine removal devices that may be used by patients or other users in the prone position, lying sideways, or sitting because the designs are effective at containing urine without leaking and evacuating urine quickly away from the anatomy.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A urine removal device comprising:
    a flexible pouch having a front formed of a first sheet and a back formed of a second sheet, wherein the first sheet and the second sheet are joined together at a periphery of the pouch;
    an aperture through the back of the pouch, the aperture opening into an internal compartment within the pouch, wherein the aperture is configured to receive at least a part of a penis;
    first polymeric tube within the internal compartment extending from a proximal end region of the pouch along a right side of the periphery of the internal compartment of the pouch and ending in a first fluid inlet at a distal end region of the pouch on the right side, and a second polymeric tube within the internal compartment extending along from the proximal end region of the pouch along a left side of the periphery of the internal compartment of the pouch and ending in a second fluid inlet at the distal end region of the pouch on the left side, wherein the first polymeric tube and the second polymeric tube have a stiffness that prevents the first sheet and the second sheet from wrinkling or folding in an axis transverse to a distal-to-proximal axis, wherein the first polymeric tube and the second polymeric tube are coupled to a suction source tube;
    flow directors provided within the internal compartment of the pouch, wherein the flow directors provide a plurality of channels from the proximal end region of the pouch to the distal end region of the pouch when suction is applied within the internal compartment from the first fluid inlet and the second fluid inlet; and
    a fastener to secure the pouch in communication with the penis.

2. The urine removal device of claim 1, wherein the flow directors comprise a layer of polymeric fibers forming the plurality of channels.

3. The urine removal device of claim 2, wherein a majority of the plurality of channels are oriented in a substantially proximal to distal direction.

4. The urine removal device of claim 1, wherein the flow directors comprise a hydrophobic non-wicking material.

5. The urine removal device of claim 1, wherein the flow directors comprise an array of fibers attached to the first sheet, the second sheet, or both the first and second sheet.

6. The urine removal device of claim 1 wherein each polymeric tube is a rigid or partially rigid shaft.

7. The urine removal device of claim 1, wherein the first sheet and the second sheet are formed of a polymeric material having a thickness 1 mm or less, and wherein the first polymeric tube and the second polymeric tube have an internal diameter of 0.5 mm or greater.

8. The urine removal device of claim 1, wherein the first and second polymeric tubes form a frame that separates two opposing inner walls of the pouch.

9. The urine removal device of claim 1, further comprising one or more longitudinal folds in the first sheet extending from the proximal end region to the distal end region.

10. The urine removal device of claim 1, further comprising an adapter coupling the first polymeric tube and the second polymeric tube to the suction source tube and comprising a flexible joint to at least partially isolate the pouch from motion of the suction source tube.

11. The urine removal device of claim 1, wherein a distance between the first fluid inlet and the second fluid inlet is greater than a width of the aperture.

12. The urine removal device of claim 1, wherein the flow directors include grooves, ridges or grooves and ridges having a channel depth of 1 mm or less.

13. The urine removal device of claim 1, further comprising a second flow directing spacer within the internal compartment.

14. The urine removal device of claim 1, wherein the fastener comprises an adhesive patch attached to the flexible pouch, the adhesive patch configured for fastening the flexible pouch to a patient's suprapubic region.

15. A urine removal device comprising:
a flexible pouch having a front formed of a first sheet and a back formed of a second sheet, wherein the first sheet and the second sheet are sealed together;
an aperture through the back of the pouch, the aperture opening into an internal compartment of the pouch, wherein the aperture is configured to receive at least a part of a penis; a suction source tube extending proximally from the flexible pouch and configured to couple to a source of vacuum;
a first polymeric tube within the internal compartment extending from a proximal end region of the pouch along a right side of the internal compartment of the pouch and ending in a first fluid inlet at a right side of a distal end region of the internal compartment of the pouch and a second polymeric tube extending from a proximal end region of the pouch along a left side of the internal compartment of the pouch and ending in a second fluid inlet at a left side of the distal end region of the internal compartment of the pouch, wherein the first polymeric tube and the second polymeric tube have a stiffness that prevents the first sheet and the second sheet from wrinkling or folding;
the first polymeric tube and the second polymeric tube coupled to the suction source tube by an adapter;
one or more air ports through a proximal end region of the pouch to allow ambient air into the internal compartment of the pouch;
flow directors extending within the internal compartment of the pouch, wherein the flow directors provide a plurality of channels from the proximal end region to the distal end region within the internal compartment when suction is applied within the internal compartment from the first fluid inlet and the second fluid inlet; and
an adhesive patch attached to the flexible pouch, the adhesive patch configured for fastening said flexible pouch to a patient's suprapubic region.

16. The urine removal device of claim 15, wherein the flow directors comprise a layer of polymeric fibers forming the plurality of channels.

17. The urine removal device of claim 16, wherein a majority of the plurality of channels are oriented in a substantially proximal to distal direction.

18. The urine removal device of claim 15, wherein the flow directors comprise a hydrophobic non-wicking material.

19. The urine removal device of claim 15, wherein the flow directors comprises an array of fibers attached to the first sheet, the second sheet, or both the first and second sheet.

20. The urine removal device of claim 15, wherein the adapter comprises a flexible joint proximal to the pouch to at least partially isolate the pouch from motion of a suction source tube.

21. The urine removal device of claim 15, wherein the first and second polymeric tubes form a frame that separates two opposing inner walls of the pouch.

22. The urine removal device of claim 15, further comprising one or more longitudinal folds in the first sheet extending from the proximal end region to the distal end region.

23. The urine removal device of claim 15, wherein a distance between the first fluid inlet and the second fluid inlet is greater than a width of the aperture.

24. The urine removal device of claim 15, wherein the flow directors include grooves, ridges or grooves and ridges having a channel depth of 1 mm or less.

25. A urine removal device comprising:
a flexible pouch having a front formed of a first sheet of liquid-impermeable material and a back formed of a second sheet of liquid-impermeable material, wherein the first sheet and the second sheet are sealed together at a periphery of the pouch;
an aperture through the back of the pouch, the aperture opening into an internal compartment within the pouch, wherein the aperture is configured to receive at least a part of a penis;
a suction source tube extending proximally from the flexible pouch and configured to couple to a source of vacuum;
a first polymeric tube and a second polymeric tube within the internal compartment and extending from a proximal end region of the pouch, the first and second polymeric tubes forming a frame, wherein the first polymeric tube extends along a right side of a periphery of the internal compartment of the pouch and ends in a first fluid inlet at a distal end region of the pouch on the right side, and wherein the second polymeric tube extends along a left side of the periphery of the internal compartment of the pouch and ends in a second fluid inlet at the distal end region of the pouch on the left side, wherein the frame prevents the first sheet and the second sheet from wrinkling or folding in an axis transverse to a distal-to-proximal axis of the urine removal device;
an adapter coupling the first polymeric tube and the second polymeric tube to the suction source tube;
one or more air ports through a proximal end region of the pouch to allow ambient air into the internal compartment of the pouch;
a flow directors layer extending within the internal compartment of the pouch, wherein the flow directors layer provides channels from the proximal end region of the pouch to the distal end region of the pouch within the internal compartment when suction is applied within the internal compartment from the first fluid inlet and the second fluid inlet; and a fastener to secure the pouch in communication with the penis.

\* \* \* \* \*